United States Patent
Molino et al.

(10) Patent No.: US 7,361,636 B2
(45) Date of Patent: Apr. 22, 2008

(54) CYCLOSPORIN ALKYNES AND THEIR UTILITY AS PHARMACEUTICAL AGENTS

(75) Inventors: Bruce F. Molino, Slingerlands, NY (US); Zhicai Yang, Schenectady, NY (US)

(73) Assignee: AMR Technology, Inc., Manchester Center, VT (US)

( * ) Notice: Subject to any disclaimer, the term of this patent is extended or adjusted under 35 U.S.C. 154(b) by 293 days.

(21) Appl. No.: 11/232,293

(22) Filed: Sep. 21, 2005

(65) Prior Publication Data

US 2006/0074015 A1    Apr. 6, 2006

Related U.S. Application Data

(60) Provisional application No. 60/616,591, filed on Oct. 6, 2004.

(51) Int. Cl.
*A61K 38/12* (2006.01)
(52) U.S. Cl. ..................... 514/11; 530/317
(58) Field of Classification Search ............ None
See application file for complete search history.

(56) References Cited

U.S. PATENT DOCUMENTS

| | | | |
|---|---|---|---|
| 4,210,581 A | 7/1980 | Ruegger et al. | |
| 4,288,431 A | 9/1981 | Traber et al. | |
| 4,384,996 A * | 5/1983 | Bollinger et al. | 530/321 |
| 4,396,542 A | 8/1983 | Wenger | |
| 4,554,351 A | 11/1985 | Wenger | |
| 4,639,434 A | 1/1987 | Wenger et al. | |
| 4,649,047 A | 3/1987 | Kaswan | |
| 4,703,033 A | 10/1987 | Seebach | |
| 4,727,035 A | 2/1988 | Mahoney | |
| 4,764,503 A | 8/1988 | Wenger | |
| 4,771,122 A | 9/1988 | Seebach | |
| 4,839,342 A | 6/1989 | Kaswan | |
| 4,885,276 A | 12/1989 | Witzel | |
| 5,030,739 A | 7/1991 | Foricher et al. | |
| 5,116,816 A | 5/1992 | Dreyfuss et al. | |
| 5,169,773 A | 12/1992 | Rosenthaler et al. | |
| 5,284,826 A | 2/1994 | Eberle | |
| 5,318,901 A | 6/1994 | Patchett et al. | |
| 5,411,952 A | 5/1995 | Kaswan | |
| 5,525,590 A | 6/1996 | Bollinger et al. | |
| 5,643,870 A | 7/1997 | Boelsterli et al. | |
| 5,767,069 A | 6/1998 | Ko et al. | |
| 5,834,266 A | 11/1998 | Crabtree et al. | |
| 5,840,900 A | 11/1998 | Greenwald et al. | |
| 5,846,514 A | 12/1998 | Foster et al. | |
| 5,869,337 A | 2/1999 | Crabtree et al. | |
| 5,869,709 A | 2/1999 | Marwah et al. | |
| 5,948,693 A | 9/1999 | Rich et al. | |
| 5,981,479 A | 11/1999 | Ko et al. | |
| 5,994,299 A | 11/1999 | Barriere et al. | |
| 6,255,100 B1 | 7/2001 | Ko et al. | |
| 6,605,593 B1 | 8/2003 | Naicker et al. | |
| 6,613,739 B1 | 9/2003 | Naicker et al. | |
| 6,686,454 B1 | 2/2004 | Yatscoff et al. | |
| 6,723,339 B2 | 4/2004 | Meinzer et al. | |
| 6,767,555 B2 | 7/2004 | Ambuhl et al. | |
| 6,784,156 B2 | 8/2004 | Or et al. | |
| 6,809,077 B2 | 10/2004 | Or et al. | |
| 6,844,459 B2 | 1/2005 | Hauer et al. | |
| 6,927,208 B1 | 8/2005 | Wenger et al. | |
| 6,979,671 B2 | 12/2005 | Or et al. | |
| 6,998,385 B2 | 2/2006 | Naicker et al. | |
| 7,012,064 B2 | 3/2006 | Or et al. | |
| 7,012,065 B2 | 3/2006 | Or et al. | |
| 7,060,672 B2 | 6/2006 | Naicker et al. | |
| 2002/0127198 A1 | 9/2002 | Rothbard et al. | |
| 2002/0128470 A1 | 9/2002 | Fuenfschilling et al. | |
| 2002/0132763 A1 | 9/2002 | Naicker et al. | |

(Continued)

FOREIGN PATENT DOCUMENTS

BR    9603738-5 A    5/1998

(Continued)

OTHER PUBLICATIONS

[Retrived from] http://www.netLibrary.com/urlapi.asp?action=summary&v=1&bookid=25636, 2007, 3 pages, [retrieved on Nov. 21, 2007].*

(Continued)

*Primary Examiner*—Anish Gupta
*Assistant Examiner*—Satyanarayana R. Gudibande
(74) *Attorney, Agent, or Firm*—Nixon Peabody LLP

(57) ABSTRACT

The compounds of the present invention are represented by the chemical structure found in Formula I:

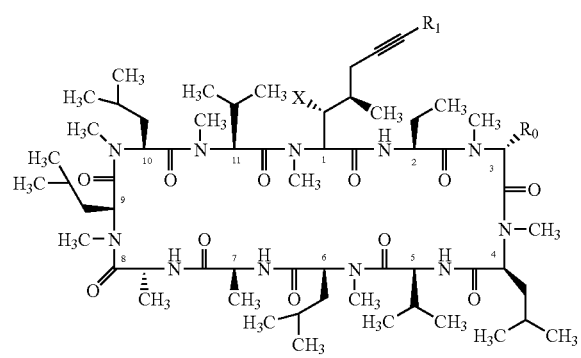

Formula I or a pharmaceutically acceptable salt thereof,
with X, $R_0$, and $R_1$ defined herein.

12 Claims, 1 Drawing Sheet

U.S. PATENT DOCUMENTS

| | | | |
|---|---|---|---|
| 2002/0142946 A1* | 10/2002 | Or et al. ................. | 514/9 |
| 2003/0022831 A1 | 1/2003 | Rothbard et al. | |
| 2003/0087813 A1 | 5/2003 | Or et al. | |
| 2003/0104992 A1 | 6/2003 | Or et al. | |
| 2003/0109425 A1 | 6/2003 | Or et al. | |
| 2003/0109426 A1 | 6/2003 | Or et al. | |
| 2003/0139326 A1 | 7/2003 | Naicker et al. | |
| 2003/0166515 A1 | 9/2003 | Or et al. | |
| 2003/0171264 A1 | 9/2003 | Naicker et al. | |
| 2006/0217309 A1 | 9/2003 | Naicker et al. | |
| 2003/0186855 A1 | 10/2003 | Or et al. | |
| 2003/0212249 A1 | 11/2003 | Naicker et al. | |
| 2003/0220234 A1 | 11/2003 | Naicker et al. | |
| 2004/0087496 A1 | 5/2004 | Kim et al. | |
| 2004/0110666 A1 | 6/2004 | Or et al. | |
| 2004/0157768 A1 | 8/2004 | Or et al. | |
| 2004/0220091 A1 | 11/2004 | Adam et al. | |
| 2004/0235716 A1 | 11/2004 | Molino et al. | |
| 2004/0266669 A1 | 12/2004 | Wu et al. | |
| 2005/0176628 A1 | 8/2005 | Naicker et al. | |
| 2005/0192214 A1 | 9/2005 | Naicker et al. | |
| 2006/0035821 A1 | 2/2006 | Hunt et al. | |
| 2006/0035822 A1 | 2/2006 | Hunt et al. | |
| 2006/0052290 A1 | 3/2006 | Naicker et al. | |
| 2006/0069015 A1 | 3/2006 | Molino et al. | |
| 2006/0069016 A1 | 3/2006 | Molino et al. | |
| 2006/0074015 A1 | 4/2006 | Molino et al. | |
| 2006/0135414 A1 | 6/2006 | Naicker et al. | |

FOREIGN PATENT DOCUMENTS

| | | |
|---|---|---|
| CA | 1106303 A2 | 8/1981 |
| CA | 1292962 C | 12/1991 |
| CA | 2076291 AA | 2/1993 |
| CA | 2096892 A | 11/1993 |
| CA | 2086267 AA | 6/1994 |
| CH | 628872 A | 3/1982 |
| CH | 630061 A | 5/1982 |
| CH | 630062 A | 5/1982 |
| CH | 637123 A | 7/1983 |
| CH | 640520 A | 1/1984 |
| CS | 277471 B6 | 3/1993 |
| CS | 277472 B6 | 3/1993 |
| CZ | 280552 B6 | 2/1996 |
| CZ | 280553 B6 | 2/1996 |
| DE | 2455859 A1 | 6/1975 |
| DE | 2648121 A1 | 5/1977 |
| DE | 2819094 A1 | 11/1978 |
| DE | 285793 A5 | 1/1991 |
| DE | 295245 A5 | 10/1991 |
| DE | 295870 A | 11/1991 |
| DE | 295871 A | 11/1991 |
| DE | 4032268 A1 | 4/1992 |
| DE | 4236237 A1 | 4/1994 |
| DE | 19933173 A1 | 1/2001 |
| DE | 102004011988 A1 | 9/2005 |
| EP | 0 034 567 | 11/1984 |
| EP | 283801 A2 | 9/1988 |
| EP | 300785 A2 | 1/1989 |
| EP | 375454 A1 | 6/1990 |
| EP | 444897 A1 | 9/1991 |
| EP | 471295 A1 | 2/1992 |
| EP | 473961 A2 | 3/1992 |
| EP | 487289 A2 | 5/1992 |
| EP | 642799 A1 | 3/1995 |
| FR | 2640641 A1 | 6/1990 |
| FR | 2757520 A1 | 6/1998 |
| FR | 2757521 A1 | 6/1998 |
| FR | 2757522 A1 | 6/1998 |
| FR | 2851471 A1 | 8/2004 |
| GB | 2205317 A1 | 12/1988 |
| GB | 2206119 A1 | 12/1988 |
| GB | 2207678 A1 | 2/1989 |
| GB | 2212499 A1 | 7/1989 |
| GB | 2227244 A1 | 7/1990 |
| JP | 57063093 A2 | 4/1982 |
| JP | 05271267 A2 | 10/1993 |
| JP | 07278187 A2 | 10/1995 |
| JP | 10279596 A2 | 10/1998 |
| JP | 2002080394 A2 | 3/2002 |
| JP | 20050198543 A2 | 7/2005 |
| JP | 20050325061 A2 | 11/2005 |
| KR | 161664 B1 | 11/1998 |
| KR | 2002089300 A | 11/2002 |
| RU | 2144017 C1 | 1/2000 |
| WO | WO 90/06763 | 6/1990 |
| WO | WO 92/06998 | 4/1992 |
| WO | WO 92/13094 | 8/1992 |
| WO | WO 92/13569 | 8/1992 |
| WO | WO 93/07150 | 4/1993 |
| WO | WO 94/18317 | 8/1994 |
| WO | WO 94/25606 | 11/1994 |
| WO | WO 95/02684 | 1/1995 |
| WO | WO 96/06111 | 2/1996 |
| WO | WO 96/06857 | 3/1996 |
| WO | WO 96/27607 | 9/1996 |
| WO | WO 96/40758 | 12/1996 |
| WO | WO 97/04005 | 2/1997 |
| WO | WO 97/11092 | 3/1997 |
| WO | WO 97/46575 | 12/1997 |
| WO | WO 98/03192 | 1/1998 |
| WO | WO 98/07713 | 2/1998 |
| WO | WO 98/08956 | 3/1998 |
| WO | WO 98/46247 | 10/1998 |
| WO | WO 98/49193 | 11/1998 |
| WO | WO 98/58927 | 12/1998 |
| WO | WO 98/02659 | 1/1999 |
| WO | WO 99/10373 | 3/1999 |
| WO | WO 99/10374 | 3/1999 |
| WO | WO 99/18120 | 4/1999 |
| WO | WO 99/21879 | 5/1999 |
| WO | WO 99/32512 | 7/1999 |
| WO | WO 99/62540 | 12/1999 |
| WO | WO 99/65933 | 12/1999 |
| WO | WO 99/67280 | 12/1999 |
| WO | WO 00/01715 | 1/2000 |
| WO | WO 00/08033 | 2/2000 |
| WO | WO 00/51558 | 9/2000 |
| WO | WO 00/67801 | 11/2000 |
| WO | WO 01/05819 A1 | 1/2001 |
| WO | WO 01/13957 A2 | 3/2001 |
| WO | WO 01/35913 A1 | 5/2001 |
| WO | WO 01/35914 A1 | 5/2001 |
| WO | WO 02/24865 A2 | 3/2002 |
| WO | WO 02/41858 A1 | 5/2002 |
| WO | WO 02/41859 A1 | 5/2002 |
| WO | WO 02/064106 A1 | 8/2002 |
| WO | WO 02/065986 A2 | 8/2002 |
| WO | WO 02/067917 A1 | 9/2002 |
| WO | WO 02/069902 A2 | 9/2002 |
| WO | WO 02/076927 A2 | 10/2002 |
| WO | WO 02/085928 A2 | 10/2002 |
| WO | WO 02/092032 A1 | 11/2002 |
| WO | WO 02/092033 A1 | 11/2002 |
| WO | WO 03/030834 A2 | 4/2003 |
| WO | WO 03/032949 A1 | 4/2003 |
| WO | WO 03/033010 A1 | 4/2003 |
| WO | WO 03/033526 A2 | 4/2003 |
| WO | WO 03/033527 A2 | 4/2003 |
| WO | WO 03/034980 A2 | 5/2003 |
| WO | WO 03/049772 A2 | 6/2003 |
| WO | WO 03/070755 A2 | 8/2003 |
| WO | WO 2004/050687 A2 | 6/2004 |
| WO | WO 2004/072108 A1 | 8/2004 |

| | | | |
|---|---|---|---|
| WO | WO 2004/082629 A2 | 9/2004 |
| WO | WO 2004/089960 A2 | 10/2004 |
| WO | WO 2004/096236 A2 | 11/2004 |
| WO | WO 2004/100960 A2 | 11/2004 |
| WO | WO 2005/000879 A1 | 1/2005 |
| WO | WO 2005/021028 A1 | 3/2005 |
| WO | WO 2005/046575 A2 | 5/2005 |
| WO | WO 2005/097164 A2 | 10/2005 |
| WO | WO 2006/005580 A1 | 1/2006 |
| WO | WO 2006/005610 A1 | 1/2006 |
| WO | WO 2006/014872 A2 | 2/2006 |
| WO | WO 2006/063470 A1 | 6/2006 |
| WO | WO 2006/066416 A1 | 6/2006 |
| WO | WO 2006/071618 A1 | 7/2006 |

OTHER PUBLICATIONS

Abel et a., "ISATX247: A Novel Calcineurin Inhibitor," *J. Heart Lung Transplant.* 20(2):161 (2001) (Abstract 36).

Aspeslet et al., "ISA$_{tx}$247: A Novel Calcineurin Inhibitor," *Transplant. Proc.* 33:1048-1051 (2001).

Buetler et al., "Does Cyclosporin A Generate Free Radicals?" *TIPS* 21:288-290 (2000).

Christians & Sewing, "Cyclosporin Metabolism in Transplant Patients," *Pharmac. Ther.* 57:291-345 (1993).

Clark & Yorio, "Ophthalmic Drug Discovery," *Nat. Rev. Drug Discov.* 2(6):448-459 (2003).

Dumont, "ISAtx-247 Isotechnika/Roche," *Curr. Opin. Investig. Drugs* 5(5):542-550 (2004).

Eberle et al., "Preparation of Sulfhydryl Cyclosporin A," *J. Org. Chem.* 60:2610-2612 (1995).

Eckstein & Fung, "A New Class of Cyclosporin Analogues for the Treatment of Asthma," *Expert Opin. Investig. Drugs* 12(4):647-653 (2003).

Foster, "Deuterium Isotope Effects in Studies of Drug Metabolism," *TIPS* 5:524-527 (1984).

Fritz-Langhals & Kunath, "Synthesis of Aromatic Aldehydes by Laccase-Mediator Assisted Oxidation," *Tetrahedron Lett.* 39:5955-5956 (1998).

Henke et al., "Cyclosporine A Inhibits ATP Net Uptake of Rat Kidney Mitochondria," *Biochem. Pharmacol.* 43(5):1021-1024 (1992).

Kallen et al., "12 Cyclosporins: Recent Developments in Biosynthesis, Pharmacology and Biology, and Clinical Applications," *Biotechnology*, Second Edition, Rehm et al, eds., pp. 535-591 (1997).

Khanna et al., "TGF-β: A Link Between Immunosuppression, Nephrotoxicity, and CsA," *Transplant. Proc.* 30:944-945 (1998).

Ko & Wenger, "53. Solid-Phase Total Synthesis of Cyclosporine Analogues," *Helvetica Chimica Acta* 80:695-705 (1997).

Lazarova et al., "Synthesis and Biological Evaluation of Novel Cyclosporin A Analogues: Potential Soft Drugs for the Treatment of Autoimmune Diseases," *J. Med. Chem.* 46:674-676 (2003).

Loor, "Cyclosporins and Related Fungal Products in the Reversal of P-Glycoprotein-Mediated Multidrug Resistance," in *Multidrug Resistance in Cancer Cells* Gupta et al, eds., John Wiley and Sons Ltd: Chichester, pp. 385-412 (1996).

Loor, "Valspodar: Current Status and Perspectives," *Exp. Opin. Invest. Drugs* 8(6):807-835 (1999).

Mlynar et al., "The Non-Immunosuppressive Cyclosporin A Analogue SDZ NIM 811 Inhibits Cyclophilin A Incorporation Into Virions and Virus Replication in Human Immunodeficiency Virus Type 1-Infected Primary and Growth-Arrested T Cells," *J. Gen. Virol.* 78(4):825-835 (1997).

Offenzeller et al., "Biosynthesis of the Unusual Amino Acid (4R)-4-[(E)-2-Butenyl]-4-methyl-L-threonine of Cyclosporin A: Enzymatic Analysis of the Reaction Sequence Including Identification of the Methylation Precursor in a Polyketide Pathway," *Biochem.* 35:8401-8412 (1996).

Paolini, "Cyclosporin A and Free Radical Generation," *TIPS* 22(1):14-15 (2001).

Park & Meier, "A Semi-Synthetic Approach to Olefinic Analogs of Amino Acid One (MeBMT) in Cyclosporin A," *Tetrahedron Lett.* 30(32):4215-4218 (1989).

Potthast et al., "A Novel Method for the Conversion of Benzyl Alcohols to Benzaldehydes by Laccase-Catalyzed Oxidation," *J. Mol. Catalysis A* 108:5-9 (1996).

Punniyamurthy & Iqbal, "Cobalt Catalysed Allylic and Benzylic Oxidations with Dioxygen in the Presence of Ethyl 2-Oxocyclopentanecarboxylate," *Tetrahedron Lett.* 35(23):4003-4006 (1994).

Seebach et al., "Modifications of Cyclosporin A (CS): Generation of an Enolate at the Sarcosine Residue and Reactions with Electrophiles," *Helvetica Chimica Acta* 76:1564-1590 (1993).

Seebach & Ko, "Thiocyclosporins: Preparation, Solution and Crystal Structure, and Immunosuppressive Activity," *Helvetica Chimica Acta* 74:1953-1990 (1991).

Serino et al., "Oxygen Radical Formation by the Cytochrome P450 System as a Cellular Mechanism for Cyclosporine Toxicity," *Transplant. Proc.* 26:2916-2917 (1994).

Serkova et al., "The Novel Immunosuppressant SDZ-RAD Protects Rat Brain Slices from Cyclosporine-Induced Reduction of High-Energy Phosphates," *Br. J. Pharmacol.* 129:485-492 (2000).

Snyder & Sabatini, "Immunophilins and the Nervous System," *Nat. Med.* 1(1):32-37 (1995).

Snyder et al., "Neural Actions of Immunophilin Ligands," *TIPS* 19:21-26 (1998).

Steiner et al., "Neurotrophic Actions of Nonimmunosuppressive Analogues of Immunosuppressive Drugs FK506, Rapamycin and Cyclosporin A," *Nat. Med.*3(4):421-428 (1997).

Traber et al., "Cyclosporins-New Analogues by Precursor Directed Biosynthesis," *J. Antibiotics* 42(4):591-597 (1989).

Traber et al., "122. Die Struktur von Cyclosporin C," *Helvetica Chimica Acta* 60(4):1247-1255 (1977) (English Abstract Only).

Traber et al., "162. Isolierung und Strukturermittlung der neuen Cyclosporine E, F, G, H und I," *Helvetica Chimica Acta* 65(5):1655-1677 (1982) (English Abstract Only).

Traber et al., "2. Neue Cyclosporine aus *Tolypocladium inflatum* Die Cyclosporine K-Z," *Helvetica Chimica Acta* 70:13-36 (1987) (English Abstract Only).

Wenger, "60. Synthesis of Cyclosporins: Total Syntheses of 'Cyclosporin A' and 'Cyclosporin H', Two Fungal Metabolites Isolated from the Species *Tolypocladium inflatum* G$_{AMS}$," *Helvetica Chimica Acta* 67(2):502-525 (1984).

Wenger, "Structures of Cyclosporine and Its Metabolites," *Transplant. Proc.* 22(3):1104-1108 (1990).

Xu et al., "Redox Chemistry in Laccase-Catalyzed Oxidation of N-Hydroxy Compounds," *Appl. Environ. Microbiol.* 66(5):2052-2056 (2000).

Aebi et al., "Synthesis, Conformation, and Immunosuppressive Activities of Three Analogs of Cyclosporin A Modified in the 1-Position," *Journal of Medicinal Chemistry* 33(3):999-1009 (1990), Abstract only.

Agathos et al., "Enhancement of Cyclosporin Production in a Tolypocladium inflatum Strain After Epichlorohydrin Treatment," *Journal of Biotechnology* 13(1):73-81 (1990), Abstract only.

Agathos et al., "The Fungal Production of Cyclosporins," *Annals of the New York Academy of Sciences*, 506(Biochem. Eng. 5):657-662 (1987), Abstract only.

Alberg et al., "Structure-Based Design of a Cyclophilin-Calcineurin Bridging Ligand," *Science* (Washington, DC, United States) 262(5131):248-250 (1993), Abstract only.

Andres et al., "Interaction of Lead(II) With Highly-Dentate Linear and Cyclic Polyamines," *Journal of the Chemical Society, Dalton Transactions: Inorganic Chemistry* (23):3507-3513 (1972-1999) (1993), Abstract only.

Angell et al. "Innovation and Perspectives in Solid Phase Synthesis & Combinatorial Libraries: Peptides, Proteins and Nucleic Acids—Small Molecule Organic Chemical Diversity, Collected Papers," in Epton, ed. *International Symposium*, 5th, London, Sep. 2-6, 1997 (1999), Meeting Date 1997, Mayflower Scientific Ltd.: Kingswinford, pp. 135-138, Abstract only.

Angell et al., "Solid-Phase Synthesis of Cyclosporin Peptides," *Journal of the American Chemical Society* 117(27):7279-7280 (1995), Abstract only.

Angell, "The Solid-Phase Synthesis Of Cyclosporin A Analogs," Diss. Abstr. Int., B 1997, 57(9):5657(1996), Abstract only.

Belshaw et al. "Cell-Specific Calcineurin Inhibition by a Modified Cyclosporin," *Journal of the American Chemical Society* 119(7):1805-1806 (1997), Abstract only.

Belshaw et al., "Controlling Protein Association and Subcellular Localization With a Synthetic Ligand That Induces Heterodimerization of Proteins," *Proceedings of the National Academy of Sciences of the United States of America*, 93(10):4604-4607 (1996), Abstract only.

Belshaw et al., "Rational Design of Orthogonal Receptor-Ligand Combinations," *Angewandte Chemie, International Edition In English*, 34(19):2129-2132 (1995), Abstract only.

Bencini et al., "Anaerobic Complexation of Cobalt(II) by [3k]aneNk (k =7–12) Polyazacycloalkanes," *Inorganic Chemistry* 28(12):2480-2482 (1989), Abstract only.

Bencini et al., "Synthesis and Ligational Properties of the Two Very Large Polyazacycloalkanes [33]aneN11 and [36]aneN12 Forming Trinuclear Copper(II) Complexes," *Inorganic Chemistry* 27(1):176-180 (1988), Abstract only.

Bencini et al., "Thermodynamic and Structural Aspects of the Interaction Between Macrocyclic Polyammonium Cations and Complexed Anions," *Inorganic Chemistry* 31(10):1902-1908 (1992), Abstract only.

Billich et al., Enzymic Synthesis of Cyclosporin A,: *Journal of Biological Chemistry* 262(36):17258-17259 (1987), Abstract only.

Billich et al., "Novel Cyclosporin Derivatives Featuring Enhanced Skin Penetration Despite Increased Molecular Weight," *Bioorganic and Medicinal Chemistry* 13(9):3157-3167 (2005), Abstract only.

Bohnstedt, "The Synthesis And Biological Activities Of Novel Backbone-Modified Analogs Of Cyclosporin A," Diss. Abstr. Int. B 1995, 55(11), 4848 (1994), Abstract only.

Brooks et al., "Preparative Chromatographic Purification of Cyclosporine Metabolites," *Clinical Chemistry* (Washington, DC, United States) 39(3):457-466 (1993), Abstract only.

Brugghe et al., "Simultaneous Multiple Synthesis and Selective Conjugation of Cyclized Peptides Derived from a Surface Loop of a Meningococcal Class 1 Outer Membrane Protein," *International Journal of Peptide & Protein Research* 43(2), 166-172 (1994), Abstract only.

Buchta et al., "A Cyclosporin From Mycelium Sterilae," *Phytochemistry* 48(7):1195-1198 (1998), Abstract only.

Burtscher et al., "Synthesis of [S-[1-14C]val7]VALSPODAR: Application of (+)/(−)-[13,14Cn]BABS and (+)/(−)-[13,14Cn]DPMGBS," *Journal of Labelled Compounds & Radiopharmaceuticals* 43(3):205-216 (2000), Abstract only.

Cacalano et al., "Antibodies to Cyclosporine A (CsA) by a Novel Route and Their Use to Monitor Cyclosporine Levels by Radioimmunoassay (RIA)," *Journal of Immunological Methods* 118(2):257-263 (1989), Abstract only.

Carry et al., "Semisynthetic Di- and Tri-Functionalized Non-Immunosuppressive Cyclosporin A Derivatives as Potential Anti-HIV 1 Drugs," *Synlett* (2):316-320 (2004), Abstract only.

Cerny et al., "Synthesis of [ω-3H-MeBmt1]-Cyclosporin A," *Journal of Labelled Compounds & Radiopharmaceuticals* 41(4):267-272 (1998), Abstract only.

Chen et al., "A Sensitive Enzyme Immunoassay for Cyclosporin Using Antibodies Generated Against A Novel Hapten," *Research Communications in Molecular Pathology and Pharmacology* 88(3):317-326 (1995), Abstract only.

Cho et al., "Water Soluble Cyclosporine Monomethoxy Poly(Ethyleneglycol) Conjugates as Potential Prodrugs," *Archives of Pharmacal Research* 27(6):662-669 (2004), Abstract only.

Chu et al., "A New Producer of Cyclosporin C," *Zhongguo Kangshengsu Zazhi* 23(1):1-5, 16 (1998), Abstract only.

Chu et al., "Production of Cyclosporin C by *Gliomastix luzulae* Isolated From Different Areas of China," *Zhongguo Kangshengsu Zazhi* 23(2):116-120 (1998), Abstract only.

Chu et al., "Screening of Antifungal Substances with Immunosuppressive Activity by Special Morphological Abnormalities of *Aspergillus clavatus*," *Zhongguo Kangshengsu Zazhi* 23(3):193-196 (1998), Abstract only.

Coates et al., "Radioimmunoassay of Salivary Cyclosporine With Use of Iodine-125-Labeled Cyclosporine," *Clinical Chemistry* (Washington, DC, United States), 34(8):1545-1551 (1988), Abstract only.

Colucci et al., "Synthesis of D-Lysine8-Cyclosporine A. Further Characterization of BOP-CI in the 2-7 Hexapeptide Fragment Synthesis," *Journal of Organic Chemistry* 55(9): 2895-2903 (1990), Abstract only.

Dai et al., "Study of the Reaction Between Cyclosporine A and 4-Benzoylbenzoic Acid," *Jingxi Huagong* 18(3):135-137 (2001), Abstract only.

Donatsch et al., "A Radioimmunoassay to Measure Cyclosporin A in Plasma and Serum Samples," *Journal of Immunoassay* 2(1):19-32 (1981), Abstract only.

Dreyfuss et al., "Cyclosporin A and C. New Metabolites From *Trichoderma polysporum* (Link ex Pers.) Rifai," *European Journal of Applied Microbiology* 3(2):125-133 (1976), Abstract only.

Dugave, "Study of the cis-trans Isomerization of the Amino-Acyl Prolyl Peptide Bond: Application to the Design of Novel Inhibitors of Immunophilins," *Current Organic Chemistry* 6(15):1397-1431 (2002), Abstract only.

Durette et al., "A study of the Correlation Between Cyclophilin Binding and in Vitro Immunsuppressive Activity of Cyclosporine A and Analogs," *Transplantation Proceedings* 20(2, Suppl. 2):51-57 (1988), Abstract only.

Eberle et al., "Bridged Cyclosporins," *Journal of Organic Chemistry* 60(15):4868-4872 (1995), Abstract only.

Eberle et al., "Cyclosporin A: Regioselective Ring Opening and Fragmentation Reactions via Thioamides. A Route to Semisynthetic Cyclosporins," *Journal of Organic Chemistry* 59(24):7249-7258 (1994), Abstract only.

Eberle et al., "Modifications of the MeBmt Side Chain of Cyclosporin A," *Bioorganic & Medicinal Chemistry Letters* 5(15):1725-1728 (1995), Abstract only.

Eberle et al., "Preparation and in Vitro Activities of Ethers of [D-Serine]8-cyclosporin," *Journal of Medicinal Chemistry* 38(11):1853-1864 (1995), Abstract only.

Eberle et al., "Preparation of [D-cysteine]8-Cyclosporin Via Intramolecular Sulfur Transfer Reaction," *Journal of Organic Chemistry* 58(3):673-677 (1993), Abstract only.

Eberle et al., "Preparation of Functionalized Ethers of Cyclosporin A," *Tetrahedron Letters* 35(35):6477-6480 (1994), Abstract only.

Eberle et al., "Synthesis of the Main Metabolite (OL-17) of Cyclosporin A," *Journal of Organic Chemistry*, 57(9):2689-2691 (1992), Abstract only.

Endo et al., "Solution-Phase Synthesis and Structural Analysis of N-Desmethylated Cyclosporin O Analogs," *Peptide Science* 39:383-386 Volume Date 2002, (2003), Abstract only.

Evers et al., "Synthesis of Non-Immunosuppressive Cyclophilin-Binding Cyclosporin A Derivatives as Potential Anti-HIV-1 Drugs," *Bioorganic & Medicinal Chemistry Letters* 13(24):4415-4419 (2003), Abstract only.

Fang et al., "Separation of Cyclosporins by High Speed Counter Current Chromatography," *Zhongguo Kangshengsu Zazhi* 30(1):48-51 (2005), Abstract only.

French et al., "New Fluorescent Derivatives of Cyclosporin for Use in Immunoassays," *Journal of Pharmaceutical and Biomedical Analysis* 10(1):23-30 (1992), Abstract only.

Galpin et al., "Synthesis of Cyclosporin Analogs," *Tetrahedron Letters* 28(51):6517-6520 (1987), Abstract only.

Galpin et al., "Synthetic Studies of Cyclosporin Analogs," *Tetrahedron* 44(6):1783-1794 (1988), Abstract only.

Gfeller et al., "Improvement of Detection Sensitivity of Cyclosporin A by Derivatization With 2-Naphthylselenyl Chloride," *Helvetica Chimica Acta* 63(3):728-732 (1980), Abstract only.

Giger et al., "Design and Synthesis of a Transition State Analog of a Metalloporphyrin-Catalysed Oxidation Reaction," *Journal of Porphyrins and Phthalocyanines* 6(5):362-365 (2002), Abstract only.

Grote et al. "A Practical Method for the Synthesis of a Cyclosporine-Fluorescein Conjugate," *Organic Process Research & Development*, 9(6):822-824 (2005), Abstract only.

Guichou et al., "Pseudo-Prolines (ΨPro): Direct Insertion of ΨPro Systems Into Cysteine Containing Peptides," *Tetrahedron Letters* 43(24):4389-4390 (2002), Abstract only.

Hamel et al., "Cyclosporin A Prodrugs: Design, Synthesis and Biophysical Properties," *Journal of Peptide Research* 63(2):147-154 (2004), Abstract only.

Hamel et al., "Water-Soluble Prodrugs of Cyclosporine A With Tailored Conversion Rates," *Journal of Peptide Research* 65(3):364-374 (2005), Abstract only.

Hensens et al., "The Preparation of [2-deutero-3-fluoro-D-Ala8]Cyclosporin A by Directed Biosynthesis," *Journal of Antibiotics* 45(1):133-135 (1992), Abstract only.

Hornich et al., "Variation of Amino Acids Within the Cyclosporine-Cyclophilin Binding Domain. Synthesis of a 21-Membered Cyclopeptolide," *Scientia Pharmaceutica* 64(3/4):463-470 (1996), Abstract only.

Hu et al., "Cyclosporin Analogs Modified in the 3,7,8-Positions: Substituent Effects on Peptidylprolyl Isomerase Inhibition and Immunosuppressive Activity Are Nonadditive," *Journal of Medicinal Chemistry* 38(21):4164-4170 (1995), Abstract only.

Hu, "Synthesis And Biological Properties Of Novel Cyclosporine Analogs," Diss. Abstr. Int. B 1995, 55(7), 2743 (1994), Abstract only.

Hubler et al., "Synthetic Routes to NEtXaa4-Cyclosporin A Derivatives as Potential Anti-HIV 1 Drugs," *Tetrahedron Letters* 41(37):7193-7196 (2000), Abstract only.

Husi et al., "Prediction of Substrate-Specific Pockets in Cyclosporin Synthetase," *FEBS Letters* 414(3):532-536 (1997), Abstract only.

Jegorov et al., "An Unusual Side Chain C-C Cleavage at the MeBmt Amino Acid in Cyclosporin A," *Amino Acids* 10(2):145-151 (1996), Abstract only.

Jegorov et al., "Cyclosporins from *Tolypocladium terricola*," *Phytochemistry* 38(2):403-407 (1995), Abstract only.

Jegorov et al., "Cyclosporins of Symmetry P21—a Series of Clathrates," *Journal of Inclusion Phenomena and Macrocyclic Chemistry* 37(1-4):137-153 (2000), Abstract only.

Jegorov et al., "Synthesis and Crystal Structure Determination of Cyclosporin H," *Collection of Czechoslovak Chemical Communications* 65(8):1317-1329 (2000), Abstract only.

Jiang et al., "Synthesis of Biotinylated Cyclosporin A and Studies on its Interaction With Human Cyclophilin A," *Huaxue Xuebao* 59(10):1745-1750 (2001), Abstract only.

Kanoh et al., Photo-Cross-Linked Small-Molecule Affinity Matrix for Facilitating Forward and Reverse Chemical Genetics *Angewandte Chemie, International Edition* 44(28):4282 (2005) [Erratum], Abstract only.

Kanoh et al., Photo-Cross-Linked Small-Molecule Affinity Matrix for Facilitating Forward and Reverse Chemical Genetics *Angewandte Chemie, International Edition* 44(23):3559-3562 (2005), Abstract only.

Keller et al., "Pseudoprolines (ΨPro) in Drug Design: Direct Insertion of ΨPro Systems Into Cyclosporin C," *Chemistry—A European Journal* 6(23):4358-4363 (2000), Abstract only.

Kobel et al., "Directed Biosynthesis of Cyclosporins," *European Journal of Applied Microbiology and Biotechnology* 14(4):237-240 (1982), Abstract only.

Koeck et al., "Novel Backbone Conformation of Cyclosporin A: The Complex With Lithium Chloride," *Journal of the American Chemical Society* 114(7):2676-2686 (1992), Abstract only.

Kratochvil et al., "Crystal Structures of Cyclosporin Derivatives: O-acetyl-(4R)-4-(E-2-butyl)-4,N-Dimethyl-L-Threonyl-Cyclosporin A and O-Acetyl-(4R)-4-[E-2-(4-Bromobutyl)]-4,N-Dimethyl-L-Threonyl-Cyclosporin A," *Collection of Czechoslovak Chemical Communications* 64(1):89-98 (1999), Abstract only.

Kuhnt et al., "Microbial Biotransformation Products of Cyclosporin A," *Journal of Antibiotics* 49(8):781-787 (1996), Abstract only.

Lee et al., "Synthesis and Immunosuppressive Activities of Conformationally Restricted Cyclosporin Lactam Analogs," *International Journal of Peptide & Protein Research* 35(5):481-494 (1990), Abstract only.

Levitsky et al., "Exo-Mechanism Proximity-Accelerated Alkylations: Investigations of Linkers, Electrophiles and Surface Mutations in Engineered Cyclophilin-Cyclosporin Systems," *ChemBioChem* 6(5):890-899 (2005), Abstract only.

Levitsky et al., "Selective Inhibition of Engineered Receptors Via Proximity-Accelerated Alkylation," *Organic Letters* 5(5):693-696 (2003), Abstract only.

Lhoest et al., "Isolation, Identification and Immunosuppressive Activity of a New IMM-125 Metabolite From Human Liver Microsomes. Identification of its Cyclophilin A-IMM-125 Metabolite Complex by Nanospray Tandem Mass Spectrometry," *Journal of Mass Spectrometry* 33(10):936-942 (1998), Abstract only.

Li et al., "The Development of Highly Efficient Onium-Type Peptide Coupling Reagents Based Upon Rational Molecular Design," *Journal of Peptide Research* 58(2):129-139 (2001), Abstract only.

Li et al., "Total Synthesis of Cyclosporin O Both in Solution and in the Solid Phase Using Novel Thiazolium-, Immonium-, and Pyridinium-Type Coupling Reagents: BEMT, BDMP, and BEP," *Journal of Organic Chemistry* 65(10):2951-2958 (2000), Abstract only.

Liu et al., "Preparation of Cyclosporine A Immunogen," *Sichuan Daxue Xuebao, Ziran Kexueban* 38(3):407-411 (2001), Abstract only.

Liu et al., "Semipreparative Chromatographic Separation Of Cyclosporin G Metabolites Generated by Microsomes from Rabbits Treated With Rifampicin," *Journal of Pharmacological and Toxicological Methods* 35(3):121-129 (1996), Abstract only.

Liu et al., "Structural Characterization of two Novel Oxidative Derivatives of Cyclosporine Generated by a Chemical Method," *Clinical Biochemistry* 31(3):173-180 (1998), Abstract only.

Lu et al., "Modification of Cyclosporin A and Conjugation of Its Derivative to HPMA Copolymers," *Bioconjugate Chemistry* 12(1):129-133 (2001), Abstract only.

Lu et al., "Synthesis of Bioadhesive Lectin-HPMA Copolymer-Cyclosporin Conjugates," *Bioconjugate Chemistry* 11(1):3-7 (2000), Abstract only.

Lynch, "The Search For Cyclophilin Inhibitors: The Design And Synthesis Of Conformationally Constrained Scaffolds," Diss. Abstr. Int., B 1995, 56(2)828 (1995), Abstract only.

Magni et al., "Hydrolytic Conditions for the Formation of Open-Chain Oligopeptides from Cyclosporin A," *Journal of Peptide Research* 49(3):191-194 (1997), Abstract only.

Mahoney et al., "Derivatives of Cyclsporin Compatible With Antibody-Based Assays: I. The Generation of [125I]-Labeled Cyclosporin," *Clinical Chemistry* (Washington, DC, United States), 31(3):459-462 (1985), Abstract only.

McIntyre et al., "ISA-247," *Drugs of the Future* 29(7):680-686 (2004), Abstract only.

Mikol et al., "The Role of Water Molecules in the Structure-Based Design of (5-Hydroxynorvaline)-2-cyclosporin: Synthesis, Biological Activity, and Crystallographic Analysis with Cyclophilin A," *Journal of Medicinal Chemistry* 38(17):3361-3367 (1995), Abstract only.

Muamba et al. "Peptides: The Wave of the Future," in Lebl eds., *Proceedings of the Second International and the Seventeenth American Peptide Symposium*, San Diego, CA, Jun. 9-14, 2001, 130-131 (2001), Abstract only.

Ohta et al., "Production of Human Metabolites of Cyclosporin A, AM1, AM4N and AM9, by Microbial Conversion," *Journal of Bioscience and Bioengineering* 99(4):390-395 (2005), Abstract only.

Okada et al., "Properties and the Inclusion Behavior of 6-O-α-D-Galactosyl- and 6-O-α-D-Mannosyl- Cyclodextrins," *Chemical & Pharmaceutical Bulletin* 47(11):1564-1568 (1999), Abstract only.

Papageorgiou et al., "Anti HIV-1 Activity of Hydrophilic Cyclosporine Derivative With Improved Affinity to Cyclophilin," *Bioorganic & Medicinal Chemistry Letters* 6(4):497 (1996) [Erratum], Abstract only.

Papageorgiou et al., "Anti HIV-1 Activity of a Hydrophilic Cyclosporine Derivative With Improved Binding Affinity to Cyclophilin A," *Bioorganic & Medicinal Chemistry Letters* 6(1):23-26 (1996), Abstract only.

Papageorgiou et al., "Calcineurin has a Very Tight-Binding Pocket for the Side Chain of Residue 4 of Cyclosporin," *Bioorganic & Medicinal Chemistry Letters* 4(2):267-272 (1994), Abstract only.

Papageorgiou et al., "Conformational Control of Cyclosporin Through Substitution of the N-5 position. A new class of cyclosporin antagonists," *Bioorganic & Medicinal Chemistry* 5(1):187-192 (1997), Abstract only.

Papageorgiou et al., "Derivatives of Cyclosporin at Position 2 as Probes for Cyclophilin," *Bioorganic & Medicinal Chemistry Letters* 3(12):2559-64 (1993), Abstract only.

Papageorgiou et al., "Improved Binding Affinity for Cyclophilin A by a Cyclosporin Derivative Singly Modified at Its Effector Domain," *Journal of Medicinal Chemistry* 37(22):3674-3676 (1994), Abstract only.

Paprica et al., "Preparation of Novel Cyclosporin A Derivatives," *Bioconjugate Chemistry* 3(1):32-36 (1992), Abstract only.

Patchett et al., "Analogs of Cyclosporin A Modified at the D-Ala8 Position," *Journal of Antibiotics* 45(1):94-102 (1992), Abstract only.

Patiny et al., "Structure-Activity Studies of Novel D-Ser8-Cyclosporin A Derivatives As Potential Anti-HIV Drugs," *Peptides 2002, Proceedings of the European Peptide Symposium, 27th*, Benedetti et al. (eds) 1020-1021 (2002), Abstract only.

Patiny et al., "Synthesis and Characterization of Constrained Cyclosporin A Derivatives Containing a Pseudo-Proline Group," *Tetrahedron* 59(28):5241-5249 (2003), Abstract only.

Pflanz et al., "Induction and Rapid Screening of Monoclonal Antibodies Against Cyclosporin A," *Immunology Letters*, 18(4):241-245 (1988), Abstract only.

Pohl et al., "Crystal Structures of Two Modifications of [3,O-Didehydro-MeBmt1,Val2]Cyclosporin and Comparison of Three Different X-Ray Data Sets," *Helvetica Chimica Acta* 78(2):355-366 (1995), Abstract only.

Radeke et al., "Additive and Synergistic Effects of Cyclosporine Metabolites on Glomerular Mesangial Cells," *Kidney International* 39(6):1255-1266 (1991), Abstract only.

Raman Dissertation, 338 pp. Avail.: UMI, Order No. DA9809876 From: Diss. Abstr. Int., B 1998, 59(3), 1117 (1997), Abstract only.

Raman et al., "Methods to Circumvent a Difficult Coupling in the Solid-Phase Synthesis of Cyclosporine Analogs," *Journal of Organic Chemistry* 63(17):5734-5735 (1998), Abstract only.

Rich et al., "Synthesis and Antimitogenic Activities of Four Analogs of Cyclosporin A Modified in the 1-Position," *Journal of Medicinal Chemistry* 29(6):978-984 (1986), Abstract only.

Rich et al., "Synthesis, Biological Activity, and Conformational Analysis of (2S,3R,4S)-MeBmt-Cyclosporin, A Novel 1-Position Epimer of Cyclosporin A," *Journal of Medicinal Chemistry* 32(8):1982-1987 (1989), Abstract only.

Rihova et al., "Cytotoxic and Cytostatic Effects of Anti-Thy 1.2 Targeted Doxorubicin and Cyclosporin A," *Journal of Controlled Release* 40(3):303-319 (1996), Abstract only.

Roedl et al., "Lipoprotein-Induced Modulation of Cyclosporine A-Mediated Immunosuppression," *European Journal of Clinical Investigation* 20(3):248-252 (1990), Abstract only.

Romanova et al., "Synthesis of Cyclosporin A Fragment 8-11," *Ukrainskii Khimicheskii Zhurnal (Russian Edition)* 55(5):527-530 (1989), Abstract only.

Rothbard et al., "Conjugation of Arginine Oligomers to Cyclosporin A Facilitates Topical Delivery and Inhibition of Inflammation," *Nature Medicine* New York 6(11):1253-1257 (2000), Abstract only.

Rothe et al., in Brunfeldt, ed., *Pept., Proc. Eur. Pept. Symp.*, 16th Meeting Date 1980, Scriptor: Copenhagen, Den pp. 258-263 (1981), Abstract only.

Rozycki et al., "New Cyclosporin A Analog: Synthesis and Immunosuppressive Activity," *Molecular Immunology* 29(9):1043-1047 (1992), Abstract only.

Ruegger et al., "Cyclosporin A, A Peptide Metabolite From *Trichoderma polysporum* (Link ex Pers.) Rifai, With Immunosuppressive Activity," *Helvetica Chimica Acta* 59(4):1075-1092 (1976), Abstract only.

Sakamoto et al., "FR901459, a Novel Immunosuppressant Isolated From *Stachybotrys chartarum* No. 19392. Taxonomy of the Producing Organism, Fermentation, Isolation, Physico-Chemical Properties and Biological Activities," *Journal of Antibiotics* 46(12):1788-1798 (1993), Abstract only.

Shevchenko et al., "Synthesis of Tritiated Cyclosporin A and FK-506 by Metal-Catalyzed Hydrogen Isotope Exchange," *Journal of Labelled Compounds & Radiopharmaceuticals* 47(7):407-414 (2004), Abstract only.

Shevchenko et al., Synthesis of Tritium-Labeled Immunodepressants Containing Double Bonds by Isotope Exchange with Tritium Water, *Radiochemistry* (Moscow) (*Translation of Radiokhimiya*) 41(1):85-88 (1999), Abstract only.

Smulik et al., "Synthesis of Cyclosporin A-Derived Affinity Reagents by Olefin Metathesis," *Organic Letters* 4(12):2051-2054 (2002), Abstract only.

Stabler et al., "Chemiluminescence Immunoassay of Cyclosporine in Whole Blood," *Clinical Chemistry* (Washington, DC, United States), 36(6):906-908 (1990), Abstract only.

Sun et al., "Synthesis, Conformation, and Immunosuppressive Activity of Cyclosporines That Contain $\epsilon$-Oxygen (4R)-4-[(E)-butenyl]-4,N-Dimethyl-L-Threonine Analogs in the 1-Position," *Journal of Medicinal Chemistry* 33(5):1443-1452 (1990), Abstract only.

Sun, "Synthesis Of Cyclosporin Analogs Modified in the 1-Position," Diss. Abstr. Int. B 1990, 50(12, Pt. 1), 5637 (1989), Abstract only.

Tamolang et al., "A Rifampicin-Induced Hepatic Microsomal Enzyme System for the Generation of Cyclosporine Metabolites," *Pharmacological Research* 32(3):141-148 (1995), Abstract only.

Thern et al., "Peptides: The Wave of the Future," in Lebl, eds., *Proceedings of the Second International and the Seventh American Peptide Symposium*, San Diego, CA, Jun. 9-14, 2001, 244-245 (2001), Abstract only.

Thern et al., "Triphosgene as Highly Efficient Reagent for the Solid-Phase Coupling of N-Alkylated Amino Acids-Total Synthesis of Cyclosporin O," *Tetrahedron Letters* 43(28):5013-5016 (2002), Abstract only.

Traber et al., "[Melle4]Cyclosporin, a Novel Natural Cyclosporin With Anti-HIV Activity: Structural Elucidation, Biosynthesis and Biological Properties," *Antiviral Chemistry & Chemotherapy* 5(5):331-339 (1994), Abstract only.

Traber et al., "New Cyclopeptides From *Trichoderma polysporum* (Link ex Pers.) Rifai: Cyclosporins B, D and E," *Helvetica Chimica Acta* 60(5):1568-1578 (1977), Abstract only.

Traber et al., "Novel Cyclosporins from *Tolypocladium inflatum*. Cyclosporins K-Z," *Helvetica Chimica Acta* 70(1):13-36 (1987), Abstract only.

Traber et al., "Occurrence of Cyclosporins and Cyclosporin-Like Peptolides in Fungi," *Journal of Industrial Microbiology & Biotechnology* 17(5/6):397-401 (1996), Abstract only.

Traber et al., "The Structure of Cyclosporin C," *Helvetica Chimica Acta* 60(4):1247-1255 (1977), Abstract only.

Tung et al., "Synthesis and Biological Properties of a High Specific Activity Radioiodinated, Photolabile Cyclosporin," *UCLA Symposia on Molecular and Cellular Biology, New Series*, 86(Synth. Pept.), pp. 321-335 (1989), Abstract only.

Tuominen et al., "Separation of Cyclosporins by High-Performance Liquid Chromatography and Mass Spectrometric Study of Cyclosporin Metabolites," *Rapid Communications in Mass Spectrometry* 12(16):1085-1091 (1998), Abstract only.

Vedejs et al., "Solution-Phase Synthesis of a Hindered N-Methylated Tetrapeptide Using Bts-Protected Amino Acid Chlorides: Efficient Coupling and Methylation Steps Allow Purification by Extraction," *Journal of Organic Chemistry* 65(8):2309-2318 (2000), Abstract only.

Wei et al., "Synthesis and Neurotrophic Activity of Nonimmunosuppressant Cyclosporin A Derivatives," *Bioorganic & Medicinal Chemistry Letters* 14(17):4549-4551 (2004), Abstract only.

Wenger et al., "Cyclosporine: Chemistry, Structure-Activity Relationships and Mode of Action," *Progress in Clinical Biochemistry and Medicine* 3:157-191 (1986), Abstract only.

Wenger et al., "Structure of Cyclosporine and its Metabolites: Total Synthesis of Cyclosporine Metabolites Formed by Oxidation at Positions 4 and 9 of Cyclosporine. Preparation of Leucine-4-(γ-hydroxy)-N-Methylleucine-9-Cyclosporine," *Chimica* 46(7-8):314-322 C (1992), Abstract only.

Wenger, "Synthesis of Ciclosporin and Analogs: Structural and Conformational Requirements for Immunosuppressive Activity," *Progress in Allergy* 38(Ciclosporin):46-64 (1986), Abstract only.

Wenger, "Synthesis of Cyclosporin and Analogs: Structure, Activity, Relationships of New Cyclosporin Derivatives," *Transplantation Proceedings* 15(4, Suppl. 1-2)2230-2241 (1983), Abstract only.

Wu et al., "Preparation of Cyclosporin A Immunogen," *Journal of Chinese Pharmaceutical Sciences* 11(3):78-82 (2002), Abstract only.

Yamada et al., "Single-Step N-Methylation of Hindered Peptides: Total Synthesis of Cyclosporin O," *Peptide Science* 41:591-594 vol. Date, 2004, (2005), Abstract only.

* cited by examiner

CYCLOSPORIN ALKYNES AND THEIR UTILITY AS PHARMACEUTICAL AGENTS

This application claims the benefit of U.S. Provisional Patent Application Ser. No. 60/616,591, filed Oct. 6, 2004, which is hereby incorporated by reference in its entirety.

FIELD OF THE INVENTION

The present invention discloses novel cyclosporin alkynes and their utility as immunosuppressive agents and pharmaceutical agents for treatment of other diseases. Methods for preparation of such compounds are also disclosed.

BACKGROUND OF THE INVENTION

Cyclosporin A (CsA), a neutral cyclic undecapeptide isolated from the fungus *Tolypocladium inflatum* and currently marketed as Neoral® and Sandimmune® (Novartis, Basel, Switzerland), has been widely used for the prevention of organ transplant rejection. Cyclosporin A exerts its immunosuppressive effect at the molecular level by binding to the cyclophilin peptidyprolyl cis/trans isomerase. The resulting complex of cyclosporin A and cyclophilin binds to calcineurin, a $Ca^{2+}$/calmodulin-dependent phosphatase, and inhibits its phosphatase activity. Calcineurin regulates the translocation of the transcription factor nuclear factor of activated T-cell (NFAT) and the subsequent expression of early genes necessary for T-cell proliferation. Inhibition of the phosphatase activity of calcineurin by the cyclosporin A-cyclophilin complex prevents NFAT nuclear localization and suppresses the expression of genes like IL-2, ultimately leading to immunosuppression (Matsuda et al., "Mechanisms of Action of Cyclosporin," *Immunopharmacology*, 47:119-125 (2000)).

Cyclosporin A also has potential therapeutic application in the treatment of autoimmune diseases such as rheumatoid arthritis, Crohn's disease, psoriasis, and chronic inflammatory diseases, such as asthma. Unfortunately, clinical utility for these indications has not been realized because of the side effects such as nephrotoxicity, hypertension, hepatotoxicity, anaemia, and gastrointestinal intolerance that occur with clinically effective doses of cyclosporin A. The toxicity associated with cyclosporin A is believed by many experts working in the immunosuppression therapeutic area to be mechanism based (Lazarova et al., "Cyclosporin A Analogues: Recent Advances," *Expert Opin. Ther. Patents*, 13:1327-1332 (2003)). Indeed, the goal of discovering novel cyclosporin analogues with improved therapeutic index has yet to be achieved despite the significant efforts in this drug discovery area over the last three decades (U.S. Pat. No. 5,525,590 to Bollinger et al.; U.S. Pat. No. 5,643,870 to Boelsterli et al.; U.S. Pat. No. 5,639,852 to Rich et al.; U.S. Pat. No. 5,236,899 to Durette; U.S. Pat. No. 5,122,511 to Patchett et al.; U.S. Pat. No. 4,914,188 to Dumont et al.; U.S. Pat. No. 4,771,122 to Seebach; U.S. Pat. No. 4,764,503 to Wenger; U.S. Pat. No. 4,396,542 to Wenger; U.S. Pat. No. 4,210,581 to Ruegger et al.).

More recent efforts to find novel cyclosporin analogues with potent immunosuppressive activity and decreased toxicity are underway and have led to compounds such as $ISA_{TX}247$. Preclinical observations indicate that $ISA_{TX}247$ has the potential to be significantly more potent and less toxic than other immunosuppressants in its class already available on the market for the prevention of transplant rejection. $ISA_{TX}247$ is in phase II clinical trials for the prevention of organ rejection after transplantation and for the treatment of psoriasis (Abel et al., "$ISA_{TX}247$: A Novel Calcineurin Inhibitor," *J. Heart Lung Transplant*, 20:161 (2001); Aspeslet et al., "$ISA_{TX}247$: A Novel Calcineurin Inhibitor," *Transplantation Proceedings*, 33:1048-1051 (2001); U.S. Pat. Nos. 6,605,593 and 6,613,739 to Naicker et al.).

A "soft" drug approach (Lazarova et al., "Synthesis and Biological Evaluation of Cyclosporin A Analogues: Potential Soft Drugs for the Treatment of Autoimmune Diseases," *J. Med. Chem.*, 46:674-676 (2003)) has also recently been described that seeks to minimize the toxicity of immunosuppressive cyclosporin A derivatives used for the treatment of autoimmune diseases (PCT International Patent Publication No. WO 03/033010 to Or et al.) and respiratory diseases, such as asthma (PCT International Patent Publication No. WO 02/069902 to Or et al.).

There is still a large need for novel cyclosporin analogues with improved therapeutic index.

The present invention is directed to achieving these objectives.

SUMMARY OF THE INVENTION

The compounds of the present invention are represented by Formula I, as shown below:

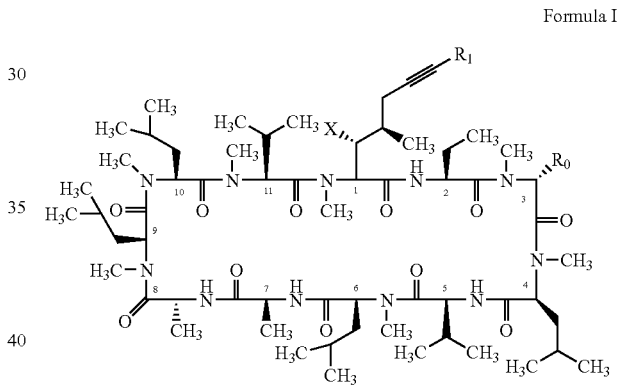

Formula I where:
X is OH or OAc;
$R_0$ is H, $CH_2OH$, or $CH_2OR_2$;
$R_1$ is selected from the group consisting of:
  hydrogen;
  halogen;
  $C_2$-$C_6$ saturated or unsaturated, straight or branched carbon chain;
  $C_2$-$C_6$ saturated or unsaturated, straight or branched carbon chain containing substitution or substitutions selected from the group consisting of deuterium, halogen, nitrogen, sulfur, and silicon atom or atoms;
  $C_2$-$C_6$ saturated or unsaturated, straight or branched carbon chain containing a function group or function groups selected from the group consisting of alcohol, ether, aldehyde, ketone, carboxylic ester, and amide;
  $C_2$-$C_4$ saturated or unsaturated, straight or branched carbon chain containing an aryl or a heteroaryl;
  $C_3$-$C_6$-substituted and unsubstituted cycloalkyl;
  substituted and unsubstituted aryl;
  substituted and unsubstituted heteroaryl;
  —$CH_2OH$;
  —CHO;

—CH=N—OR$_3$; and
—CH=N—NR$_3$R$_4$;
R$_2$ is selected from the group consisting of:
  alkanoyl;
  alkenoyl;
  alkynoyl;
  aryloyl;
  arylalkanoyl;
  alkylaminocarbonyl;
  arylaminocarbonyl;
  arylalkylaminocarbonyl;
  alkyloxycarbonyl;
  aryloxycarbonyl; and
  arylalkyloxycarbonyl;
R$_3$ or R$_4$ are the same or different and independently selected from the group consisting of:
  hydrogen;
  C$_1$-C$_6$ saturated straight or branched carbon chain;
  C$_3$-C$_6$ unsaturated straight or branched carbon chain;
  C$_3$-C$_6$-substituted and unsubstituted cycloalkyl;
  C$_1$-C$_4$ carbon chain containing an aryl or heteroaryl;
  substituted and unsubstituted aryl;
  substituted and unsubstituted heteroaryl;
  alkanoyl;
  alkenoyl;
  alkynoyl;
  aryloyl;
  arylalkanoyl;
  alkylaminocarbonyl;
  arylaminocarbonyl;
  arylalkylaminocarbonyl;
  alkyloxycarbonyl;
  aryloxycarbonyl; and
  arylalkyloxycarbonyl; and
R$_3$ together with R$_4$ results in the formation of a cyclic moiety of C$_2$-C$_6$ optionally containing heteroatom or heteroatoms,
or a pharmaceutically acceptable salt thereof.

The present invention discloses chemically modified cyclosporin analogues containing a carbon-carbon triple bond on the side chain of the position one amino acid and optionally a substitution on the position three amino acid of cyclosporin A. In particular, the present invention discloses novel cyclosporin alkyne analogues containing a conjugated system of a carbon-carbon triple bond with an aryl, a carbon-carbon double bond, a carbon-nitrogen double bond, or another carbon-carbon triple bond.

The present invention provides novel cyclosporin analogues which are effective as immunosuppressive agents. Some compounds of the present invention possess enhanced immunosuppressive activity over cyclosporin A. These compounds also possess utility in the treatment of ocular allergy and dry eye, as well as autoimmune and chronic inflammatory diseases, such as asthma, rheumatoid arthritis, multiple sclerosis, psoriasis, and ulcerative colitis.

DETAILED DESCRIPTION OF THE INVENTION

Figure 1:
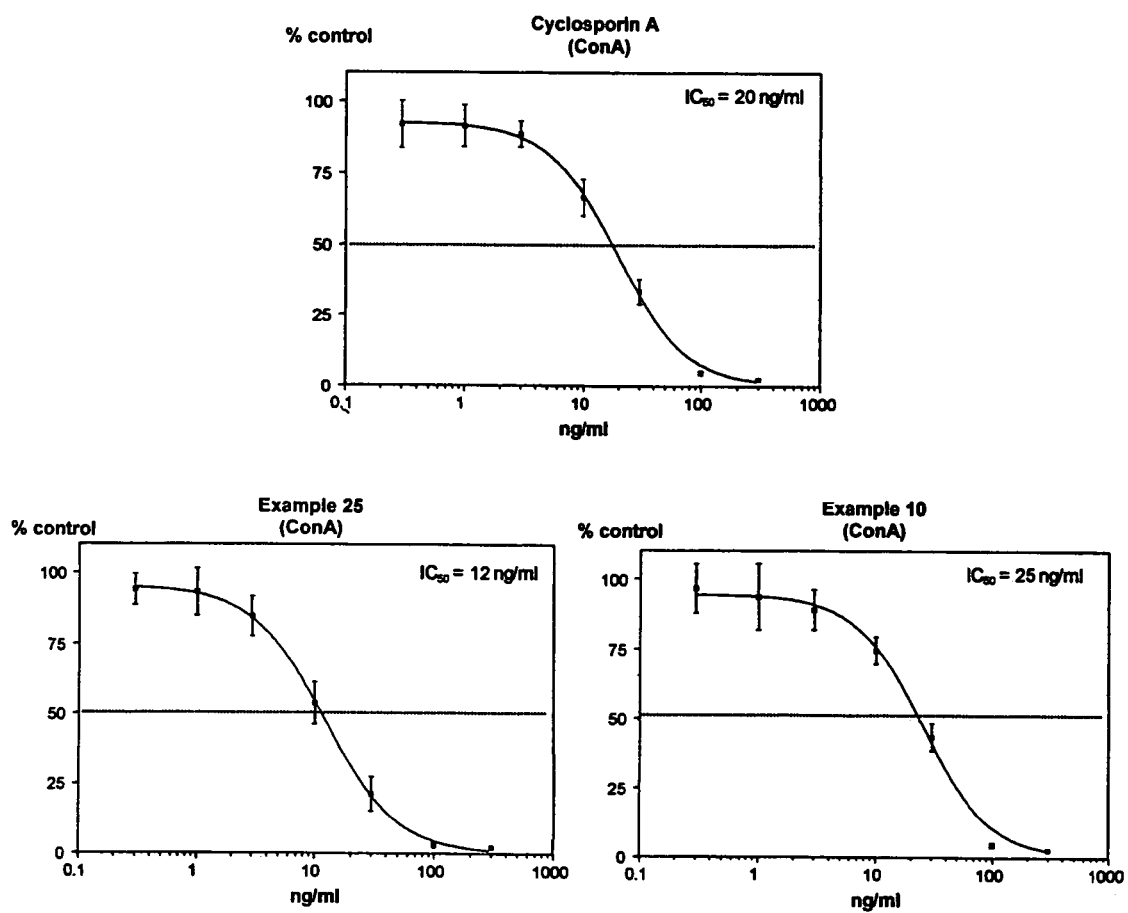
FIG. 1 depicts the results from a concanavalin A (ConA)-stimulated murine splenocyte assay, where the novel cyclosporin analogue compounds of the present invention (disclosed in Examples 25 and 10) are shown to possess enhanced or similar potency in immunosuppression, compared to cyclosporin A.

The compounds of the present invention are represented by Formula I, as shown below:

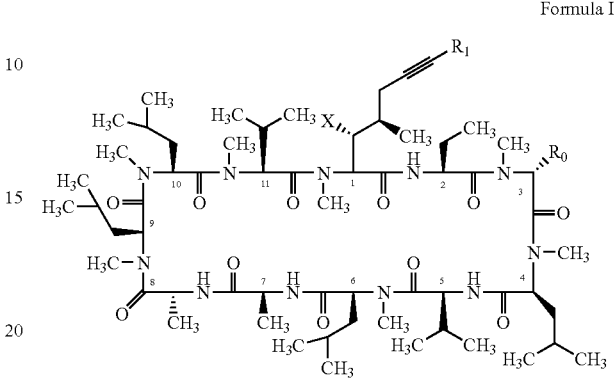

Formula I where:
X is OH or OAc;
R$_0$ is H, CH$_2$OH, or CH$_2$OR$_2$;
R$_1$ is selected from the group consisting of:
  hydrogen;
  halogen;
  C$_2$-C$_6$ saturated or unsaturated, straight or branched carbon chain;
  C$_2$-C$_6$ saturated or unsaturated, straight or branched carbon chain containing substitution or substitutions selected from the group consisting of deuterium, halogen, nitrogen, sulfur, and silicon atom or atoms;
  C$_2$-C$_6$ saturated or unsaturated, straight or branched carbon chain containing a function group or function groups selected from the group consisting of alcohol, ether, aldehyde, ketone, carboxylic ester, and amide;
  C$_2$-C$_4$ saturated or unsaturated, straight or branched carbon chain containing an aryl or a heteroaryl;
  C$_3$-C$_6$-substituted and unsubstituted cycloalkyl;
  substituted and unsubstituted aryl;
  substituted and unsubstituted heteroaryl;
  —CH$_2$OH;
  —CHO;
  —CH=N—OR$_3$; and
  —CH=N—NR$_3$R$_4$;
R$_2$ is selected from the group consisting of:
  alkanoyl;
  alkenoyl;
  alkynoyl;
  aryloyl;
  arylalkanoyl;
  alkylaminocarbonyl;
  arylaminocarbonyl;
  arylalkylaminocarbonyl;
  alkyloxycarbonyl;
  aryloxycarbonyl; and
  arylalkyloxycarbonyl;
R$_3$ or R$_4$ are the same or different and independently selected from the group consisting of:
  hydrogen;
  C$_1$-C$_6$ saturated straight or branched carbon chain;
  C$_3$-C$_6$ unsaturated straight or branched carbon chain;
  C$_3$-C$_6$-substituted and unsubstituted cycloalkyl;

$C_1$-$C_4$ carbon chain containing an aryl or heteroaryl;
substituted and unsubstituted aryl;
substituted and unsubstituted heteroaryl;
alkanoyl;
alkenoyl;
alkynoyl;
aryloyl;
arylalkanoyl;
alkylaminocarbonyl;
arylaminocarbonyl;
arylalkylaminocarbonyl;
alkyloxycarbonyl;
aryloxycarbonyl; and
arylalkyloxycarbonyl; and $R_3$ together with $R_4$ results in the formation of a cyclic moiety of $C_2$-$C_6$ optionally containing heteroatom or heteroatoms, or a pharmaceutically acceptable salt thereof.

One embodiment of the present invention is the above compound of Formula I, where: X is OH or OAc; $R_0$ is H, $CH_2OH$, or $CH_2OAc$; and $R_1$ is H.

Another embodiment of the present invention is the above compound of Formula I, where: X is OH or OAc; $R_0$ is H, $CH_2OH$, or $CH_2OAc$; and $R_1$ is selected from the group consisting of F, Cl, Br, and I.

Another embodiment of the present invention is the above compound of Formula I, where: X is OH or OAc; $R_0$ is H, $CH_2OH$, or $CH_2OAc$; and $R_1$ is selected from the group consisting of CH=$CH_2$, CH=$CHCH_3$, CH=$CHCH_2CH_3$, C($CH_3$)=$CH_2$, CH=$CD_2$, CH=$CHCD_3$, and CH=$CDCD_3$, and where the carbon-carbon double bond is a cis or a trans geometric isomer or a mixture of both cis and trans geometric isomers.

Another embodiment of the present invention is the above compound of Formula I, where: X is OH or OAc; $R_0$ is H, $CH_2OH$, or $CH_2OAc$; and $R_1$ is selected from the group consisting of CH=CHF, CH=CHCl, CH=CHBr, CH=CHI, CH=$CF_2$, and CH=$CCl_2$, and where the carbon-carbon double bond is a cis or a trans geometric isomer or a mixture of both cis and trans geometric isomers.

Another embodiment of the present invention is the above compound of Formula I, where: X is OH or OAc; $R_0$ is H, $CH_2OH$, or $CH_2OAc$; and $R_1$ is selected from the group consisting of C≡CH, C≡$CCH_3$, C≡$CCD_3$, C≡$CCH_2CH_3$, C≡$CCH_2CH_2CH_3$, and C≡C-cyclopropyl.

Another embodiment of the present invention is the above compound of Formula I, where: X is OH or OAc; $R_0$ is H, $CH_2OH$, or $CH_2OAc$; and $R_1$ is selected from the group consisting of $CH_2$C≡CH, $CH_2$C≡$CCH_3$, $CH_2$C≡$CCH_2CH_3$, $CH_2$CH=$CH_2$, $CH_2$CH=$CHCH_3$, and $CH_2$CH=$CHCH_2CH_3$ and where the carbon-carbon double bond is a cis or a trans geometric isomer or a mixture of both cis and trans geometric isomers Another embodiment of the present invention is the above compound of Formula I, where: X is OH or OAc; $R_0$ is H, $CH_2OH$, or $CH_2OAc$; and $R_1$ is selected from the group consisting of C≡C—C≡CH, C≡C—C≡$CCH_3$, C≡CCH=$CH_2$, C≡CCH=$CHCH_3$, CH=CHC≡CH, CH=CHC≡$CCH_3$, CH=CHCH=$CH_2$, and CH=CHCH=$CHCH_3$ and where the carbon-carbon double bond is a cis or a trans geometric isomer or a mixture of both cis and trans geometric isomers Another embodiment of the present invention is the above compound of Formula I, where: X is OH or OAc; $R_0$ is H, $CH_2OH$, or $CH_2OAc$; and $R_1$ is cyclopropyl.

Another embodiment of the present invention is the above compound of Formula I, where: X is OH or OAc; $R_0$ is H, $CH_2OH$, or $CH_2OAc$; and $R_1$ is selected from the group consisting of $CH_2OH$, —CHO, CH(OH)$CH_3$, C(=O)$CH_3$, CH=N—$OCH_3$, CH=N—$OCH_2CH_3$, CH=N—$NHCH_3$, and CH=N—N($CH_3$)$_2$.

Other embodiments of the present invention include the above compound of Formula I, where: X=OH or OAc; $R_0$=H; and $R_1$ is selected from the group consisting of H, $C_6H_5$—, p-F$C_6H_4$—, p-$CH_3$O$C_6H_4$—, 2-thiophenyl, $CH_2$Ph, $CH_2$CH=$CH_2$, $CH_2$C≡CH, $CH_2$C≡$CCH_3$, $CH_2$C≡CHSi($CH_3$)$_3$, Br, $CH_2$Cl, CH=$CH_2$, CH=$CHCH_3$ (trans), CH=$CHCH_3$ (cis), CH=CHCl (trans), CH=CHCl (cis), CH=CHSi($CH_3$)$_3$ (trans), C($CH_3$)=$CH_2$, CH=CHPh, CH=CHCO$_2$Et (cis), CH=C=$CH_2$, C≡CH, C≡$CCH_3$, C≡$CCD_3$, C≡$CCH_2CH_3$, C≡$CC_4H_9$, C≡CSi($CH_3$)$_3$, C≡C-3-thiophene, C≡C-Ph, C≡CBr, C≡C-cyclopropyl, C≡C-cyclohexyl, C≡$CCH_2OH$, C≡$CCH_2OCH_3$, C≡$CCH_2SCH_2CH_3$, C≡$CCH_2N(CH_3)_2$, C≡CCH=$CH_2$, C≡CC($CH_3$)=$CH_2$, C≡CCH=$CHCH_3$ (cis), C≡CCH=$CHCH_3$ (trans), CH=CHC≡CH, CH=CHC≡$CCH_2CH_2CH_3$, CH=CHC≡C-cyclopropyl, $CH_2OH$, CHO, C=N—$OCH_3$, and C=N—N($CH_3$)$_2$.

Other embodiments of the present invention include the above compound of Formula I, where: X=OH or OAc; $R_0$=$CH_2OH$ or $CH_2OAc$; and $R_1$ is selected from the group consisting of H, CH=$CH_2$, CH=$CHCH_3$ (cis), CH=$CHCH_3$ (trans), and CH=CHCl (cis).

In particular, the present invention relates to novel cyclosporin analogues containing a carbon-carbon triple bond on the side chain of the position one amino acid and optionally a substitution on the position three amino acid of cyclosporin A. More particularly, the present invention relates to novel cyclosporin alkyne analogues, in which the carbon-carbon triple bond conjugating with an aryl, or a heteroaryl, or a carbon-carbon double bond, or a carbon-nitrogen double bond, or another carbon-carbon triple bond is incorporated.

A carbon-carbon triple bond exists in many natural products (Gung et al., "Total Synthesis of(S)-(–)-(E)-15,16-Dihydrominquartynoic Acid: A Highly Potent Anticancer Agent," *J. Org. Chem.*, 69:3488-3492 (2004); Ito et al., "Cytotoxic Polyacetylenes from the Twigs of *Ochanostachys amentacea*," *J. Nat. Prod.*, 64:246-248 (2001), which are hereby incorporated by reference in their entirety). It is well known to use alkynes as pharmaceutical agents. However, only one cyclosporin alkyne, in which a carbon-carbon triple bond replaces the carbon-carbon double bond on the side-chain of the position one amino acid of cyclosporin A, is known in the literature. Unfortunately, this modification significantly reduces the immunosuppressive activity of cyclosporin A, where this known cyclosporin alkyne shows only 10% relative immunosuppressive activity, compared to cyclosporin A (Rich et al., "Synthesis, Conformation, and Immunosuppressive Activities of Three Analogues of Cyclosporin A Modified in the 1-Position," *J. Med. Chem.*, 33:999-1009 (1990), which is hereby incorporated by reference in its entirety). In contrast, the novel cyclosporin alkyne analogues of the present invention, which contain a conjugated system of a carbon-carbon triple bond and a carbon-carbon double bond or a carbon-carbon triple bond, possess enhanced immunosuppressive activity over cyclosporin A.

The present invention also discloses methods for preparing compounds represented by Formula I.

The starting material for the preparation of the compounds of the present invention is cyclosporin A. The structure of cyclosporin A, a cycloundecapeptide, and the position numbering for each amino acid in the ring is shown below:

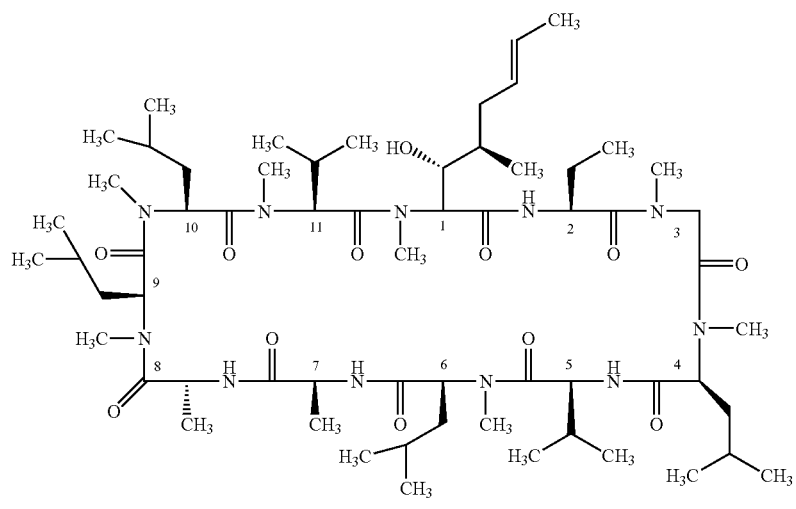

Cyclosporin A (CsA)

Cyclosporin A can also be represented by Formula Ia, as shown below:

Formula IIa

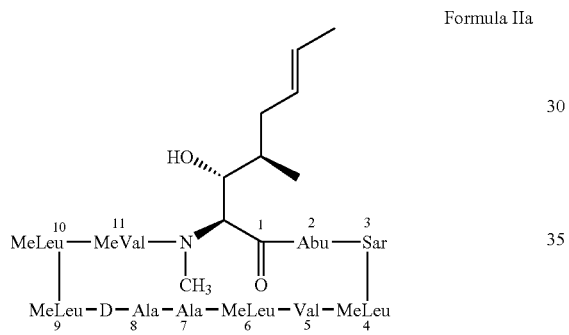

The novel cyclosporin analogues of the present invention are derived from cyclosporin A or cyclosporin diol (Formula IIb), a key intermediate prepared by modification on the position three amino acid of cyclosporin A. As shown in Scheme 1, the cyclosporin diol intermediate can be prepared by deprotonation of cyclosporin A with lithium diisopropylamide (LDA) followed by treatment with formaldehyde (Seebach et al, "Modification of Cyclosporin A: Generation of an Enolate at the Sarcosine Residue and Reaction with Electrophiles," *Helv. Chim. Acta*, 76:1564-1590 (1993), which is hereby incorporated by reference in its entirety).

Scheme 1

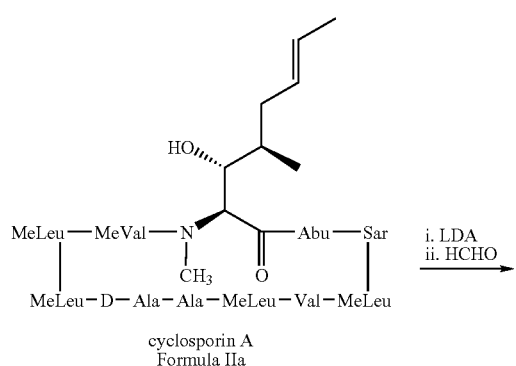

cyclosporin A
Formula IIa

-continued

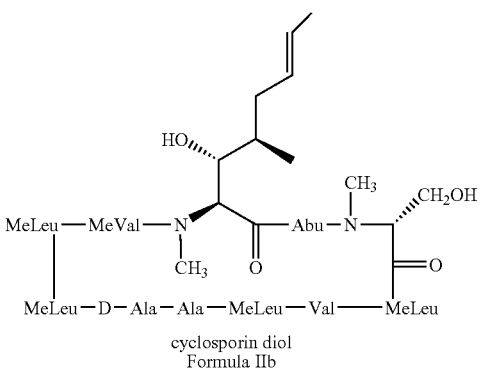

cyclosporin diol
Formula IIb

According to one embodiment of the present invention, novel cyclosporin analogues can be prepared by replacing the carbon-carbon double bond on the side chain of the position one amino acid of cyclosporin A with a carbon-carbon triple bond. As depicted in Scheme 2, acetylation of cyclosporin A (Formula IIa) or the cyclosporin diol intermediate of Formula IIb with acetic anhydride, followed by oxidative cleavage of the double bond with ozone, generates the cyclosporin aldehyde of Formula III smoothly. Treatment of the cyclosporin aldehyde of Formula III with dimethyl (1-diazo-2-oxopropyl)phosphonate in the presence of potassium carbonate in methanol provides cyclosporin alkyne (Formula I, X=OH) in good yield (Müller et al, An Improved One-Pot Procedure for the Synthesis of Alkynes from Aldehydes," *Synlett*, 521-522 (1996), which is hereby incorporated by reference in its entirety). The acetyl protecting group can be removed under these reaction conditions to give the free alcohol directly.

Scheme 2

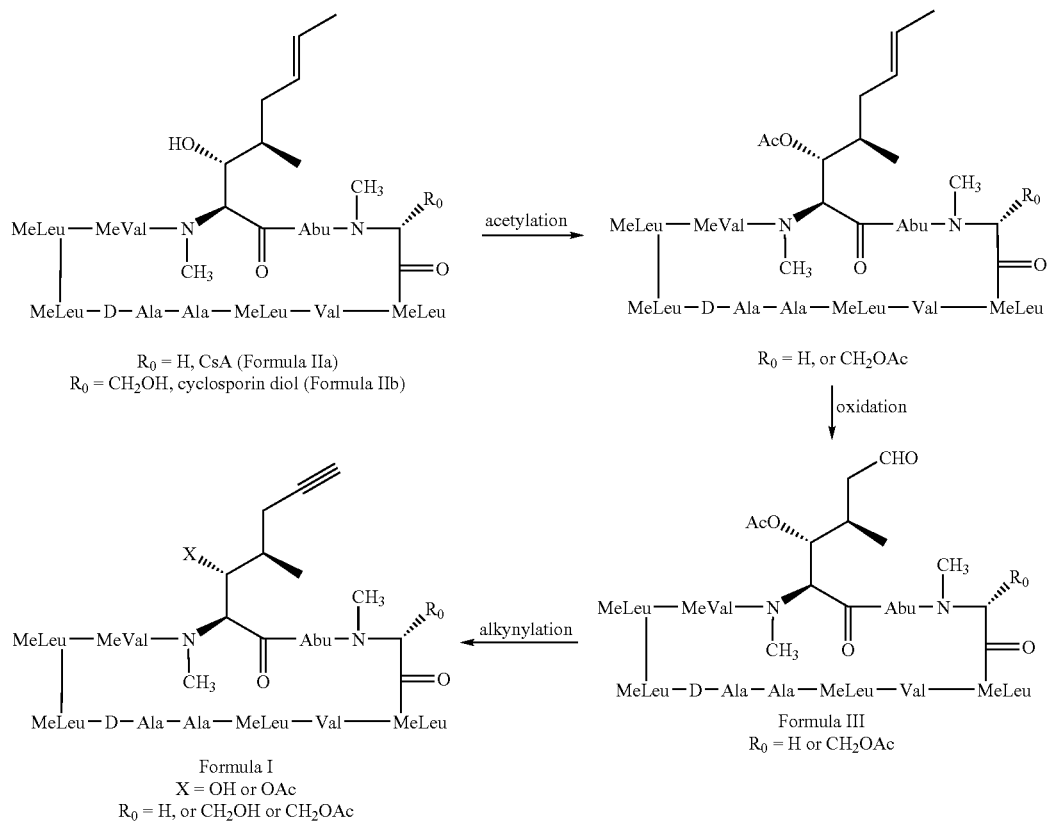

The cyclosporin aldehyde of Formula III can also be converted to the cyclosporin alkyne of Formula I (X=OH or OAc) via an alternate method (Scheme 2). Treatment of cyclosporin aldehyde with lithiotrimethylsilyldiazomethane affords the cyclosporin alkyne of Formula I (X=OH, $R_0$=H or $CH_2OH$) in good yield (Ohira et al, "Generation of Alkylidenecarbenes by the Alkenation of Carbonyl Compounds with Lithiotrimethylsilyldiazomethane," *J. Chem. Soc. Chem. Commun.*, 721-722 (1992), which is hereby incorporated by reference in its entirety), while the reaction of cyclosporin aldehyde with lithiotrimethylsilyldiazomethane, followed by acidic workup ($Ac_2O$), provides the acetyl cyclosporin alkyne of Formula I (X=OAc, $R_0$=H or $CH_2OAc$).

Using the above described cyclosporin alkyne (Formula I, X=OH) as a key intermediate, many novel cyclosporin alkyne derivatives can be prepared via palladium or nickel-mediated couplings. As shown in Scheme 3, Sonogashira coupling of cyclosporin alkyne (Formula I) with various aryl halides, heteroaryl halides, and vinyl halides provides novel cyclosporin arylated alkynes of Formula IV and cyclosporin yne-ene analogues of Formula V, respectively. Similarly, the application of palladium-catalyzed coupling to the same key intermediate, cyclosporin alkyne (Formula I), with alkynyl halides leads to the preparation of novel cyclosporin diynes of Formula VI. Utilizing this method, a carbon-carbon triple bond could be introduced step by step to provide a conjugated system of multiple carbon-carbon triple bonds, such as triynes and tetraynes.

Scheme 3

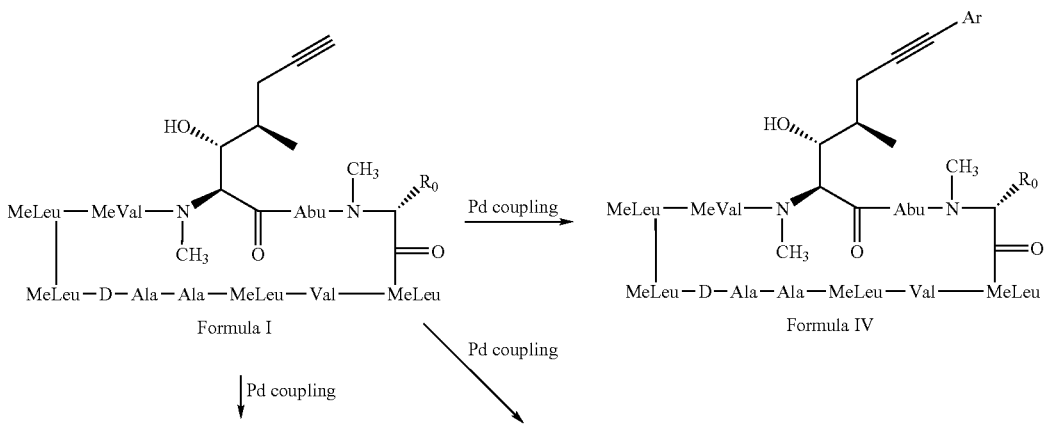

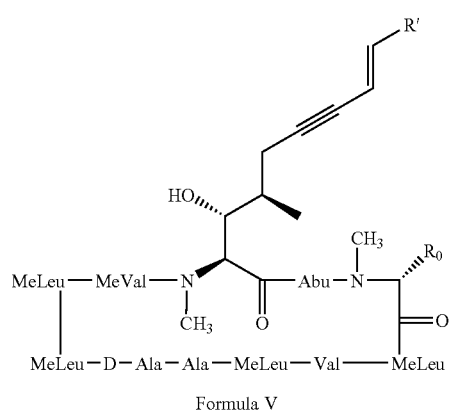

Formula V

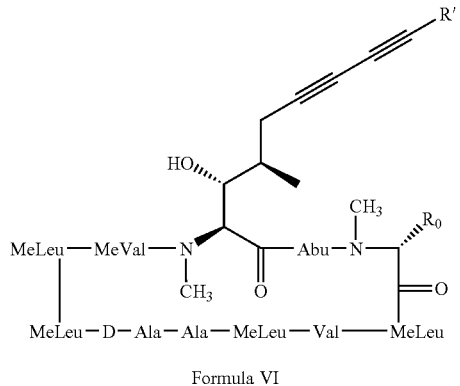

Formula VI

As shown in Scheme 4, the cyclosporin diynes of Formula VI can be prepared using an alternative approach. Bromination of cyclosporin alkyne (Formula I, X=OAc, $R_1$=H) with N-bromosuccinimide in the presence of silver nitrate affords cyclosporin alkynyl bromide (Formula VIII). Using this method, other cyclosporin alkynyl halides, such as cyclosporin alkynyl iodide, can be obtained with N-iodosuccinimide instead of N-bromosuccinimide. Palladium-catalyzed coupling of cyclosporin alkynyl bromide (or cyclosporin alkynyl iodide) with various alkynes affords cyclosporin diynes of Formula VI smoothly.

Scheme 3

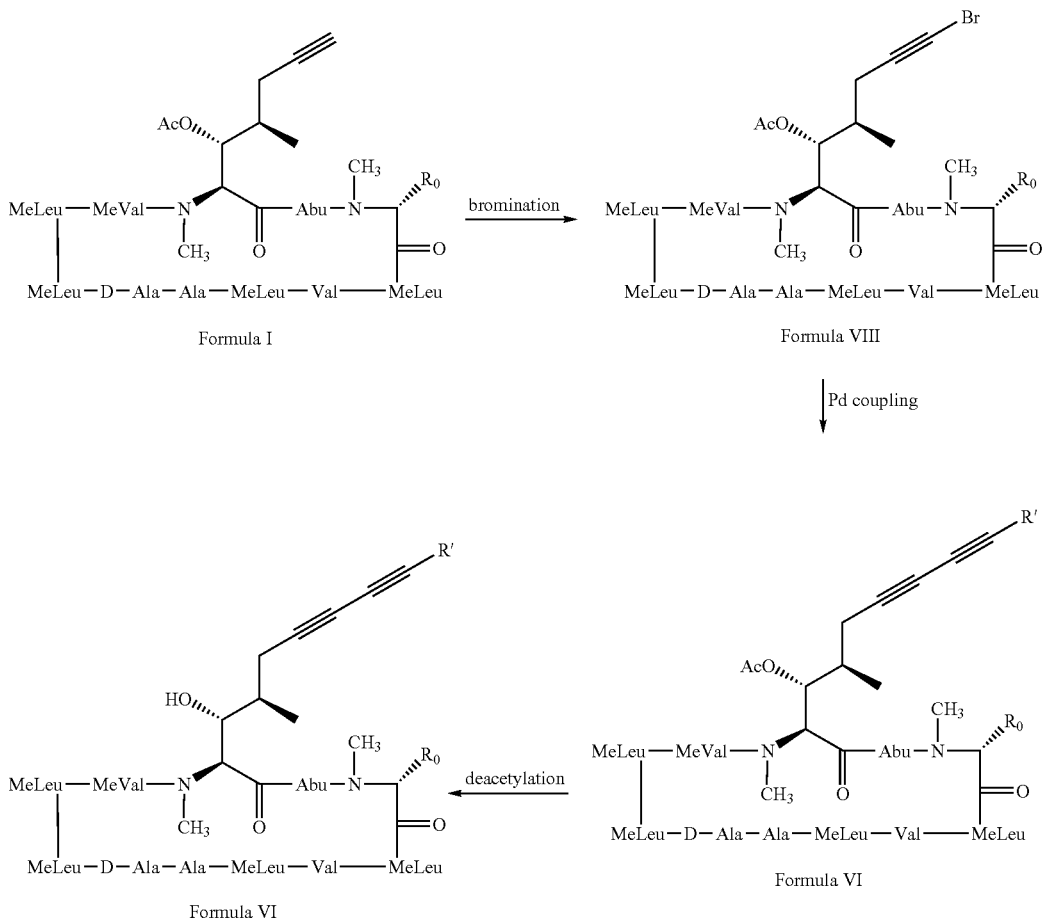

Another embodiment of the present invention relates to the alkylation of cyclosporine alkyne (Formula I, $R_1$=H). As shown in Scheme 5, the treatment of cyclosporine alkyne (Formula I, $R_1$=H) with alkyl halides or aldehyde in the presence of a base (cesium carbonate, benzyltrimethylammonium hydroxide, or other strong bases) provides the alkylated cyclosporin alkyne (Formula IX).

Scheme 5

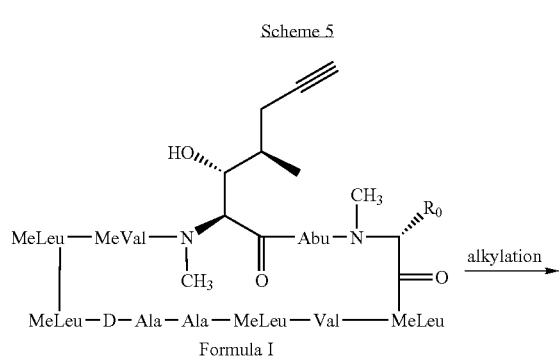

-continued

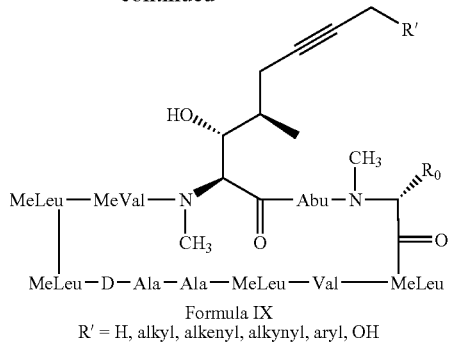

Formula IX
R' = H, alkyl, alkenyl, alkynyl, aryl, OH

Another embodiment of the present invention relates to the incorporation of a carbon-nitrogen double bond (C=N) in the cyclosporin alkyne of Formula I. As shown in Scheme 6, the reaction of cyclosporin alkyne (Formula I, $R_1$=H) with formaldehyde, using benzyltrimethylammonium hydroxide as a base, provides the cyclosporin diol of Formula X. Selective protection of the primary alcohol of the cyclosporin diol with tert-butyldimethylsilyl choloride, followed by acetylation of the second alcohol with acetic anhydride and then desilylation with tetrabutylammonium fluoride, affords the mono-alcohol (Formula XI) smoothly. Swern oxidation of the mono-alcohol affords the cyclosporin aldehyde of Formula XII. Treatment of the aldehyde with hydroxylamine, alkyloxyamines ($RONH_2$), or hydrazines ($R_2NNH_2$) affords the corresponding cyclosporin oximes (CH=N—OR) and hydrazones (CH=N—$NR_2$) of Formula VII, respectively.

Scheme 6

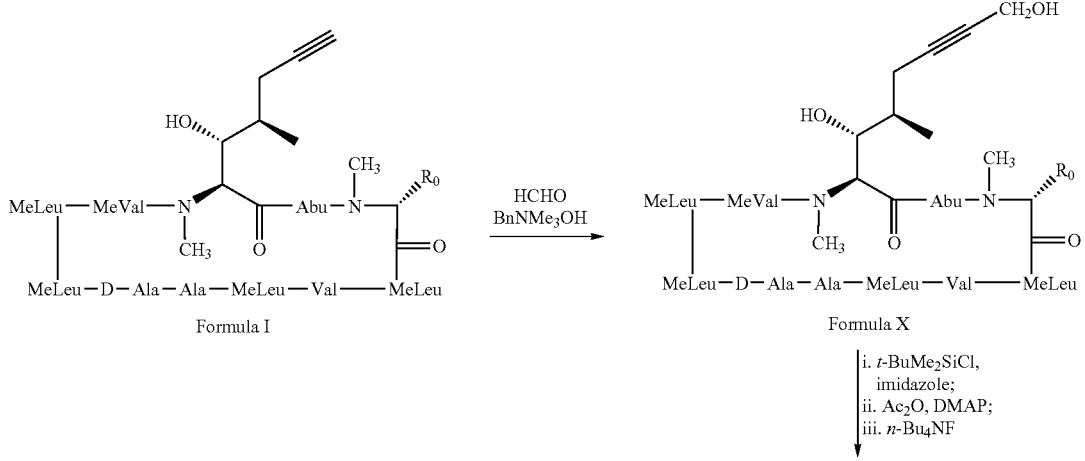

i. $t$-$BuMe_2SiCl$, imidazole;
ii. $Ac_2O$, DMAP;
iii. $n$-$Bu_4NF$

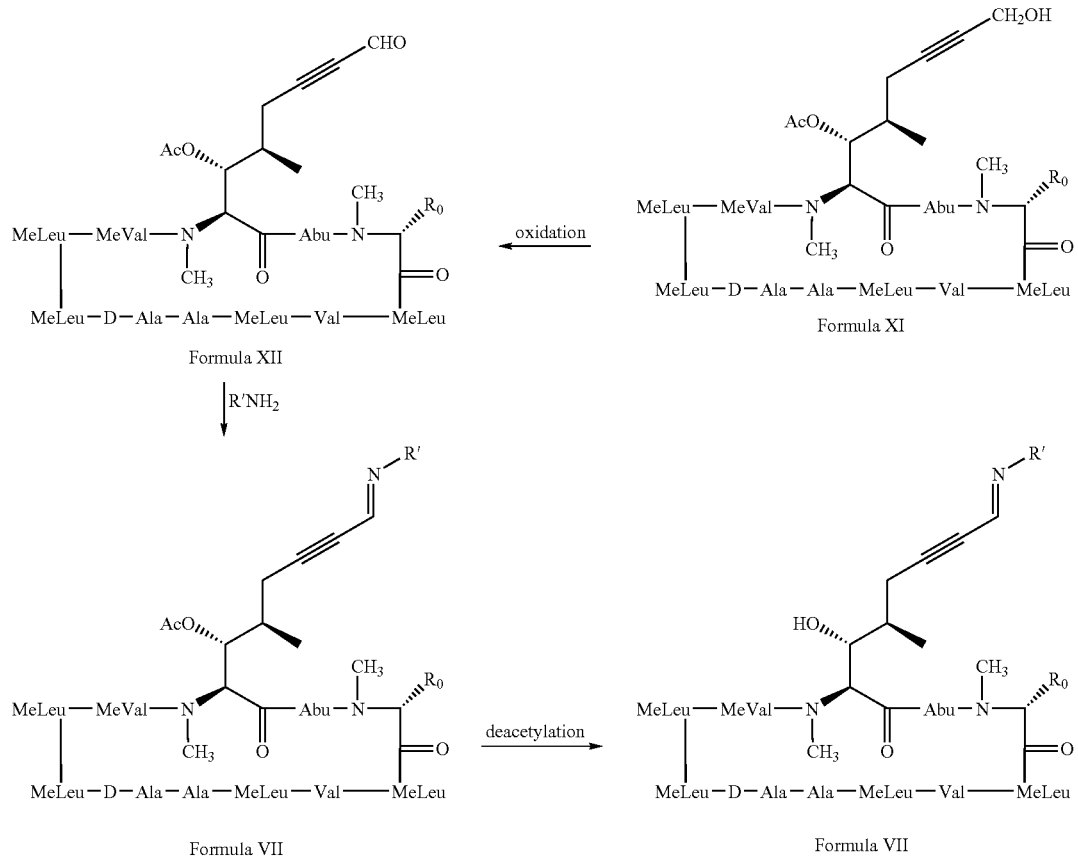

The compounds disclosed in the present invention are particularly useful as immunosuppressive agents. Administration of these compounds suppresses the immune response in organ transplant patients and, thus, prevents allograft rejection. The compounds of the present invention possess enhanced or similar immunosuppressive activity, compared to cyclosporin A. For example, as shown in FIG. 1, the cyclosporin alkyne analogue compound disclosed in Example 25 demonstrates immunosuppressive activity two times more potent over cyclosporin A, while the cyclosporin alkyne analogue compound disclosed in Example 10 shows similar potency to cyclosporin A in the concanavalin A (ConA) stimulated murine splenocyte assay. Table 1 shows the immunosuppressive activities of several novel cyclosporin alkyne analogue compounds disclosed in the present application. (The third column in Table 1 contains cyclosporin A positive control values included for comparison.)

TABLE 1

Immunosuppressive Activities of Novel Cyclosporin Alkyne Analogue Compounds of the Present Invention

| Example Where the Novel Cyclosporin Alkyne Analogue Compound is Disclosed | $IC_{50}$ (ng/mL) | $IC_{50}$ (ng/mL) of CsA |
|---|---|---|
| Example 7 | 25 | 15 |
| Example 10 | 25 | 20 |
| Example 13 | 42 | 15 |
| Example 14 | 32 | 15 |
| Example 22 | 15 | 18 |
| Example 25 | 12 | 20 |
| Example 27 | 12 | 31 |
| Example 29 | 20 | 31 |
| Example 33 | 43 | 15 |
| Example 35 | 77 | 18 |
| Example 38 | 24 | 18 |
| Example 43 | 46 | 18 |

The compounds disclosed in the present invention also possess utility in the treatment of autoimmune and chronic inflammatory diseases, such as asthma, rheumatoid arthritis, multiple sclerosis, psoriasis, and ulcerative colitis, to name only a few.

In addition, the compounds disclosed in the present invention are useful for the treatment of ocular allergy and dry eye. Allergan is currently marketing a topical formulation of cyclosporin A called Restasis™ (cyclosporin ophthalmic emulsion) for the treatment of keratoconjunctivitis sicca or chronic dry eye syndrome in patients whose tear production is presumed to be suppressed due to ocular inflammation. While the exact mechanism of Restasis™ is unknown, it is thought to act as an immunomodulator with anti-inflammatory effects ("Annual Update 2003: Ophthalmic Drugs" *Drugs of the Future*, 28(3): 287-307 (2003); Clark et al., "Ophthalmic Drug Discovery," *Nature Reviews in Drug Discovery*, 2:448-459 (2003), which are hereby incorporated by reference in their entirety).

For treatment of the above mentioned diseases, therapeutically effective doses of the compounds of the present invention may be administered orally, topically, parenterally, by inhalation spray, or rectally in dosage unit formulations containing conventional non-toxic pharmaceutically acceptable carriers, adjuvants, and vehicles. The term parenteral, as used herein, includes subcutaneous injections, intravenous, intramuscular, intrasternal injection, or infusion techniques.

The pharmaceutical compositions containing the active ingredient may be in the form suitable for oral use, for example, as tablets, troches, lozenges, aqueous or oily suspensions, dispersible powders or granules, emulsions, hard or soft capsules, or syrups or elixirs. The pharmaceutical compositions of the present invention contain the active ingredient formulated with one or more pharmaceutically acceptable carriers. As used herein, the term "pharmaceutical acceptable carrier" means a non-toxic, inert solid, semi-solid or liquid filler, diluent, encapsulating material, or formulation auxiliary of any type. Some examples of pharmaceutically acceptable carriers are sugars such as lactose, glucose, and sucrose; starches such as corn starch or potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; non-toxic, compatible lubricants such as sodium lauryl sulfate and magnesium stearate; as well as coloring agents, releasing agents, sweetening, and flavoring and perfuming agents. Preservatives and antioxidants, such as ethyl or n-propyl p-hydroxybenzoate, can also be included in the pharmaceutical compositions.

Dosage forms for topical or transdermal administration of compounds disclosed in the present invention include ointments, pastes, creams, lotions, gels, plasters, cataplasms, powders, solutions, sprays, inhalants, or patches. The active component is admixed under sterile conditions with a pharmaceutically acceptable carrier and any needed preservatives or buffers, as may be required. The ointments, pastes, creams and gels may contain, in addition to an active compound of the present invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

For nasal administration, the compounds disclosed in the present invention can be administered, as suitable, in liquid or powdered form from a nasal applicator. Forms suitable for ophthalmic use will include lotions, tinctures, gels, ointment and ophthalmic inserts, as known in the art. For rectal administration (topical therapy of the colon), the compounds of the present invention may be administered in suppository or enema form, in solution in particular, for Example in vegetable oil or in an oily system for use as a retention enema.

The compounds disclosed in the present invention may be delivered to the lungs by the inhaled route either in nebulizer form or as a dry powder. The advantage of the inhaled route, over the systemic route, in the treatment of asthma and other diseases of airflow obstruction and/or chronic sinusitis, is that patients are exposed to very small quantities of the drug and the compound is delivered directly to the site of action.

Dosages of the compounds of the present invention employed for the treatment of the maladies identified in the present invention will vary depending on the site of treatment, the particular condition to be treated, the severity of the condition, the subject to be treated (who may vary in body weight, age, general health, sex, and other factors) as well as the effect desired.

Dosage levels ranging from about 0.05 mg to about 50 mg per kilogram of body weight per day are useful for the treatment of the conditions or diseases identified in the present invention. This means the amount of the compound disclosed in the present invention that is administered will range from 2.5 mg to about 2.5 gm per patient per day.

The amount of active ingredient that may be combined with the pharmaceutical carrier materials to produce a single dosage form will vary depending upon the host treated and the particular mode of administration. For example, a formulation intended for the oral administration of humans may contain from 2.5 mg to 2.5 gm of active compound of the present invention compounded with an appropriate and convenient amount of carrier material which may vary from about 5 to 95 percent of the total composition. Dosage unit forms will generally contain between from about 5 mg to about 500 mg of active compound of the present invention. Dosage for topical preparation will, in general be less (one tenth to one hundredth) of the dose required for an oral preparation.

EXAMPLES

Example 1

Preparation of Cyclosporin Acetate

A solution of cyclosporin A (5.0 g, 4.16 mmol), acetic anhydride (7.80 mL, 83.2 mmol), and DMAP (760 mg, 6.2 mmol) in methylene chloride (40 mL) was stirred overnight at room temperature under $N_2$ atmosphere. Saturated sodium bicarbonate solution (200 mL) was added to the solution and stirred for an additional 2 h. The mixture was extracted with ether, washed with 1 N HCl, neutralized with saturated sodium bicarbonate solution, washed with brine, dried over sodium sulfate, and concentrated in vacuo to afford cyclosporin acetate (4.92 g, 95%) as a white solid: $^1$H NMR (300 MHz, CDCl$_3$) δ 8.57 (d, J=9.6 Hz, 1H), 8.04 (d, J=6.9 Hz, 1H), 7.51 (d, J=9.4 Hz, 1H), 7.47 (d, J=7.8 Hz, 1H), 5.67 (dd, J=11.0, 4.0 Hz, 1H), 5.60-5.44 (m, 2H), 5.39 (dd, J=11.7, 3.7 Hz, 1H), 5.32-5.13 (m, 4H), 5.06-4.93 (m, 2H), 4.85 (t, J=7.2 Hz, 1H), 4.77 (t, J=9.6 Hz, 1H), 4.65 (d, J=13.7 Hz, 1H), 4.41 (t, J=7.0 Hz, 1H), 3.46 (s, 3H), 3.26 (s, 3H), 3.24 (s, 3H), 3.21 (s, 3H), 3.10 (s, 3H), 2.68 (s, 3H), 2.66 (s, 3H), 2.50-2.35 (m, 1H), 2.25-1.80 (m, 6H), 2.08 (s, 3H), 2.01 (s, 3H), 1.75-1.55 (m, 6H), 1.45-0.75 (m, 55H); ESI MS m/z 1245 [$C_{64}H_{113}N_{11}O_{13}$+H]$^+$.

Example 2

Preparation of Acetyl Cyclosporin Aldehyde

Ozone was bubbled into a solution of cyclosporin acetate from Example 1 (3.0 g, 2.4 mmol) in methylene chloride (70 mL) at −78° C. until a blue color was developed. The mixture was degassed with nitrogen for a few min and dimethylsulfide (3 mL) was added at −78° C. The reaction mixture was allowed to warm to room temperature and stirred for 3 h. The reaction mixture was concentrated in vacuo and the residue was dissolved in ethyl acetate (300 mL), washed with water (2×70 mL) and brine (70 mL), dried over sodium sulfate, filtered, and concentrated in vacuo to afford acetyl cyclosporin aldehyde (2.79 g, 94%) as a white solid. The crude product was carried to the next step without further purification: $^1$H NMR MHz, CDCl$_3$) δ 9.60 (d, J=3.5 Hz, 1H), 8.55 (d, J=9.7 Hz, 1H), 7.96 (d, J=6.8 Hz, 1H), 7.52 (d, J=7.7 Hz, 1H), 7.46 (d, J=9.0 Hz, 1H), 5.67 (dd, J=11.0, 3.8 Hz, 1H), 5.60-5.45 (m, 2H), 5.32 (dd, J=12.1, 3.3 Hz, 1H), 5.24-5.10 (m, 2H), 5.08-4.90 (m, 2H), 4.84 (t, J=7.1 Hz, 1H), 4.73 (t, J=9.6 Hz, 1H), 4.64 (d, J=13.8 Hz, 1H), 4.41 (t, J=7.0 Hz, 1H), 3.46 (s, 3H), 3.29 (s, 6H), 3.21 (s, 3H), 3.08 (s, 3H), 2.67 (s, 3H), 2.65 (s, 3H), 2.50-2.35 (m, 2H), 2.25-1.80 (m, 6H), 1.99 (s, 3H), 1.75-1.55 (m, 3H), 1.50-0.75 (m, 57H); ESI MS m/z 1233 [C$_{62}$H$_{109}$N$_{11}$O$_{14}$+H]$^+$.

Example 3

Preparation of Cyclosporin Alkyne

To a stirred solution of acetyl cyclosporin aldehyde from Example 2 (1.94 g, 1.57 mmol) in methanol (20 mL) was added a solution of dimethyl (1-diazo-2-oxopropyl)phosphonate (3.01 g, 15.7 mmol) in methanol (10 mL) followed by potassium carbonate (2.17 g, 15.7 mmol). The resulting green suspension was stirred at room temperature overnight. The solution was filtered through diatomaceous earth and the filtrate was concentrated. The residue was dissolved in ethyl acetate (300 mL) and washed with water (2×100 mL). The combined aqueous layers were extracted with ethyl acetate (100 mL). The combined organic layers were washed with brine, dried over sodium sulfate, and concentrated to dryness. Purification by semi-preparative HPLC gave cyclosporin alkyne (848 mg, 45%) as a white solid: $^1$H NMR (300 MHz, CDCl$_3$) δ 7.86 (d, J=9.7 Hz, 1H), 7.62 (d, J=9.3 Hz, 1H), 7.56 (d, J=6.9 Hz, 1H), 7.34 (d, J=7.7 Hz, 1H), 5.73-5.68 (m, 1H), 5.57-5.45 (m, 2H), 5.22-4.45 (m, 12H), 4.03-3.98 (m, 1H), 3.49 (s, 3H), 3.38 (s, 3H), 3.24 (s, 3H), 3.09 (s, 3H), 3.08 (s, 3H), 2.72 (s, 3H), 2.70 (s, 3H), 2.50-0.64 (m, 66H); ESI MS m/z 1187 [C$_{61}$H$_{107}$N$_{11}$O$_{12}$+H]$^+$.

Example 4

Preparation of Cyclosporin Alkyne

To a −78° C. solution of (trimethylsilyl)diazomethane (4.6 mL, 2.0 M solution in Et$_2$O, 9.2 mmol) in THF (5 mL) was added n-BuLi (3.4 mL, 2.5 M solution in hexanes, 8.4 mmol) dropwise. The resulting yellow suspension was stirred for 30 min, and then a solution of acetyl cyclosporine aldehyde from Example 2 (1.03 g, 0.84 mmol) in THF (5 mL) was added dropwise. The mixture was stirred at −78° C. for 30 min then warmed to 0° C. for 15 min. The reaction was quenched with saturated NH$_4$Cl. The mixture was partitioned between EtOAc and H$_2$O. The aqueous layer was extracted with EtOAc. The combined organics were washed with brine, dried over Na$_2$SO$_4$, and concentrated. Purification by semi-preparative HPLC gave the cyclosporine alkyne (364 mg, 37%) as a white solid: $^1$H NMR (300 MHz, CDCl$_3$) δ 7.86 (d, J=9.7 Hz, 1H), 7.62 (d, J=9.3 Hz, 1H), 7.56 (d, J=6.9 Hz, 1H), 7.34 (d, J=7.7 Hz, 1H), 5.73-5.68 (m, 1H), 5.57-5.45 (m, 2H), 5.22-4.45 (m, 12H), 4.03-3.98 (m, 1H), 3.49 (s, 3H), 3.38 (s, 3H), 3.24 (s, 3H), 3.09 (s, 3H), 3.08 (s, 3H), 2.72 (s, 3H), 2.70 (s, 3H), 2.50-0.64 (m, 66H); ESI MS m/z 1187 [C$_{61}$H$_{107}$N$_{11}$O$_{12}$+H]$^+$.

Example 5

Preparation of the Acetate of Cyclosporin Alkyne

To a −78° C. solution of (trimethylsilyl)diazomethane (4.5 mL, 2.0 M solution in Et$_2$O, 8.9 mmol) in THF (10 mL) was added n-BuLi (3.2 mL, 2.5 M solution in hexanes, 8.1 mmol) dropwise. The resulting yellow suspension was stirred for 30 min, and then a solution of acetyl cyclosporine aldehyde from Example 2 (1.00 g, 0.81 mmol) in THF (5 mL) was added dropwise. The mixture was stirred at −78° C. for 5 min. The reaction was quenched with a mixture of acetic anhydride (1.5 mL, 4.1 mmol) and pyridine (1.4 mL, 4.9 mmol) in THF (5 mL) and then warmed to room temperature for 15 min. The reaction was quenched with saturated NH$_4$Cl. The mixture was partitioned between Et$_2$O and H$_2$O. The aqueous layer was extracted with Et$_2$O. The combined organics were washed with brine, dried over Na$_2$SO$_4$, and concentrated. Purification by semi-preparative HPLC gave the acetate of cyclosporine alkyne (389 mg, 40%) as a white solid: $^1$H NMR (300 MHz, CDCl$_3$) δ 8.46 (d, J=9.5 Hz, 1H), 8.07 (d, J=6.9 Hz, 1H), 7.72 (d, J=9.1 Hz, 1H), 7.54 (d, J=7.7 Hz, 1H), 5.69 (dd, J=10.8, 3.6 Hz, 1H), 5.55-5.40 (m, 3H), 5.30 (dd, J=11.7, 3.6 Hz, 1H), 5.15 (t, J=6.1 Hz, 1H), 5.02-4.60 (m, 5H), 4.47 (t, J=6.9 Hz, 1H), 3.46 (s, 3H), 3.28 (s, 3H), 3.23 (s, 3H), 3.20 (s, 3H), 3.07 (s, 3H), 2.69 (s, 3H), 2.67 (s, 3H), 2.45-2.35 (m, 1H), 2.30-2.02 (m, 5H), 2.00 (s, 3H), 1.95-1.55 (m, 8H), 1.45-0.75 (m, 55H); ESI MS m/z 1229 [C$_{63}$H$_{109}$N$_{11}$O$_{13}$+H]$^+$.

Example 6

Preparation of the Acetate of Cyclosporin Alkyne

To a solution of cyclosporine alkyne from Example 3 (0.44 g, 0.37 mmol) in methylene chloride (5 mL) was added pyridine (0.90 mL, 11.1 mmol) followed by DMAP (68 mg, 0.55 mmol) and acetic anhydride (0.70 mL, 7.4 mmol), then the mixture was stirred at room temperature for 1.5 d. The reaction mixture was diluted with ethyl ether (100 mL), washed with a saturated solution of sodium bicarbonate (30 mL) and brine (30 mL). The organic layer was dried over anhydrous sodium sulfate and concentrated under vacuum. The crude material was purified by semi-preparative HPLC to afford the acetate of cyclosporine alkyne (0.23 g, 51%) as a white solid: $^1$H NMR (300 MHz, CDCl$_3$) δ 8.46 (d, J=9.5 Hz, 1H), 8.07 (d, J=6.9 Hz, 1H), 7.72 (d, J=9.1 Hz, 1H), 7.54 (d, J=7.7 Hz, 1H), 5.69 (dd, J=10.8, 3.6 Hz, 1H), 5.55-5.40 (m, 3H), 5.30 (dd, J=11.7, 3.6 Hz, 1H), 5.15 (t, J=6.1 Hz, 1H), 5.02-4.60 (m, 5H), 4.47 (t, J=6.9 Hz, 1H), 3.46 (s, 3H), 3.28 (s, 3H), 3.23 (s, 3H), 3.20 (s, 3H), 3.07 (s, 3H), 2.69 (s, 3H), 2.67 (s, 3H), 2.45-2.35 (m, 1H), 2.30-2.02 (m, 5H), 2.00 (s, 3H), 1.95-1.55 (m, 8H), 1.45-0.75 (m, 55H); ESI MS m/z 1229 [C$_{63}$H$_{109}$N$_{11}$O$_{13}$+H]$^+$.

Example 7

Preparation of Cyclosporin yne-ene

To a mixture of cyclosporin alkyne from Example 3 (55 mg, 0.046 mmol), copper(I) iodide (4 mg, 0.023 mmol), dichlorobis(triphenylphosphine)palladium(II) (16 mg, 0.023 mmol) in triethylamine (2 mL) was added vinyliodide (34 µL, 0.46 mmol), then the mixture was stirred at room temperature for 1 h. The reaction mixture was filtered through a micro-filter and concentrated under vacuum. The crude material was purified by semi-preparative HPLC to afford cyclosporin yne-ene (24 mg, 43%) as a white solid: $^1$H NMR (300 MHz, CDCl$_3$) δ 8.11 (d, J=9.3 Hz, 1H), 7.75 (d, J=7.2 Hz, 1H), 7.56 (d, J=8.4 Hz, 1H), 7.30 (d, J=7.8 Hz, 1H), 5.80-5.65 (m, 3H), 5.56 (d, J=2.4 Hz, 1H), 5.52-5.36 (m, 4H), 5.30 (dd, J=11.4, 3.6 Hz, 1H), 5.20-4.95 (m, 6H), 4.84 (t, J=7.2 Hz, 2H), 4.72-4.60 (m, 2H), 4.53 (t, J=7.2 Hz, 1H), 3.88 (t, J=6.3 Hz, 1H), 3.50 (s, 3H), 3.38 (s, 3H), 3.27 (s, 3H), 3.13 (s, 3H), 3.10 (s, 3H), 2.71 (s, 3H), 2.70 (s, 3H), 2.45-2.35 (m, 2H), 2.20-1.80 (m, 8H), 1.75-1.55 (m, 5H), 1.45-0.75 (m, 48H); ESI MS m/z 1213 [C$_{63}$H$_{109}$N$_{11}$O$_{12}$+H]$^+$; HPLC 98.6% (AUC), t$_R$=19.32 min.

Example 8

Preparation of trans-Cyclosporin yne-ene

To a mixture of cyclosporin alkyne from Example 3 (65 mg, 0.055 mmol), copper(I) iodide (5 mg, 0.028 mmol), dichlorobis(triphenylphosphine)palladium(II) (20 mg, 0.028 mmol) in triethylamine (2 mL) was added trans-1,2-dichloroethylene (85 µL, 1.1 mmol), then the mixture was stirred at room temperature for 4 h. The reaction mixture was filtered through a micro-filter and concentrated under vacuum. The crude material was purified by semi-preparative HPLC to afford trans-cyclosporin yne-ene (13 mg, 19%) as a white solid: $^1$H NMR (300 MHz, CDCl$_3$) δ 8.08 (d, J=9.6 Hz, 1H), 7.71 (d, J=7.2 Hz, 1H), 7.57 (d, J=8.1 Hz, 1H), 7.27 (d, J=7.8 Hz, 1H), 6.43 (d, J=13.6 Hz, 1H), 5.90 (d, J=13.6 Hz, 1H), 5.70 (dd, J=10.8, 3.6 Hz, 1H), 5.45 (d, J=6.3 Hz, 1H), 5.30 (dd, J=11.7, 3.6 Hz, 1H), 5.17-4.92 (m, 5H), 4.83 (t, J=6.9 Hz, 1H), 4.75-4.62 (m, 2H), 4.54 (t, J=7.2 Hz, 1H), 3.85 (t, J=6.3 Hz, 1H), 3.49 (s, 3H), 3.39 (s, 3H), 3.27 (s, 3H), 3.12 (s, 3H), 3.11 (s, 3H), 2.71 (s, 3H), 2.70 (s, 3H), 2.45-2.35 (m, 2H), 2.20-1.80 (m, 8H), 1.75-1.55 (m, 5H), 1.45-0.75 (m, 53H); ESI MS m/z 1247 [C$_{63}$H$_{108}$ClN$_{11}$O$_{12}$+H]$^+$; HPLC>99% (AUC), t$_R$=19.92 min.

Example 9

Preparation of the Acetate of cis-Cyclosporin yne-ene

To a mixture of the acetate of cyclosporine alkyne from Example 6 (166 mg, 0.14 mmol), copper(I) iodide (13 mg, 0.068 mmol), dichlorobis(triphenylphosphine)palladium(II) (48 mg, 0.068 mmol) in triethylamine (4 mL) was added cis-1,2-dichloroethylene (0.20 mL, 2.7 mmol), then the mixture was stirred at room temperature for 12 h. Cis-1,2-dichloroethylene (0.10 mL, 1.3 mmol) was refilled, and the mixture was stirred for 5 h. The reaction mixture was filtered through a micro-filter and concentrated under vacuum. The crude material was purified by semi-preparative HPLC to afford the acetate of cis-cyclosporin yne-ene (22 mg, 13%) as a white solid: $^1$H NMR (300 MHz, CDCl$_3$) δ 8.45 (d, J=9.6 Hz, 1H), 8.08 (d, J=7.2 Hz, 1H), 7.79 (d, J=8.1 Hz, 1H), 7.59 (d, J=7.8 Hz, 1H), 6.28 (d, J=7.4 Hz, 1H), 5.82 (d, J=7.4 Hz, 1H), 5.70 (dd, J=10.8, 3.6 Hz, 1H), 5.62-5.10 (m, 5H), 5.03-4.72 (m, 4H), 4.64 (d, J=13.8 Hz, 1H), 4.48 (t, J=7.0 Hz, 1H), 3.44 (s, 3H), 3.29 (s, 3H), 3.24 (s, 3H), 3.19 (s, 3H), 3.08 (s, 3H), 2.69 (s, 3H), 2.68 (s, 3H), 2.45-2.35 (m, 1H), 2.30-2.05 (m, 7H), 1.99 (s, 3H), 1.95-1.60 (m, 5H), 1.45-0.75 (m, 55H); ESI MS m/z 1289 [C$_{65}$H$_{110}$ClN$_{11}$O$_{13}$+H]$^+$.

Example 10

Preparation of cis-Cyclosporin yne-ene

To a solution of acetate of cis-cyclosporin yne-ene from Example 9 (22 mg, 0.017 mmol) in MeOH (3 mL) was added potassium carbonate (47 mg, 0.34 mmol), then the mixture was stirred at room temperature for 8 h. The reaction mixture was diluted with ethyl acetate (30 mL), then washed with water (10 mL). The aqueous layer was separated and extracted with ethyl acetate (30 mL). The combined organics were dried over anhydrous sodium sulfate and concentrated under vacuum. The crude material was purified by semi-preparative HPLC to afford cis-cyclosporin yne-ene (16 mg, 76%) as a white solid: $^1$H NMR (300 MHz, CDCl$_3$) δ 8.13 (d, J=9.6 Hz, 1H), 7.76 (d, J=7.2 Hz, 1H), 7.60 (d, J=8.3 Hz, 1H), 7.33 (d, J=7.8 Hz, 1H), 6.30 (d, J=7.3 Hz, 1H), 5.83 (d, J=7.3 Hz, 1H), 5.71 (dd, J=11.1, 4.0 Hz, 1H), 5.44 (d, J=6.7 Hz, 1H), 5.31 (dd, J=11.5, 3.6 Hz, 1H), 5.17-4.95 (m, 5H), 4.84 (t, J=7.2 Hz, 1H), 4.75-4.62 (m, 2H), 4.54 (t, J=7.2 Hz, 1H), 3.92 (t, J=6.5 Hz, 1H), 3.49 (s, 3H), 3.39 (s, 3H), 3.27 (s, 3H), 3.12 (s, 3H), 3.10 (s, 3H), 2.72 (s, 3H), 2.71 (s, 3H), 2.45-2.25 (m, 2H), 2.20-1.90 (m, 6H), 1.80-1.55 (m, 5H), 1.45-0.75 (m, 55H); ESI MS m/z 1247 [C$_{63}$H$_{108}$ClN$_{11}$O$_{12}$+H]$^+$; HPLC>99% (AUC), t$_R$=19.21 min.

Example 11

Preparation of the Acetate of trans-Cyclosporin yne-ene

To a mixture of the acetate of cyclosporin alkyne from Example 6 (74 mg, 0.06 mmol), copper(I) iodide (6 mg, 0.03 mmol), dichlorobis(triphenylphosphine)palladium(II) (21 mg, 0.03 mmol) in triethylamine (2 mL) was added (2-bromovinyl)trimethylsilane (0.18 mL, 1.2 mmol), then the mixture was stirred at room temperature for 12 h. The reaction mixture was filtered through a micro-filter and concentrated under vacuum. The crude material was purified by semi-preparative HPLC to afford the acetate of trans-cyclosporin yne-ene (16 mg, 20%) as a white solid: $^1$H NMR (300 MHz, CDCl$_3$) δ 8.48 (d, J=9.6 Hz, 1H), 8.07 (d, J=7.2 Hz, 1H), 7.66 (d, J=8.1 Hz, 1H), 7.54 (d, J=7.8 Hz, 1H), 6.24 (d, J=19.2 Hz, 1H), 5.88 (d, J=19.2 Hz, 1H), 5.70 (dd, J=10.8, 3.6 Hz, 1H), 5.55-5.10 (m, 6H), 5.03-4.92 (m, 2H), 4.86 (t, J=7.2 Hz, 1H), 4.76 (t, J=9.5 Hz, 1H), 4.64 (d, J=13.9 Hz, 1H), 4.46 (t, J=7.2 Hz, 1H), 3.44 (s, 3H), 3.31 (s, 3H), 3.25 (s, 3H), 3.20 (s, 3H), 3.07 (s, 3H), 2.69 (s, 3H), 2.67 (s, 3H), 2.45-2.35 (m, 1H), 2.30-2.05 (m, 7H), 1.98 (s, 3H), 1.75-1.55 (m, 3H), 1.45-0.75 (m, 56H), 0.07 (s, 9H); ESI MS m/z 1327 [C$_{68}$H$_{119}$N$_{11}$O$_{13}$Si+H]$^+$.

Example 12

Preparation of trans-Cyclosporin yne-ene

To a solution of the acetate of trans-cyclosporin yne-ene from Example 11 (16 mg, 0.012 mmol) in MeOH (2 mL)

was added potassium carbonate (41 mg, 0.30 mmol), then the mixture was stirred at room temperature for 8 h. The reaction mixture was diluted with ethyl acetate (30 mL), then washed with water (10 mL). The aqueous layer was separated and extracted with ethyl acetate (30 mL). The combined organics were dried over anhydrous sodium sulfate and concentrated under vacuum. The crude material was purified by semi-preparative HPLC to afford trans-cyclosporin yne-ene (6 mg, 40%) as a white solid: $^1$H NMR (300 MHz, CDCl$_3$) δ 8.12 (d, J=9.8 Hz, 1H), 7.78 (d, J=7.2 Hz, 1H), 7.58 (d, J=8.2 Hz, 1H), 7.34 (d, J=7.9 Hz, 1H), 6.30 (d, J=19.2 Hz, 1H), 5.89 (d, J=19.2 Hz, 1H), 5.71 (dd, J=11.3, 4.1 Hz, 1H), 5.39 (d, J=7.1 Hz, 1H), 5.30 (dd, J=11.4, 3.4 Hz, 1H), 5.20-4.95 (m, 5H), 4.83 (t, J=7.2 Hz, 1H), 4.75-4.65 (m, 2H), 4.53 (t, J=7.2 Hz, 1H), 3.92 (t, J=6.4 Hz, 1H), 3.49 (s, 3H), 3.38 (s, 3H), 3.27 (s, 3H), 3.13 (s, 3H), 3.10 (s, 3H), 2.72 (s, 3H), 2.71 (s, 3H), 2.60-2.35 (m, 2H), 2.20-1.55 (m, 12H), 1.45-0.75 (m, 54H), 0.07 (s, 9H); ESI MS m/z 1285 [C$_{66}$H$_{117}$N$_{11}$O$_{12}$Si+H]$^+$; HPLC 98.5% (AUC), t$_R$=22.71 min.

Example 13

Preparation of trans-Cyclosporin yne-ene

To a mixture of cyclosporine alkyne from Example 3 (40 mg, 0.03 mmol) in triethylamine (2 mL) and tetrahydrofuran (1 mL) was added dichlorobis(triphenylphosphine)palladium(II) (15 mg, 0.02 mmol), copper(I) iodide (4 mg, 0.02 mmol) and trans-1-bromopropene (50 μL, 0.6 mmol), then the mixture was stirred at room temperature for 3 h. The reaction mixture was filtered through a micro-filter and concentrated under vacuum. Purification twice by semi-preparative HPLC gave trans-cyclosporin yne-ene (5.5 mg, 15%) as a yellow solid: $^1$H NMR (300 MHz, CDCl$_3$) δ 8.10 (d, J=5.6 Hz, 1H), 7.75-7.67 (m, 3H), 7.49-7.38 (m, 4H), 6.05-5.99 (m, 1H), 5.70 (dd, J=10.9, 4.2 Hz, 1H), 5.42 (dd, J=15.8, 1.8 Hz, 1H), 5.36 (d, J=7.0 Hz, 1H), 5.28 (dd, J=11.4, 3.5 Hz, 1H), 5.19-5.17 (m, 1H), 5.09 (t, J=6.7 Hz, 1H), 5.06-4.98 (m, 3H), 4.84 (t, J=7.2 Hz, 1H), 4.73-4.68 (m, 3H), 4.49 (t, J=7.3 Hz, 1H), 3.90 (t, J=6.6 Hz, 1H), 3.49 (s, 3H), 3.38 (s, 3H), 3.27 (s, 3H), 3.13 (s, 3H), 3.09 (s, 3H), 2.71 (s, 3H), 2.70 (s, 3H), 2.55-1.80 (m, 12H), 1.75-1.56 (m, 13H), 1.50-1.19 (m, 41H); ESI MS m/z 1227 [C$_{64}$H$_{111}$N$_{11}$O$_{12}$+H]$^+$; HPLC>99% (AUC), t$_R$=19.76 min.

Example 14

Preparation of cis-Cyclosporin yne-ene

A mixture of cyclosporin alkyne from Example 3 (80 mg, 0.07 mmol), cis-1-bromopropene (300 μL, 3.5 mmol) and copper(I) iodide (14 mg, 0.07 mmol) in triethylamine (3 mL) was stirred until a clear solution formed. Dichlorobis(triphenylphosphine)palladium(II) (51 mg, 0.07 mmol) was added, and then the mixture was stirred at room temperature overnight. The reaction mixture was filtered through a micro-filter and concentrated under vacuum. The residue was purified by column chromatography (silica gel, 7:3 hexanes/ethyl acetate to ethyl acetate) to give a brown solid. The solid was further purified twice by semi-preparative HPLC to afford cis-cyclosporin yne-ene (29 mg, 35%) as a white solid: $^1$H NMR (300 MHz, CDCl$_3$) δ 8.15 (d, J=9.5 Hz, 1H), 7.77 (d, J=7.3 Hz, 1H), 7.51 (d, J=8.5 Hz, 1H), 7.27 (d, J=6.4 Hz, 1H), 5.94-5.83 (m, 1H), 5.70 (dd, J=11.0, 4.2 Hz, 1H), 5.45-5.39 (m, 2H), 5.29 (dd, J=11.5, 3.8 Hz, 1H), 5.20-5.16 (m, 1H), 5.10-4.97 (m, 4H), 4.88-4.79 (m, 1H), 4.74-4.67 (m, 3H), 4.54-4.47 (m 1H), 3.90 (t, J=6.5 Hz, 1H), 3.50 (s, 3H), 3.39 (s, 3H), 3.27 (s, 3H), 3.13 (s, 3H), 3.10 (s, 3H), 2.71 (s, 3H), 2.70 (s, 3H), 2.48-0.80 (m, 70H); ESI MS m/z 1227 [C$_{64}$H$_{111}$N$_{11}$O$_{12}$+H]$^+$, HPLC>99% (AUC), t$_R$=19.85 min.

Example 15

Preparation of Cyclosporin yne-ene

To a mixture of cyclosporin alkyne from Example 3 (40 mg, 0.03 mmol) in triethylamine (2 mL) and tetrahydrofuran (1 mL) was added dichlorobis(triphenylphosphine)palladium(II) (15 mg, 0.02 mmol), copper(I) iodide (4 mg, 0.02 mmol) and 2-bromopropene (50 μL, 0.6 mmol), then the mixture was stirred at room temperature for 5 h. The reaction mixture was filtered through a micro-filter and concentrated under vacuum. Purification twice by semi-preparative HPLC gave cyclosporin yne-ene (4.5 mg, 12%) as a white solid: $^1$H NMR (300 MHz, CDCl$_3$) δ 8.12 (d, J=9.0 Hz, 1H), 7.74 (d, J=7.3 Hz, 1H), 7.49 (d, J=8.3 Hz, 1H), 7.22 (d, J=7.8 Hz, 1H), 5.71 (dd, J=10.9, 4.3 Hz, 1H), 5.41 (d, J=6.8 Hz, 1H), 5.35 (dt, J=9.1, 5.8 Hz, 1H), 5.27 (dd, J=11.5, 3.7 Hz, 1H), 5.20-5.18 (m, 3H), 5.14 (s, 1H), 5.08 (t, J=6.9 Hz, 1H), 5.05-4.98 (m, 2H), 4.84 (app quintet, J=6.9 Hz, 1H), 4.73-4.67 (m, 2H), 4.52 (app quintet, J=7.4 Hz, 1H), 3.88 (t, J=6.5 Hz, 1H), 3.50 (s, 3H), 3.38 (s, 3H), 3.28 (s, 3H), 3.21-3.18 (m, 1H), 3.13 (s, 3H), 3.10 (s, 3H), 2.71 (s, 3H), 2.70 (s, 3H), 2.60 (dd, J=17.1, 3.9 Hz, 1H), 2.46-2.35 (m, 1H), 2.63 (t, J=7.7 Hz, 1H), 2.18-2.07 (m, 6H), 2.05-1.96 (m, 3H), 1.90-1.82 (m, 5H), 1.81-1.59 (m, 5H), 1.52-1.38 (m, 4H), 1.36-1.23 (m, 13H), 1.01-0.84 (m, 30H); ESI MS m/z 1227 [C$_{64}$H$_{111}$N$_{11}$O$_{12}$+H]$^+$; HPLC 98.8% (AUC), t$_R$=19.82 min.

Example 16

Preparation of Cyclosporin yne-ene

To a mixture of cyclosporin alkyne from Example 3 (80 mg, 0.07 mmol) and copper(I) iodide (13 mg, 0.07 mmol) in triethylamine (3 mL) was added bromostyrene (a mixture of cis and trans isomers, 180 μL, 1.4 mmol) then the mixture was stirred until a clear solution formed. Dichlorobis(triphenylphosphine)palladium(II) (50 mg, 0.07 mmol) was added, and then the mixture was stirred at room temperature overnight. The reaction mixture was filtered through a micro-filter and concentrated under vacuum. The residue was purified by column chromatography (silica gel, 7:3 hexanes/ethyl acetate to ethyl acetate) to give a brown solid. The solid was further purified twice by semi-preparative HPLC to afford cyclosporin yne-ene (17 mg, 19%) as a white solid and a mixture of isomers (cis/trans ~1:4 by $^1$H NMR): $^1$H NMR (500 MHz, CDCl$_3$) δ 8.10 (d, J=9.7 Hz, 1H), 7.81 (d, J=7.4 Hz, 1H), 7.71 (d, J=7.4 Hz, 1H), 7.47 (d, J=8.5 Hz, 1H), 7.38-7.29 (m, 12H), 6.94-6.83 (m, 4H), 5.70 (dd, J=11.0, 4.3 Hz, 1H), 5.44 (d, J=6.9 Hz, 2H), 5.19-5.15 (n, 2H), 5.08 (t, J=7.3 Hz, 1H), 5.06-5.00 (m, 6H), 4.83 (t, J=7.7 Hz, 1H), 4.73-4.69 (m, 4H), 4.55-4.40 (m, 3H), 3.92 (t, J=6.6 Hz, 1H), 3.63 (s, 3H), 3.52 (s, 3H), 3.40 (s, 3H), 3.29 (s, 3H), 3.12 (s, 3H), 3.11 (s, 3H), 2.50-1.87 (m, 10H), 1.84-1.57 (m, 3H), 1.55-1.19 (m, 10H), 1.08-0.70 (m, 31H); ESI MS m/z 1289 [C$_{69}$H$_{113}$N$_{11}$O$_{12}$+H]$^+$; HPLC 98.2% (AUC), t$_R$=20.66 min.

Example 17

Preparation of Phenyl Cyclosporin Alkyne

A mixture of cyclosporin alkyne from Example 3 (80 mg, 0.07 mmol) in triethylamine (3 mL) was degassed with $N_2$ for 5 min. Dichlorobis(triphenylphosphine)palladium(II) (28 mg, 0.04 mmol), copper(I) iodide (8 mg, 0.04 mmol) and iodobenzene (80 μL, 0.70 mmol) were added, then the mixture was stirred at room temperature for 1.5 h. The reaction mixture was filtered through a micro-filter and concentrated under vacuum. Purification by semi-preparative HPLC gave cyclosporine phenyl alkyne (7 mg, 8%) as a brown solid: $^1$H NMR (500 MHz, CDCl$_3$) δ 8.18 (d, J=9.8 Hz, 1H), 7.78 (d, J=7.4 Hz, 1H), 7.71-7.68 (m, 1H), 7.51 (d, J=8.3 Hz, 1H), 7.40-7.37 (m, 4H), 7.20 (d, J=7.9 Hz, 1H), 5.69 (dd, J=10.6, 3.7 Hz, 1H), 5.45 (d, J=6.9 Hz, 1H), 5.32-5.27 (m, 1H), 5.20-5.16 (m, 1H), 5.09-4.97 (m, 4H), 4.83 (t, J=7.1 Hz, 1H), 4.74-4.67 (m, 2H), 4.52 (t, J=7.3 Hz, 1H), 3.92 (t, J=6.5 Hz, 1H), 3.53 (s, 3H), 3.40 (s, 3H), 3.30 (s, 3H), 3.22-3.17 (m, 2H), 3.13 (s, 3H), 3.10 (s, 3H), 2.70 (s, 3H), 2.69 (s, 3H), 2.53-2.35 (m, 2H), 2.29-1.91 (m, 10H), 1.83-1.83 (m, 11H), 1.50-1.18 (m, 11H), 1.10-0.76 (m, 32H); ESI MS m/z 1263 [$C_{67}H_{111}N_{11}O_{12}$+H]$^+$; HPLC>99% (AUC), $t_R$=20.01 min.

Example 18

Preparation of 4-Methoxyphenyl Cyclosporin Alkyne

A mixture of cyclosporin alkyne from Example 3 (80 mg, 0.07 mmol), 1-iodo-4-methoxybenzene (150 μL, 1.4 mmol) and copper(I) iodide (13 mg, 0.07 mmol) in triethylamine (3 mL) was stirred until a clear solution formed. Dichlorobis(triphenylphosphine)palladium(II) (50 mg, 0.07 mmol) was added, and then the mixture was stirred at room temperature overnight. The reaction mixture was filtered through a micro-filter and concentrated under vacuum. The residue was purified by column chromatography (silica gel, 7:3 hexanes/ethyl acetate to ethyl acetate) to give a brown solid. The solid was further purified twice by semi-preparative HPLC to afford 4-methoxyphenyl cyclosporin alkyne (23 mg, 26%) as a white solid: $^1$H NMR (500 MHz, CDCl$_3$) δ 8.17 (d, J=9.7 Hz, 1H), 7.77 (d, J=7.4 Hz, 1H), 7.50 (d, J=8.5 Hz, 1H), 7.31 (d, J=8.8 Hz, 2H), 7.21 (d, J=7.9 Hz, 1H), 6.80 (d, J=8.8 Hz, 2H), 5.68 (dd, J=11.0, 4.3 Hz, 1H), 5.42 (d, J=7.1 Hz, 1H), 5.29 (dd, J=11.6, 3.9 Hz, 1H), 5.20-5.18 (m, 2H), 5.09-5.05 (m, 2H), 5.01 (dd, J=16.2, 8.1 Hz, 1H), 4.85 (app quintet, J=6.9 Hz, 1H), 4.73-4.69 (m, 2H), 4.51 (app quintet, J=7.2 Hz, 1H), 3.92 (d, J=6.4 Hz, 1H), 3.80 (s, 3H), 3.52 (s, 3H), 3.40 (s, 3H), 3.29 (s, 3H), 3.20-3.14 (m, 6H), 3.13 (s, 3H), 3.10 (s, 3H), 2.69 (s, 3H), 2.67 (s, 3H), 2.44-1.95 (m, 12H), 1.76-1.61 (m, 3H), 1.45-1.24 (m, 16H), 1.07 (t, J=8.0 Hz, 4H), 0.97-0.79 (m, 27H); ESI MS m/z 1293 [$C_{68}H_{113}N_{11}O_{13}$+H]$^+$; HPLC>99% (AUC), $t_R$=19.59 min.

Example 19

Preparation of 4-Fluorophenyl Cyclosporin Alkyne

A mixture of cyclosporin alkyne from Example 3 (80 mg, 0.07 mmol), 4-fluoro-1-iodobenzene (160 μL, 1.4 mmol) and copper(I) iodide (14 mg, 0.07 mmol) in triethylamine (3 mL) was stirred until a clear solution formed. Dichlorobis(triphenylphosphine)palladium(II) (50 mg, 0.07 mmol) was added, and then the mixture was stirred at room temperature overnight. The reaction mixture was filtered through a micro-filter and concentrated under vacuum. The residue was purified by column chromatography (silica gel, 7:3 hexanes/ethyl acetate to ethyl acetate) to give a brown solid. The solid was further purified twice by semi-preparative HPLC to afford 4-fluorophenyl cyclosporin alkyne (8.9 mg, 10%) as a white solid: $^1$H NMR (300 MHz, CDCl$_3$) δ 8.14 (d, J=9.8 Hz, 1H), 7.76 (d, J=7.4 Hz, 1H), 7.52 (d, J=8.4 Hz, 1H), 7.35 (ddd, J=8.7, 5.4, 2.0 Hz, 2H), 7.19 (d, J=7.9 Hz, 1H), 6.97 (dd, J=8.7, 8.7 Hz, 2H), 5.68 (dd, J=11.1, 4.1 Hz, 1H), 5.45 (d, J=6.7 Hz, 1H), 5.27 (dd, J=11.5, 3.7 Hz, 1H), 5.18-5.14 (m, 1H), 5.09-4.94 (m, 4H), 4.88-4.79 (m, 1H), 4.74-4.66 (m, 2H), 4.56-4.47 (m, 1H), 3.91 (t, J=6.4 Hz, 1H), 3.52 (s, 3H), 3.40 (s, 3H), 3.29 (s, 3H), 3.13 (s, 3H), 3.10 (s, 3H), 2.71 (s, 3H), 2.69 (s, 3H), 2.45-0.76 (m, 68H); ESI MS m/z 1280 [$C_{67}H_{110}FN_{11}O_{12}$+H]$^+$; HPLC>99% (AUC), $t_R$=20.18 min.

Example 20

Preparation of Thiophen-2-yl Cyclosporin Alkyne

A mixture of cyclosporin alkyne from Example 3 (80 mg, 0.07 mmol), 2-iodothiophene (328 mg, 1.4 mmol) and copper(I) iodide (13 mg, 0.07 mmol) in triethylamine (3 mL) was stirred until a clear solution formed. Dichlorobis(triphenylphosphine)palladium(II) (50 mg, 0.07 mmol) was added, and then the mixture was stirred at room temperature overnight. The reaction mixture was filtered through a micro-filter and concentrated under vacuum. The residue was purified by column chromatography (silica gel, 7:3 hexanes/ethyl acetate to ethyl acetate) to give a light brown solid. The solid was further purified twice by semi-preparative HPLC to afford thiophen-2-yl cyclosporin alkyne (10.7 mg, 12%) as a white solid: $^1$H NMR (500 MHz, CDCl$_3$) δ 8.07 (d, J=9.6 Hz, 1H), 7.74 (d, J=7.4 Hz, 1H), 7.54 (d, J=8.3 Hz, 1H), 7.25 (d, J=5.6 Hz, 1H), 7.15 (dd, J=5.2, 1.0 Hz, 1H), 7.11 (dd, J=3.5, 0.9 Hz, 1H), 6.92 (dd, J=5.1, 3.6 Hz, 1H), 5.69 (dd, J=11.0, 4.3 Hz, 1H), 5.47 (d, J=6.4 Hz, 1H), 5.29 (dd, J=11.4, 3.6 Hz, 1H), 5.18-5.16 (m, 1H), 5.07 (t, J=6.9 Hz, 1H), 5.05-5.00 (m, 2H), 4.86-4.81 (m, 1H), 4.74-4.67 (m, 2H), 4.57-4.51 (m, 1H), 3.90 (t, J=6.4 Hz, 1H), 3.52 (s, 3H), 3.39 (s, 3H), 3.28 (s, 3H), 3.25-3.15 (m, 3H), 3.12 (s, 3H), 3.10 (s, 3H), 3.07-2.90 (m, 4H), 2.82-2.75 (m, 1H), 2.72 (s, 3H), 2.70 (s, 3H), 2.44-1.90 (m, 8H), 1.79-1.58 (m, 6H), 1.48-1.18 (m, 11H), 1.05-0.80 (m, 36H); ESI MS m/z 1269 [$C_{65}H_{109}N_{11}O_{12}S$+H]$^+$; HPLC 98.8% (AUC), $t_R$=19.76 min.

Example 21

Preparation of the Acetate of Cyclosporin Diyne

To a solution of the acetate of cyclosporin alkyne from Example 6 (90 mg, 0.073 mmol) in pyrrolidine (1 mL) were added copper(I) iodide (7 mg, 0.037 mmol) and dichlorobis(triphenylphosphine)palladium(II) (26 mg, 0.037 mmol), then the mixture was stirred for 5 min at room temperature. 1-Butynyl iodide (145 μL, 1.46 mmol) was added dropwise, and then the mixture was stirred overnight at room temperature. The reaction mixture was diluted with ethyl acetate (40 mL) and washed with a saturated solution of ammonium chloride (20 mL). The aqueous layer was extracted with ethyl acetate (2×20 mL). The combined organics were dried over anhydrous sodium sulfate and concentrated under vacuum. The crude material was purified by semi-preparative HPLC to afford the desired acetate of cyclosporin diyne (15 mg, 16%) as a brown solid: $^1$H NMR (300 MHz, CDCl$_3$) δ 8.48 (d, J=9.6 Hz, 1H), 8.05 (d, J=6.9 Hz, 1H), 7.60 (d, J=9.0 Hz, 1H), 7.55 (d, J=7.8 Hz, 1H), 5.70 (dd, J=10.8, 3.9

Hz, 1H), 5.58-5.35 (m, 2H), 5.30 (dd, J=12.0, 3.3 Hz, 2H), 5.15 (t, J=6.9 Hz, 1H), 5.05-4.80 (m, 3H), 4.73 (t, J=9.6 Hz, 1H), 4.64 (d, J=13.8 Hz, 1H), 4.44 (t, J=6.9 Hz, 1H), 3.43 (s, 3H), 3.32 (s, 3H), 3.27 (s, 3H), 3.20 (s, 3H), 3.07 (s, 3H), 2.68 (s, 3H), 2.66 (s, 3H), 2.50-2.35 (m, 1H), 2.30-1.80 (m, 10H), 2.04 (s, 3H), 1.75-1.55 (m, 3H), 1.45-0.75 (m, 59H); ESI MS m/z 1281 $[C_{67}H_{113}N_{11}O_{13}+H]^+$.

Example 22

Preparation of Cyclosporin Diyne

To a solution of the acetate of cyclosporin diyne from Example 21 (18 mg, 0.014 mmol) in MeOH (2 mL) was added potassium carbonate (39 mg, 0.28 mmol), then the mixture was stirred overnight at room temperature. The reaction mixture was quenched with a saturated solution of ammonium chloride, and then extracted with ethyl acetate (3×30 mL). The combined organics were dried over anhydrous sodium sulfate and concentrated under vacuum. The crude material was purified by semi-preparative HPLC to afford cyclosporin diyne (9 mg, 53%) as a white solid: $^1$H NMR (300 MHz, CDCl$_3$) δ 7.98 (d, J=9.3 Hz, 1H), 7.73 (d, J=7.2 Hz, 1H), 7.39 (d, J=8.4 Hz, 1H), 7.23 (d, J=8.1 Hz, 1H), 5.71 (dd, J=10.8, 3.9 Hz, 1H), 5.41 (d, J=6.6 Hz, 1H), 5.28 (dd, J=11.7, 3.9 Hz, 1H), 5.20-4.95 (m, 5H), 4.83 (t, J=7.2 Hz, 1H), 4.78-4.63 (m, 2H), 4.52 (t, J=7.2 Hz, 1H), 3.90 (t, J=6.3 Hz, 1H), 3.50 (s, 3H), 3.37 (s, 3H), 3.28 (s, 3H), 3.12 (s, 3H), 3.09 (s, 3H), 2.72 (s, 3H), 2.70 (s, 3H), 2.55-2.05 (m, 7H), 1.90-0.80 (m, 66H); ESI MS m/z 1238 $[C_{65}H_{111}N_{11}O_{12}+H]^+$; HPLC>99% (AUC), $t_R$=20.06 min.

Example 23

Preparation of the Acetate of Cyclosporin Alkynyl Bromide

To a solution of the acetate of cyclosporin alkyne from Example 6 (0.22 g, 0.18 mmol) in acetone (5 mL) was added N-bromosuccinimide (64 mg, 0.36 mmol) followed by silver nitrate (6 mg, 0.036 mmol). The reaction flask was wrapped with aluminum foil. The reaction mixture was stirred at room temperature for 1 h, then poured into ice-water (20 mL) and extracted with ethyl ether (3×40 mL). The combined organics were washed with brine (30 mL), dried over anhydrous sodium sulfate and concentrated under vacuum. The crude material was purified by semi-preparative HPLC to afford the acetate of cyclosporin alkynyl bromide (0.23 g, 98%) as a white solid: $^1$H NMR (300 MHz, CDCl$_3$) δ 8.48 (d, J=9.6 Hz, 1H), 8.07 (d, J=6.9 Hz, 1H), 7.80 (d, J=8.9 Hz, 1H), 7.63 (d, J=7.7 Hz, 1H), 5.70 (dd, J=10.8, 3.6 Hz, 1H), 5.60-5.15 (m, 5H), 5.02-4.80 (m, 4H), 4.76 (d, J=9.3 Hz, 1H), 4.65 (d, J=13.9 Hz, 1H), 4.48 (t, J=7.0 Hz, 1H), 3.43 (s, 3H), 3.30 (s, 3H), 3.25 (s, 3H), 3.19 (s, 3H), 3.10 (s, 3H), 2.69 (s, 3H), 2.68 (s, 3H), 2.45-2.35 (m, 1H), 2.30-2.05 (m, 7H), 2.02 (s, 3H), 1.75-1.55 (m, 4H), 1.45-0.75 (m, 55H); ESI MS m/z 1307 $[C_{63}H_{108}BrN_{11}O_{13}+H]^+$.

Example 24

Preparation of the Acetate of Cyclosporin(trimethylsilyl)diyne

To a solution of the acetate of cyclosporin alkynyl bromide from Example 23 (20 mg, 0.015 mmol) in pyrrolidine (1 mL) was added (trimethylsilyl)acetylene (42 µL, 0.30 mmol) followed by copper(I) iodide (3 mg, 0.015 mmol) and dichlorobis(triphenylphosphine)palladium(II) (6 mg, 0.008 mmol), then the mixture was stirred at room temperature for 1 h. The reaction was quenched with a saturated solution of ammonium chloride, and then extracted with ethyl acetate (3×30 mL). The combined organics were dried over anhydrous sodium sulfate and concentrated under vacuum. The crude material was purified by semi-preparative HPLC to afford the acetate of cyclosporin (trimethylsilyl)diyne (6 mg, 30%) as a pale-brown solid: $^1$H NMR (300 MHz, CDCl$_3$) δ 8.48 (d, J=9.6 Hz, 1H), 8.05 (d, J=6.7 Hz, 1H), 7.65 (d, J=8.8 Hz, 1H), 7.57 (d, J=7.9 Hz, 1H), 5.70 (dd, J=11.2, 3.8 Hz, 1H), 5.55-5.35 (m, 2H), 5.29 (td, J=11.9, 3.7 Hz, 2H), 5.16 (d, J=6.1 Hz, 1H), 5.03-4.80 (m, 3H), 4.72 (t, J=9.4 Hz, 1H), 4.63 (d, J=13.9 Hz, 1H), 4.46 (t, J=7.0 Hz, 1H), 3.42 (s, 3H), 3.32 (s, 3H), 3.27 (s, 3H), 3.20 (s, 3H), 3.08 (s, 3H), 2.68 (s, 3H), 2.67 (s, 3H), 2.45-2.05 (m, 7H), 2.04 (s, 3H), 1.75-1.55 (m, 3H), 1.45-0.75 (m, 56H), 0.15 (s, 9H); ESI MS m/z 1325 $[C_{68}H_{117}N_{11}O_{13}Si+H]^+$.

Example 25

Preparation of Cyclosporin Diyne

To a solution of the acetate of cyclosporin (trimethylsilyl) diyne from Example 24 (9 mg, 0.007 mmol) in MeOH (2 mL) was added potassium carbonate (19 mg, 0.14 mmol), then the mixture was stirred overnight at room temperature. The reaction mixture was quenched with a saturated solution of ammonium chloride, and then extracted with ethyl acetate (3×30 mL). The combined organics were dried over anhydrous sodium sulfate and concentrated under vacuum. The crude material was purified by semi-preparative HPLC to afford cyclosporine diyne (6 mg, 71%) as a white solid: $^1$H NMR (300 MHz, CDCl$_3$) δ 7.95 (d, J=9.7 Hz, 1H), 7.65 (d, J=7.4 Hz, 1H), 7.38 (d, J=8.3 Hz, 1H), 7.17 (d, J=7.9 Hz, 1H), 5.71 (dd, J=10.8, 3.8 Hz, 1H), 5.48 (d, J=6.2 Hz, 1H), 5.27 (dd, J=11.5, 3.9 Hz, 1H), 5.15-4.95 (m, 5H), 4.83 (t, J=7.1 Hz, 1H), 4.75-4.62 (m, 2H), 4.53 (t, J=7.2 Hz, 1H), 3.89 (t, J=6.2 Hz, 1H), 3.51 (s, 3H), 3.38 (s, 3H), 3.28 (s, 3H), 3.11 (s, 3H), 3.10 (s, 3H), 2.70 (s, 3H), 2.69 (s, 3H), 2.60-2.35 (m, 2H), 2.20-0.80 (m, 67H); ESI MS m/z 1211 $[C_{63}H_{107}N_{11}O_{12}+H]^+$; HPLC 98.5% (AUC), $t_R$=18.78 min.

Example 26

Preparation of the Acetate of Cyclosporin Diyne

To an ice-cooled solution of 1-propynylmagnesium bromide (0.54 mL, 0.5 M in THF, 0.27 mmol) in THF (1 mL) was added a solution of zinc chloride (0.27 mL, 1 M in ethyl ether, 0.27 mmol). The reaction was stirred at 0° C. for 10 min, and then allowed to warm to room temperature. A solution of the acetate of cyclosporin alkynyl bromide from Example 23 (35 mg, 0.027 mmol) in THF (1 mL) was added into the reaction mixture followed by dichlorobis(triphenylphosphine)palladium(II) (10 mg, 0.014 mmol). The resulting reaction mixture was stirred at room temperature for 1.5 h, and then quenched with a saturated solution of ammonium chloride (10 mL). The aqueous layer was extracted with ethyl acetate (3×20 mL). The combined organics were dried over anhydrous sodium sulfate and concentrated under vacuum. The crude material was purified by semi-preparative HPLC to afford the acetate of cyclosporin diyne (14 mg, 41%) as a pale-brown solid: $^1$H NMR (500 MHz, CDCl$_3$) δ 8.42 (d, J=9.5 Hz, 1H), 8.07 (d, J=7.0 Hz, 1H), 7.82 (d, J=9.0 Hz, 1H), 7.64 (d, J=7.5 Hz, 1H), 5.71 (dd, J=11.0, 4.5 Hz, 1H), 5.58-5.37 (m, 3H), 5.27

(dd, J=12.0, 4.0 Hz, 1H), 5.17 (t, J=6.0 Hz, 1H), 5.03-4.93 (m, 3H), 4.87 (t, J=7.0 Hz, 1H), 4.81 (t, J=9.5 Hz, 1H), 4.65 (d, J=13.5 Hz, 1H), 4.49 (t, J=7.0 Hz, 1H), 3.43 (s, 3H), 3.29 (s, 3H), 3.23 (s, 3H), 3.19 (s, 3H), 3.09 (s, 3H), 2.70 (s, 3H), 2.68 (s, 3H), 2.45-2.35 (m, 1H), 2.28-2.04 (m, 7H), 2.03 (s, 3H), 2.02-1.92 (m, 2H), 1.88 (s, 3H), 1.75-1.62 (m, 4H), 1.45-0.75 (m, 53H); ESI MS m/z 1267 $[C_{66}H_{111}N_{11}O_{13}+H]^+$.

Example 27

Preparation of Cyclosporin Diyne

To a solution of the acetate of cyclosporin diyne from Example 26 (14 mg, 0.011 mmol) in MeOH (2 mL) was added potassium carbonate (30 mg, 0.22 mmol), then the mixture was stirred overnight at room temperature. The reaction mixture was quenched with a saturated solution of ammonium chloride, and then extracted with ethyl acetate (3×30 mL). The combined organics were dried over anhydrous sodium sulfate and concentrated under vacuum. The crude material was purified by semi-preparative HPLC to afford cyclosporin diyne (8 mg, 62%) as a white solid: $^1$H NMR (300 MHz, CDCl$_3$) δ 7.93 (d, J=9.5 Hz, 1H), 7.71 (d, J=7.0 Hz, 1H), 7.51 (d, J=8.2 Hz, 1H), 7.37 (d, J=7.4 Hz, 1H), 5.71 (dd, J=11.0, 2.9 Hz, 1H), 5.41 (d, J=6.5 Hz, 1H), 5.38-5.27 (m, 1H), 5.15-4.95 (m, 4H), 4.84 (t, J=7.0 Hz, 1H), 4.75-4.65 (m, 2H), 4.54 (t, J=6.9 Hz, 1H), 3.94 (t, J=6.5 Hz, 1H), 3.48 (s, 3H), 3.37 (s, 3H), 3.25 (s, 3H), 3.12 (s, 3H), 3.10 (s, 3H), 2.72 (s, 3H), 2.71 (s, 3H), 2.55-2.05 (m, 7H), 1.88 (s, 3H), 1.75-0.75 (m, 62H); ESI MS m/z 1225 $[C_{64}H_{109}N_{11}O_{12}+H]^+$; HPLC>99% (AUC), $t_R$=19.38 min.

Example 28

Preparation of the Acetate of Cyclosporin Cyclopropyl Diyne

To an ice-cooled solution of cyclopropyl(trimethylsilyl)acetylene (37 mg, 0.27 mmol) in triethylamine (1 mL) was added tetrabutylammonium fluoride (0.32 mL, 1 M in THF, 0.32 mmol), then the mixture was stirred for 10 min. The reaction mixture was allowed to warm to room temperature, then a solution of the acetate of cyclosporin alkynyl bromide from Example 23 (35 mg, 0.027 mmol) in triethylamine (1 mL) was added into the mixture followed by copper(I) iodide (3 mg, 0.014 mmol) and dichlorobis(triphenylphosphine)palladium(II) (10 mg, 0.014 mmol). The resulting reaction mixture was stirred at room temperature for 5 h. The reaction mixture was diluted with ethyl acetate (30 mL) and washed with a saturated solution of ammonium chloride (10 mL). The aqueous layer was extracted with ethyl acetate (2×20 mL). The combined organics were dried over anhydrous sodium sulfate and concentrated under vacuum. The crude material was purified by semi-preparative HPLC to afford the acetate of cyclosporin cyclopropyl diyne (23 mg, 66%) as a pale-brown solid: $^1$H NMR (300 MHz, CDCl$_3$) δ 8.45 (d, J=9.4 Hz, 1H), 8.05 (d, J=6.8 Hz, 1H), 7.71 (d, J=9.0 Hz, 1H), 7.60 (d, J=7.8 Hz, 1H), 5.70 (dd, J=10.9, 3.6 Hz, 1H), 5.58-5.23 (m, 4H), 5.16 (d, J=5.5 Hz, 1H), 5.02-4.80 (m, 3H), 4.77 (t, J=9.6 Hz, 1H), 4.64 (d, J=13.9 Hz, 1H), 4.46 (t, J=7.0 Hz, 1H), 3.43 (s, 3H), 3.30 (s, 3H), 3.25 (s, 3H), 3.19 (s, 3H), 3.08 (s, 3H), 2.69 (s, 3H), 2.67 (s, 3H), 2.45-2.35 (m, 1H), 2.30-2.03 (m, 6H), 2.02 (s, 3H), 1.75-1.60 (m, 3H), 1.45-0.70 (m, 63H); ESI MS m/z 1293 $[C_{68}H_{113}N_{11}O_{13}+H]^+$.

Example 29

Preparation of Cyclosporin Cyclopropyl Diyne

To a solution of the acetate of cyclosporin cyclopropyl diyne from Example 28 (20 mg, 0.015 mmol) in MeOH (2 mL) was added potassium carbonate (41 mg, 0.30 mmol), then the mixture was stirred overnight at room temperature. The reaction mixture was quenched with a saturated solution of ammonium chloride, and then extracted with ethyl acetate (3×30 mL). The combined organics were dried over anhydrous sodium sulfate and concentrated under vacuum. The crude material was purified by semi-preparative HPLC to afford cyclosporin cyclopropyl diyne (16 mg, 84%) as a white solid: $^1$H NMR (300 MHz, CDCl$_3$) δ 7.97 (d, J=9.7 Hz, 1H), 7.70 (d, J=7.3 Hz, 1H), 7.40 (d, J=8.4 Hz, 1H), 7.25 (d, J=8.7 Hz, 1H), 5.71 (dd, J=1.0, 4.0 Hz, 1H), 5.41 (d, J=6.6 Hz, 1H), 5.28 (dd, J=11.4, 3.9 Hz, 1H), 5.15-4.95 (m, 4H), 4.83 (t, J=7.2 Hz, 1H), 4.75-4.65 (m, 3H), 4.52 (t, J=7.2 Hz, 1H), 3.90 (t, J=6.4 Hz, 1H), 3.49 (s, 3H), 3.37 (s, 3H), 3.28 (s, 3H), 3.12 (s, 3H), 3.09 (s, 3H), 2.71 (s, 3H), 2.70 (s, 3H), 2.55-2.30 (m, 2H), 2.20-0.75 (m, 71H); ESI MS m/z 1251 $[C_{66}H_{111}N_{11}O_{12}+H]^+$; HPLC>99% (AUC), $t_R$=19.98 min.

Example 30

Preparation of the Acetate of Cyclosporin Diyne

A mixture of the acetate of cyclosporine alkynyl bromide from Example 23 (40 mg, 0.03 mmol), dichlorobis(triphenylphosphine)palladium(II) (14 mg, 0.02 mmol), copper(I) iodide (4 mg, 0.02 mmol) and phenylacetylene (30 μL, 0.30 mmol) in triethylamine (2 mL) was stirred at room temperature overnight. The reaction mixture was filtered through a micro-filter and concentrated under vacuum. Purification by column chromatography (silica gel, 100% hexanes followed by 100% EtOAc) followed by semi-preparative HPLC gave the acetate of cyclosporin diyne (11 mg, 27%) as a brown solid: $^1$H NMR (300 MHz, CDCl$_3$) δ 8.52 (d, J=9.7 Hz, 1H), 8.05 (d, J=6.9 Hz, 1H), 7.62-7.54 (m, 2H), 7.47-7.44 (m, 2H), 7.34-7.28 (m, 3H), 5.69 (dd, J=10.9, 3.9 Hz, 1H), 5.59-5.50 (m, 1H), 5.47-5.43 (m, 1H), 5.35 (t, J=3.5 Hz, 1H), 5.31 (t, J=3.4 Hz, 1H), 5.15 (t, J=6.2 Hz, 1H), 5.02-4.91 (m, 4H), 4.86 (t, J=7.2 Hz, 1H), 4.75 (t, J=9.6 Hz, 1H), 4.67-4.63 (m, 1H), 4.45 (t, J=7.0 Hz, 1H), 3.44 (s, 3H), 3.42 (s, 3H), 3.28 (s, 3H), 3.20 (s, 3H), 3.08 (s, 3H), 2.69 (s, 3H), 2.66 (s, 3H), 2.52-2.11 (m, 8H), 2.07 (s, 3H), 1.75-1.55 (m, 4H), 1.41-1.18 (m, 20H), 1.05-0.82 (m, 34H); ESI MS m/z 1329 $[C_{71}H_{113}N_{11}O_{13}+H]^+$.

Example 31

Preparation of Cyclosporin Diyne

To a solution of the acetate of cyclosporin diyne from Example 30 (11 mg, 0.008 mmol) in MeOH (1 mL) was added potassium carbonate (11 mg, 0.08 mmol) and then the mixture was stirred at room temperature overnight. The mixture was diluted with EtOAc, washed with H$_2$O (2×), brine, dried over Na$_2$SO$_4$, and concentrated. Purification by semi-preparative HPLC gave the cyclosporin diyne (6.6 mg, 64%) as a brown solid: $^1$H NMR (300 MHz, CDCl$_3$) δ 7.98 (d, J=9.7 Hz, 1H), 7.69 (d, J=7.5 Hz, 1H), 7.50-7.47 (m, 2H), 7.41 (d, J=8.3 Hz, 1H), 7.32-7.28 (m, 3H), 7.22 (d, J=7.9 Hz, 1H), 5.70 (dd, J=11.0, 4.1 Hz, 1H), 5.48 (d, J=6.4 Hz, 1H), 5.34-5.29 (m, 2H), 5.15-4.99 (m, 6H), 4.83 (t, J=7.0 Hz, 1H), 4.74-4.66 (m, 2H), 4.52 (t, J=7.3 Hz, 1H), 3.93 (t, J=6.3 Hz, 1H), 3.52 (s, 3H), 3.39 (s, 3H), 3.26 (s, 3H), 3.24-3.17 (m, 3H), 3.11 (s, 3H), 2.71 (s, 3H), 2.70 (s, 3H), 2.31-2.06 (m, 12H), 1.67-1.62 (m, 4H), 1.55-1.21 (m, 12H), 1.07-0.84 (m, 38H); ESI MS m/z 1287 $[C_{69}H_{111}N_{11}O_{12}+H]^+$; HPLC 96.6% (AUC), $t_R$=20.88 min.

Example 32

Preparation of the Acetate of Cyclosporin yne-yne-ene

To an ice-cooled solution of the acetate of cyclosporin (trimethylsilyl)diyne from Example 24 (25 mg, 0.019 mmol) in triethylamine (1 mL) was added tetrabutylammonium fluoride (95 μL, 1 M in THF, 0.095 mmol), then the mixture was stirred for 10 min. The reaction mixture was allowed to warm to room temperature, then copper(I) iodide (4 mg, 0.019 mmol) and dichlorobis(triphenylphosphine)palladium (II) (13 mg, 0.019 mmol) were added into the mixture followed by vinyl iodide (30 μL, 0.38 mmol). The resulting reaction mixture was stirred at room temperature for 1 h. The reaction mixture was filtered through a micro-filter and concentrated under vacuum. The crude material was purified by semi-preparative HPLC to afford the desired acetate of cyclosporin yne-yne-ene (6 mg, 25%) as a brown oil: $^1$H NMR (300 MHz, CDCl$_3$) δ 8.43 (d, J=9.5 Hz, 1H), 8.07 (d, J=6.7 Hz, 1H), 7.82 (d, J=8.9 Hz, 1H), 7.64 (d, J=7.7 Hz, 1H), 5.80-5.65 (m, 4H), 5.60-5.52 (m, 3H), 5.45-5.33 (m, 2H), 5.28(dd, J=11.9, 3.6 Hz, 1H), 5.17 (t, J=7.7 Hz, 1H), 5.02-4.91 (m, 4H), 4.86 (t, J=7.4 Hz, 1H), 4.79 (t, J=9.4 Hz, 1H), 4.65 (d, J=14.0 Hz, 1H), 4.49 (d, J=7.0 Hz, 1H), 3.43 (s, 3H), 3.30 (s, 3H), 3.24 (s, 3H), 3.19 (s, 3H), 3.09 (s, 3H), 2.70 (s, 3H), 2.68 (s, 3H), 2.45-2.35 (m, 1H), 2.30-2.05 (m, 4H), 2.04 (s, 3H), 1.98-1.83 (m, 2H), 1.72-1.60 (m, 3H), 1.45-0.75 (m, 54H); ESI MS m/z 1279 $[C_{67}H_{111}N_{11}O_{13}+H]^+$.

Example 33

Preparation of Cyclosporin yne-yne-ene

To a solution of the acetate of cyclosporin yne-yne-ene from Example 32 (14 mg, 0.011 mmol) in MeOH (2 mL) was added potassium carbonate (30 mg, 0.22 mmol), then the mixture was stirred at room temperature for 12 h. The reaction mixture was diluted with ethyl acetate (30 mL), then washed with a saturated solution of ammonium chloride (15 mL). The aqueous layer was separated and extracted with ethyl acetate (2×20 mL). The combined organics were dried over anhydrous sodium sulfate and concentrated under vacuum. The crude material was purified by semi-preparative HPLC to afford cyclosporin yne-yne-ene (10 mg, 72%) as a white solid: $^1$H NMR (500 MHz, CDCl$_3$) δ 7.94 (d, J=10.0 Hz, 1H), 7.65 (d, J=7.5 Hz, 1H), 7.36 (d, J=8.5 Hz, 1H), 7.20 (d, J=8.0 Hz, 1H), 5.85-5.67 (m, 3H), 5.57 (dd, J=10.5, 3.0 Hz, 1H), 5.46 (d, J=7.0 Hz, 1H), 5.29 (dd, J=11.5, 4.0 Hz, 1H), 5.12 (d, J=10.5 Hz, 1H), 5.08 (t, J=7.0 Hz, 1H), 5.05-4.95 (m, 2H), 4.83 (t, J=7.0 Hz, 1H), 4.74-4.64 (m, 2H), 4.52 (t, J=7.5 Hz, 1H), 3.93 (t, J=6.5 Hz, 1H), 3.51 (s, 3H), 3.38 (s, 3H), 3.27 (s, 3H), 3.11 (s, 3H), 3.09 (s, 3H), 2.71 (s, 3H), 2.69 (s, 3H), 2.61 (dd, J=17.5, 4.0 Hz, 1H), 2.45-2.35 (m, 1H), 2.26 (dd, J=17.5, 7.5 Hz, 1H), 2.20-2.07 (m, 5H), 2.03-1.88 (m, 3H), 1.82-1.60 (m, 5H), 1.50-0.80 (m, 53H); ESI MS m/z 1237 $[C_{65}H_{109}N_{11}O_{12}+H]^+$; HPLC>99% (AUC), $t_R$=19.98 min.

Example 34

Preparation of the Acetate of cis-Cyclosporin yne-yne-ene

To an ice-cooled solution of the acetate of cyclosporin (trimethylsilyl)diyne from Example 24 (53 mg, 0.040 mmol) in triethylamine (1 mL) was added tetrabutylammonium fluoride (0.20 mL, 1 M in THF, 0.20 mmol), then the mixture was stirred for 10 min. The reaction mixture was allowed to warm to room temperature, then copper(I) iodide (4 mg, 0.02 mmol) and dichlorobis(triphenylphosphine)palladium (II) (14 mg, 0.02 mmol) were added into the mixture followed by cis-1-bromo-1-propene (68 μL, 0.80 mmol). The resulting reaction mixture was stirred at room temperature for 1 h. The reaction mixture was filtered through a micro-filter and concentrated under vacuum. The crude material was purified by semi-preparative HPLC to afford the desired acetate of cis-cyclosporin yne-yne-ene (19 mg, 37%) as a pale-brown solid: $^1$H NMR (300 MHz, CDCl$_3$) δ 8.50 (d, J=9.7 Hz, 1H), 8.06 (d, J=6.8 Hz, 1H), 7.67 (d, J=8.9 Hz, 1H), 7.58 (d, J=7.8 Hz, 1H), 6.15-6.03 (m, 1H), 5.70 (dd, J=11.0, 3.8 Hz, 1H), 5.58-5.40 (m, 3H), 5.31 (dd, J=11.9, 3.6 Hz, 2H), 5.15 (t, J=7.2 Hz, 1H), 5.04-4.82 (m, 3H), 4.74 (t, J=10.5 Hz, 1H), 4.65 (d, J=13.9 Hz, 1H), 4.46 (t, J=7.0 Hz, 1H), 3.43 (s, 3H), 3.32 (s, 3H), 3.27 (s, 3H), 3.20 (s, 3H), 3.08 (s, 3H), 2.69 (s, 3H), 2.67 (s, 3H), 2.50-2.09 (m, 6H), 2.05 (s, 3H), 1.98-1.83 (m, 4H), 1.72-1.60 (m, 3H), 1.45-0.75 (m, 58H); ESI MS m/z 1293 $[C_{68}H_{113}N_{11}O_{13}+H]^+$.

Example 35

Preparation of cis-Cyclosporin yne-yne-ene

To a solution of the acetate of cis-cyclosporin yne-yne-ene from Example 34 (19 mg, 0.015 mmol) in MeOH (2 mL) was added potassium carbonate (41 mg, 0.30 mmol), then the mixture was stirred at room temperature for 6 h. The reaction mixture was diluted with ethyl acetate (40 mL), then washed with a saturated solution of ammonium chloride (20 mL). The aqueous layer was separated and extracted with ethyl acetate (2×30 mL). The combined organics were dried over anhydrous sodium sulfate and concentrated under vacuum. The crude material was purified by semi-preparative HPLC to afford cis-cyclosporin yne-yne-ene (10 mg, 53%) as a white solid: $^1$H NMR (300 MHz, CDCl$_3$) δ 7.97 (d, J=9.6 Hz, 1H), 7.70 (d, J=7.3 Hz, 1H), 7.42 (d, J=8.2 Hz, 1H), 7.25 (overlapped with CHCl$_3$, 1H), 6.15-6.04 (m, 1H), 5.71 (dd, J=11.1, 3.9 Hz, 1H), 5.52-5.40 (m, 2H), 5.29 (dd, J=11.5, 3.8 Hz, 1H), 5.15-4.95 (m, 5H), 4.83 (t, J=7.2 Hz, 1H), 4.76-4.63 (m, 2H), 4.52 (t, J=7.1 Hz, 1H), 3.91 (t, J=6.4 Hz, 1H), 3.51 (s, 3H), 3.38 (s, 3H), 3.27 (s, 3H), 3.12 (s, 3H), 3.10 (s, 3H), 2.72 (s, 3H), 2.70 (s, 3H), 2.61 (dd, J=17.5, 3.8 Hz, 1H), 2.50-1.85 (m, 7H), 1.80-0.78 (m, 63H); ESI MS m/z 1251 $[C_{66}H_{111}N_{11}O_{12}+H]^+$; HPLC>99% (AUC), $t_R$=20.59 min.

Example 36

Preparation of the Acetate of trans-Cyclosporin yne-yne-ene

To an ice-cooled solution of the acetate of cyclosporin (trimethylsilyl)diyne from Example 24 (60 mg, 0.045 mmol) in triethylamine (1 mL) was added tetrabutylammonium fluoride (0.23 mL, 1 M in THF, 0.23 mmol), then the mixture was stirred for 10 min. The reaction mixture was allowed to warm to room temperature, then copper(I) iodide (4 mg, 0.02 mmol) and dichlorobis(triphenylphosphine)palladium (II) (16 mg, 0.02 mmol) were added into the mixture followed by trans-1-bromo-1-propene (77 µL, 0.90 mmol). The resulting reaction mixture was stirred at room temperature for 1 h. The reaction mixture was filtered through a micro-filter and concentrated under vacuum. The crude material was purified by semi-preparative HPLC to afford the desired acetate of trans-cyclosporin yne-yne-ene (26 mg, 45%) as a pale-brown solid: $^1$H NMR (300 MHz, CDCl$_3$) δ 8.45 (d, J=9.3 Hz, 1H), 8.08 (d, J=6.6 Hz, 1H), 7.82 (d, J=8.7 Hz, 1H), 7.64 (d, J=7.8 Hz, 1H), 6.35-6.18 (m, 1H), 5.70 (dd, J=11.1, 3.9 Hz, 1H), 5.60-5.35 (m, 5H), 5.28 (dd, J=12.0, 3.3 Hz, 1H), 5.17 (t, J=6.3 Hz, 1H), 5.04-4.75 (m, 5H), 4.65 (d, J=13.8 Hz, 1H), 4.49 (t, J=7.2 Hz, 1H), 3.43 (s, 3H), 3.30 (s, 3H), 3.24 (s, 3H), 3.19 (s, 3H), 3.09 (s, 3H), 2.70 (s, 3H), 2.68 (s, 3H), 2.45-2.35 (m, 1H), 2.30-1.85 (m, 10H), 2.03 (s, 3H), 1.80 (dd, J=6.9, 1.5 Hz, 3H), 1.75-1.58 (m, 3H), 1.45-0.75 (m, 52H); ESI MS m/z 1292 [C$_{68}$H$_{113}$N$_{11}$O$_{13}$+H]$^+$.

Example 37

Preparation of trans-Cyclosporin yne-yne-ene

To a solution of the acetate of trans-cyclosporin yne-yne-ene from Example 36 (25 mg, 0.019 mmol) in MeOH (3 mL) was added potassium carbonate (52 mg, 0.38 mmol), then the mixture was stirred at room temperature for 12 h. The reaction mixture was diluted with ethyl acetate (40 mL), then washed with a saturated solution of ammonium chloride (20 mL). The aqueous layer was separated and extracted with ethyl acetate (2×30 mL). The combined organics were dried over anhydrous sodium sulfate and concentrated under vacuum. The crude material was purified by semi-preparative HPLC to afford the trans-cyclosporin yne-yne-ene (15 mg, 63%) as a white solid: $^1$H NMR (300 MHz, CDCl$_3$) δ 7.95 (d, J=9.6 Hz, 1H), 7.69 (d, J=7.2 Hz, 1H), 7.37 (d, J=8.4 Hz, 1H), 7.21 (d, J=7.8 Hz, 1H), 6.35-6.20 (m, 1H), 5.71 (dd, J=11.4, 4.2 Hz, 1H), 5.55-5.40 (m, 2H), 5.29 (dd, J=11.4, 4.2 Hz, 1H), 5.18-4.95 (m, 4H), 4.83 (t, J=7.2 Hz, 1H), 4.76-4.63 (m, 2H), 4.52 (t, J=7.2 Hz, 1H), 3.91 (t, J=6.3 Hz, 1H), 3.50 (s, 3H), 3.38 (s, 3H), 3.27 (s, 3H), 3.12 (s, 3H), 3.09 (s, 3H), 2.71 (s, 3H), 2.70 (s, 3H), 2.61 (dd, J=17.4, 3.9 Hz, 1H), 2.45-1.85 (m, 7H), 1.80 (dd, J=6.6, 1.5 Hz, 3H), 1.75-0.78 (m, 61H); ESI MS m/z 1250 [C$_{66}$H$_{111}$N$_{11}$O$_{12}$+H]$^+$; HPLC>99% (AUC), t$_R$=20.28 min.

Example 38

Preparation of Cyclosporin Alkyne

A suspension of cyclosporin alkyne from Example 3 (50 mg, 0.04 mmol), cesium carbonate (325 mg, 1.0 mmol), sodium iodide (150 mg, 1.0 mmol) and copper(I) iodide (190 mg, 1.0 mmol) in DMF (2 mL) was stirred at room temperature for 30 min. Allyl bromide (70 µL, 0.80 mmol) was added dropwise and the resulting mixture was stirred at room temperature overnight. The blue suspension was diluted with Et$_2$O and filtered. The filtrate was washed twice with H$_2$O. The combined aqueous layers were extracted with Et$_2$O. The combined organics were washed with brine, dried over Na$_2$SO$_4$, and concentrated. Purification by semi-preparative HPLC gave cyclosporin alkyne (25 mg, 52%) as an off-white solid: $^1$H NMR (300 MHz, CDCl$_3$) δ 8.13 (d, J=9.5 Hz, 1H), 7.78 (d, J=7.3 Hz, 1H), 7.48 (d, J=8.4 Hz, 1H), 7.24 (d, J=10.3 Hz, 1H), 5.84-5.75 (m, 1H), 5.69 (dd, J=11.0, 4.2 Hz, 1H), 5.38-4.96 (m, 10H), 4.84 (t, J=7.1 Hz, 1H), 4.74-4.67 (m, 2H), 4.51 (t, J=7.3 Hz, 1H), 3.88 (t, J=6.6 Hz, 1H), 3.49 (s, 3H), 3.37 (s, 3H), 3.27 (s, 3H), 3.14 (s, 3H), 3.09 (s, 3H), 2.93-2.70 (m, 3H), 2.72 (s, 3H), 2.70 (s, 3H), 2.15-1.99 (m, 7H), 1.90-1.57 (m, 6H), 1.43-1.28 (m, 13H), 1.06-0.82 (m, 40H); ESI MS m/z 1227 [C$_{64}$H$_{111}$N$_{11}$O$_{12}$+H]$^+$; HPLC>99% (AUC), t$_R$=19.59 min.

Example 39

Preparation of Cyclosporin Alkyne

A suspension of cyclosporin alkyne from Example 3 (50 mg, 0.04 mmol), cesium carbonate (326 mg, 1.0 mmol), sodium iodide (152 mg, 1.0 mmol) and copper(I) iodide (190 mg, 1.0 mmol) in DMF (2 mL) was stirred at room temperature for 30 min. Benzyl bromide (100 µL, 0.8 mmol) was added dropwise and the resulting mixture was stirred at room temperature overnight. The blue suspension was diluted with Et$_2$O and filtered. The filtrate was washed twice with H$_2$O. The combined aqueous layers were extracted with Et$_2$O. The combined organics were washed with brine, dried over Na$_2$SO$_4$, and concentrated. Purification by semi-preparative HPLC gave the cyclosporin alkyne (8 mg, 17%) as an off-white solid: $^1$H NMR (300 MHz, CDCl$_3$) δ 8.14 (d, J=9.7 Hz, 1H), 7.78 (d, J=7.3 Hz, 1H), 7.48 (d, J=8.5 Hz, 1H), 7.35-7.30 (m, 5H), 7.21 (d, J=7.5 Hz, 1H), 5.70 (dd, J=11.0, 4.0 Hz, 1H), 5.38 (d, J=6.8 Hz, 1H), 5.33-5.29 (m, 1H), 5.20-4.96 (m, 5H), 4.83 (t, J=7.3 Hz, 1H), 4.74-4.67 (m, 2H), 4.51 (t, J=7.2 Hz, 1H), 3.88 (t, J=6.5 Hz, 1H), 3.57 (s, 2H), 3.52-3.45 (m, 10H), 3.38 (s, 3H), 3.25 (s, 3H), 3.13 (s, 3H), 3.09 (s, 3H), 2.71 (s, 3H), 2.70 (s, 3H), 2.16-1.62 (m, 10H), 1.43-1.19 (m, 16H), 1.01-0.79 (m, 35H); ESI MS m/z 1277 [C$_{68}$H$_{113}$N$_{11}$O$_{12}$+H]$^+$; HPLC>99% (AUC), t$_R$=20.43 min.

Example 40

Preparation of 1-(Trimethylsilyl)propyn-3-yl Cyclosporin Alkyne

A suspension of cyclosporin alkyne from Example 3 (50 mg, 0.04 mmol), cesium carbonate (326 mg, 1.0 mmol), sodium iodide (152 mg, 1.0 mmol) and copper(I) iodide (190 mg, 1.0 mmol) in DMF (2 mL) was stirred at room temperature for 30 min. 3-Bromo-1-(trimethylsilyl)-1-propyne (0.11 mL, 0.8 mmol) was added dropwise and resulting mixture was stirred at room temperature for 15 min. The blue suspension was diluted with Et$_2$O and filtered. The filtrate was washed twice with H$_2$O. The combined aqueous layers were extracted with Et$_2$O. The combined organics were washed with brine, dried over Na$_2$SO$_4$, and concentrated. Purification by semi-preparative HPLC gave the 1-(trimethylsilyl)propyn-3-yl cyclosporin alkyne (26 mg, 50%) as an off-white solid: $^1$H NMR (300 MHz, CDCl$_3$) δ 8.09 (d, J=9.4 Hz, 1H), 7.77 (d, J=7.5 Hz, 1H), 7.47 (d, J=8.3 Hz, 1H), 7.23 (d, J=7.8 Hz, 1H), 5.70 (dd, J=10.9, 3.9 Hz, 1H), 5.38 (d, J=6.6 Hz, 1H), 5.28 (dd, J=11.5, 3.6 Hz, 1H), 5.19-4.96 (m, 4H), 4.84 (t, J=7.4 Hz, 1H), 4.74-4.66 (m, 2H), 4.51 (t, J=7.2 Hz, 1H), 3.83 (t, J=6.6 Hz, 1H), 3.49 (s, 3H), 3.38 (s, 3H), 3.27 (s, 3H), 3.18 (s, 2H), 3.13 (s, 3H), 3.09 (s, 3H), 2.72 (s, 3H), 2.70 (s, 3H), 2.15-1.98 (m, 10H), 1.91-1.23 (m, 18H), 1.06-0.83 (m, 41H), 0.15 (s, 9H); ESI MS m/z 1297 [C$_{67}$H$_{117}$N$_{11}$O$_{12}$Si+H]$^+$; HPLC 96.8% (AUC), t$_R$=21.59 min.

Example 41

Preparation of Cyclosporin Non-Conjugated Diyne

To a solution of cyclosporin alkyne from Example 40 (18 mg, 0.01 mmol) in MeOH (1 mL) was added potassium carbonate (20 mg, 0.14 mmol) and then the mixture was stirred at room temperature for 1.5 h. The mixture was diluted with EtOAc, washed with $H_2O$ (2×), brine, dried over $Na_2SO_4$, and concentrated. Purification by semi-preparative HPLC gave the cyclosporin non-conjugated diyne (8 mg, 43%) as a white solid: $^1H$ NMR (500 MHz, $CDCl_3$) δ 8.10 (d, J=9.7 Hz, 1H), 7.71 (d, J=7.4 Hz, 1H), 7.46 (d, J=8.3 Hz, 1H), 7.20 (d, J=7.8 Hz, 1H), 5.71 (dd, J=10.9, 4.2 Hz, 1H), 5.40 (d, J=6.6 Hz, 1H), 5.28 (dd, J=11.6, 3.7 Hz, 1H), 5.17 (d, J=10.9 Hz, 1H), 5.09 (t, J=6.7 Hz, 1H), 5.04-4.98 (m, 2H), 4.84 (app quintet, J=7.2 Hz, 1H), 4.73-4.66 (m, 2H), 4.52 (app quintet, J=7.3 Hz, 1H), 3.85 (t, J=6.6 Hz, 1H), 3.49 (s, 3H), 3.38 (s, 3H), 3.28 (s, 3H), 3.13 (s, 3H), 3.09 (s, 3H), 2.72 (s, 3H), 2.70 (s, 3H), 2.49-2.38 (m, 2H), 2.17-2.09 (m, 5H), 2.02 (t, J=2.7 Hz, 1H), 2.01-1.95 (m, 1H), 1.84-1.59 (m, 7H), 1.53-1.41 (m, 4H), 1.36-1.24 (m, 12H), 1.04-0.84 (m, 40H); ESI MS m/z 1225 $[C_{64}H_{109}N_{11}O_{12}+H]^+$; HPLC 99.0% (AUC), $t_R$=18.61 min; and cyclosporin alkynylallene (6.7 mg, 36%) as a white solid: $^1H$ NMR (500 MHz, $CDCl_3$) δ 8.07 (d, J=9.6 Hz, 1H), 7.75 (d, J=7.2 Hz, 1H), 7.52 (d, J=8.4 Hz, 1H), 7.29 (d, J=7.8 Hz, 1H), 5.70 (dd, J=10.9, 2.5 Hz, 1H), 5.40-5.35 (m, 2H), 5.29 (dd, J=10.9, 4.5 Hz, 1H), 5.17 (d, J=10.9 Hz, 1H), 5.10 (t, J=6.4 Hz, 1H), 5.05-5.01 (m, 2H), 4.96 (d, J=6.9 Hz, 1H), 4.84 (t, J=7.1 Hz, 1H), 4.73-4.67 (m, 2H), 4.51 (app quintet, J=7.2 Hz, 1H), 3.48 (t, J=6.6 Hz, 1H), 3.38 (s, 3H), 3.26 (s, 3H), 3.14 (s, 3H), 3.10 (s, 3H), 2.72 (s, 3H), 2.70 (s, 3H), 2.15-2.09 (m, 5H), 2.02-1.61 (m, 7H), 1.55-1.25 (m, 11H), 1.04-0.84 (m, 50H); ESI MS m/z 1225 $[C_{64}H_{109}N_{11}O_{12}+H]^+$; HPLC 91.7% (AUC), $t_R$=20.45 min.

Example 42

Preparation of the Acetate of Cyclosporin Non-Conjugated Diyne

A suspension of the acetate of cyclosporin alkyne from Example 6 (50 mg, 0.05 mmol), cesium carbonate (326 mg, 1.0 mmol), sodium iodide (150 mg, 1.0 mmol) and copper(I) iodide (190 mg, 1.0 mmol) in DMF (2 mL) was stirred at room temperature for 30 min. 1-Bromo-2-butyne (90 μL, 1.0 mmol) was added dropwise and the resulting mixture was stirred at room temperature overnight. The blue suspension was diluted with $Et_2O$ and filtered. The filtrate was washed twice with $H_2O$. The combined aqueous layers were extracted with $Et_2O$. The combined organics were washed with brine, dried over $Na_2SO_4$, and concentrated. Purification by semi-preparative HPLC gave the acetate of cyclosporin non-conjugated diyne (47 mg, 73%) as a light brown solid: $^1H$ NMR (300 MHz, $CDCl_3$) δ 8.46 (d, J=9.8 Hz, 1H), 8.10 (d, J=6.8 Hz, 1H), 7.81 (d, J=8.9 Hz, 1H), 7.60 (d, J=7.7 Hz, 1H), 5.70 (dd, J=10.9, 4.0 Hz, 1H), 5.23-5.15 (m, 6H), 5.07-4.62 (m, 5H), 4.87 (t,j=6.9 Hz, 1H), 3.43 (s, 3H), 3.29 (s, 3H), 3.24 (s, 3H), 3.19 (s, 3H), 2.70 (s, 3H), 2.68 (s, 3H), 2.49-2.09 (m, 13H), 2.05 (s, 3H), 1.74 (t, J=2.5 Hz, 3H), 1.41-1.26 (m, 12H), 1.12-0.82 (m, 44H); ESI MS m/z 1281 $[C_{67}H_{113}N_{11}O_{13}+H]^+$.

Example 43

Preparation of Cyclosporin Non-Conjugated Diyne

To a solution of the acetate of cyclosporin non-conjugated diyne from Example 42 (47 mg, 0.04 mmol) in MeOH (2 mL) was added potassium carbonate (55 mg, 0.4 mmol) and then the mixture was stirred at room temperature overnight. The mixture was diluted with EtOAc, washed with $H_2O$ (2×), brine, dried over $Na_2SO_4$, and concentrated. Purification by semi-preparative HPLC gave the cyclosporin non-conjugated diyne (23 mg, 46%) as a brown solid: $^1H$ NMR (300 MHz, $CDCl_3$) δ 8.09 (d, J=9.5 Hz, 1H), 7.77 (d, J=7.3 Hz, 1H), 7.47 (d, J=8.4 Hz, 1H), 7.22 (d, J=7.9 Hz, 1H), 5.70 (dd, J=10.9, 4.0 Hz, 1H), 5.37 (d, J=6.7 Hz, 1H), 5.27 (dd, J=11.5, 3.7 Hz, 1H), 5.20-4.96 (m, 5H), 4.84 (t, J=7.3 Hz, 1H), 4.74-4.65 (m, 2H), 4.51 (t, J=7.2 Hz, 1H), 3.85 (t, J=6.6 Hz, 1H), 3.49 (s, 3H), 3H), 3.38 (s, 3H), 3.28 (s, 3H), 3.14 (s, 3H), 3.09 (s, 3H), 2.72 (s, 3H), 2.70 (s, 3H), 2.43-2.01 (m, 15H), 1.78 (t, J=2.5 Hz, 3H), 1.66-1.23 (m, 15H), 1.04-0.83 (m, 40H); ESI MS m/z 1239 $[C_{65}H_{111}N_{11}O_{12}+H]^+$; HPLC>99% (AUC), $t_R$=19.45 min.

Example 44

Preparation of Cyclosporin Alkynyl Alcohol

To a solution of cyclosporin alkyne from Example 3 (100 mg, 0.081 mmol) and paraformaldehyde (133 mg, 0.81 mmol) in DMSO (3 mL) was added benzyltrimethylammonium hydroxide (372 μL, 40% solution in methanol, 0.81 mmol) dropwise over 10 min. The resulting solution was stirred at room temperature for 14 h. The reaction was quenched with water and extracted with diethyl ether (4×25 mL). The combined organic layers were washed with water, brine, dried over sodium sulfate, filtered and concentrated in vacuo. The residue was purified by semi-preparative HPLC to afford the cyclosporin alkynyl alcohol (23 mg, 23%) as a white solid: $^1H$ NMR (500 MHz, $CDCl_3$) δ 7.95 (d, J=9.3 Hz, 1H), 7.52 (d, J=7.3 Hz, 1H), 7.46 (d, J=8.3 Hz, 1H), 7.20 (d, J=7.9 Hz, 1H), 5.69 (dd, J=10.8, 4.3 Hz, 1H), 5.45-5.40 (m, 2H), 5.14 (d, J=11.0 Hz, 1H), 5.13-5.05 (m, 2H), 5.00-4.95 (m, 2H), 4.83 (t, J=6.8 Hz, 1H), 4.64 (dd, J=9.8, 8.4 Hz, 1H), 4.52 (t, J=7.3 Hz, 1H), 4.03 (d, J=6.7 Hz, 2H), 3.94 (t, J=6.7 Hz, 1H), 3.51 (s, 3H), 3.31 (s, 3H), 3.27 (s, 3H), 3.13 (s, 3H), 3.09 (s, 3H), 2.70 (s, 3H), 2.69 (s, 3H), 2.40-0.70 (m, 70H); ESI MS m/z 1217 $[C_{62}H_{109}N_{11}O_{13}+H]^+$; HPLC 98.4% (AUC), $t_R$=18.24 min.

Example 45

Preparation of Cyclosporin Diol

To a mechanically stirred solution of diisopropylamine (2.6 mL, 18 mmol) in THF (50 mL) at −78° C. was added dropwise n-butyllithium (6.6 mL, 2.5 M in hexane, 17 mmol), then the mixture was stirred for 0.5 h. A solution of cyclosporin A (1.0 g, 0.83 mmol) in THF (8 mL) was added, and then the mixture was stirred for 2 h at −78° C. Paraformaldehyde (8.0 g) was heated to 170° C. and the resulting formaldehyde gas was transferred into the reaction via a glass tube which was wrapped with cotton and aluminum foil over 2 h. After stirring another 1 h at −78° C., the reaction mixture was quenched with water (10 mL). The mixture was allowed to warm to room temperature, diluted with ethyl acetate (150 mL), and washed with water (2×50 mL). The organic layer was separated, dried over anhydrous sodium sulfate, and concentrated under vacuum. The crude material was purified by semi-preparative HPLC to afford cyclosporin diol (0.45 g, 44%) as a white solid: $^1H$ NMR (300 MHz, $CDCl_3$) δ 8.09 (d, J=9.9 Hz, 1H), 7.70 (d, J=7.4 Hz, 1H), 7.57 (d, J=8.2 Hz, 1H), 7.15 (overlapped with $CHCl_3$, 1H), 5.70 (dd, J=11.0, 4.0 Hz, 1H), 5.49 (d, J=6.4 Hz, 1H), 5.38-5.30 (m, 3H), 5.16-4.93 (m, 5H), 4.83 (t, J=7.2 Hz, 1H), 4.65 (t, J=9.5 Hz, 1H), 4.54 (t, J=7.2 Hz, 1H), 4.05 (d, J=6.8 Hz, 2H), 3.73 (t, J=6.3 Hz, 1H), 3.49 (s, 3H), 3.30 (s, 3H), 3.25 (s, 3H), 3.15 (s, 3H), 3.11 (s, 3H), 2.70 (s, 3H), 2.69 (s, 3H), 2.50-2.38 (m, 2H), 2.20-1.92 (m, 6H), 1.75-0.65 (m, 64H); ESI MS m/z 1233 $[C_{63}H_{113}N_{11}O_{13}+H]^+$.

Example 46

Preparation of Cyclosporin Diacetate

To a solution of cyclosporin diol from Example 45 (0.43 g, 0.35 mmol) in methylene chloride (5 mL) was added pyridine (0.57 mL, 7.0 mmol) followed by 4-(dimethylamino)pyridine (86 mg, 0.70 mmol) and acetic anhydride (1.0 mL, 10.5 mmol). The reaction mixture was stirred for 2 days at room temperature. The reaction was diluted with ethyl ether (150 mL) and washed with a saturated solution of sodium bicarbonate (30 mL), 1N HCl solution (30 mL) and brine (30 mL). The organic layer was separated, dried over anhydrous sodium sulfate, and concentrated under vacuum. The crude material was purified by semi-preparative HPLC to afford cyclosporin diacetate (0.23 g, 50%) as a white solid: $^1$H NMR (300 MHz, CDCl$_3$) δ 8.60 (d, J=9.8 Hz, 1H), 8.05 (d, J=6.6 Hz, 1H), 7.55 (d, J=7.8 Hz, 1H), 7.49 (d, J=9.3 Hz, 1H), 5.68 (dd, J=11.0, 4.0 Hz, 1H), 5.49 (s, 2H), 5.40-4.95 (m, 8H), 4.85 (t, J=7.5 Hz, 1H), 4.76 (t, J=9.3 Hz, 1H), 4.58-4.34 (m, 3H), 3.37 (s, 3H), 3.27 (s, 3H), 3.23 (s, 3H), 3.20 (s, 3H), 3.14 (s, 3H), 2.67 (s, 3H), 2.66 (s, 3H), 2.48-2.35 (m, 1H), 2.10 (s, 3H), 2.01 (s, 3H), 1.98-1.85 (m, 2H), 1.75-0.65 (m, 67H); ESI MS m/z 1317 $[C_{67}H_{117}N_{11}O_{15}+H]^+$.

Example 47

Preparation of Cyclosporin Aldehyde

Ozone was bubbled into a solution of cyclosporin diacetate from Example 46 (0.22 g, 0.17 mmol) in methylene chloride (10 mL) at −78° C. until a blue color was developed. The mixture was degassed with nitrogen for a few minutes and dimethylsulfide (0.4 mL) was added at −78° C. The reaction mixture was allowed to warm to room temperature and stirred for 3 h. The reaction mixture was concentrated in vacuo and the residue was dissolved in ethyl acetate (120 mL), washed with water (2×20 mL) and brine (30 mL), dried over sodium sulfate, filtered, and concentrated in vacuo to afford cyclosporin aldehyde (0.19 g, 86%) as a white solid. The crude material was carried to the next step without further purification: $^1$H NMR (300 MHz, CDCl$_3$) δ 9.55 (d, J=3.4 Hz, 1H), 8.60 (d, J=9.9 Hz, 1H), 7.96 (d, J=7.1 Hz, 1H), 7.53 (d, J=7.7 Hz, 1H), 7.33 (d, J=9.1 Hz, 1H), 5.68 (dd, J=11.0, 4.0 Hz, 1H), 5.53 (d, J=11.2 Hz, 1H), 5.47 (d, J=11.2 Hz, 1H), 5.30 (dd, J=12.3, 3.6 Hz, 1H), 5.18-4.92 (m, 5H), 4.84 (t, J=6.9 Hz, 1H), 4.72 (t, J=9.6 Hz, 1H), 4.55-4.35 (m, 3H), 3.39 (s, 3H), 3.30 (s, 3H), 3.29 (s, 3H), 3.21 (s, 3H), 3.12 (s, 3H), 2.66 (s, 3H), 2.65 (s, 3H), 2.48-2.30 (m, 3H), 2.10 (s, 3H), 1.99 (s, 3H), 1.80-0.75 (m, 64H); ESI MS m/z 1305 $[C_{65}H_{113}N_{11}O_{16}+H]^+$.

Example 48

Preparation of Cyclosporin Alkyne

To a solution of cyclosporin aldehyde from Example 47 (715 mg, 0.55 mmol) in methanol (7.5 mL) was added potassium carbonate (760 mg, 5.5 mmol) followed by a solution of dimethyl (1-diazo-2-oxopropyl)phosphonate (1.06 g, 5.5 mmol) in methanol (4.5 mL). The resulting mixture was stirred at room temperature overnight. The solution was concentrated under reduced pressure, and then diluted with ethyl acetate (100 mL). The organic layer was washed with water (40 mL). The aqueous layer was extracted with ethyl acetate (3×50 mL). The combined organic layers were dried over anhydrous sodium sulfate, then concentrated under reduced pressure. The crude material was purified by semi-preparative HPLC to yield cyclosporin alkyne (106 mg, 16%) as a white solid: $^1$H NMR (300 MHz, CDCl$_3$) δ 7.94 (d, J=9.9 Hz, 1H), 7.62-7.55 (m, 2H), 7.27 (d, J=9.6 Hz, 1H), 5.68 (dd, J=11.0, 3.8 Hz, 1H), 5.47-5.41 (m, 2H), 5.18-4.92 (m, 6H), 4.91-4.77 (m, 2H), 4.63 (t, J=9.1 Hz, 1H), 4.52 (t, J=7.1 Hz, 1H), 4.03 (d, J=6.6 Hz, 1H), 3.50 (s, 3H), 3.30 (s, 3H), 3.28 (s, 3H), 3.14 (s, 3H), 3.09 (s, 3H), 2.71 (s, 3H), 2.70 (s, 3H), 2.50-2.21 (m, 3H), 2.20-1.57 (m, 16H), 1.56-0.72 (m, 54H); ESI MS m/z 1217 $[C_{62}H_{109}N_{11}O_{13}+H]^+$; HPLC>99% (AUC), $t_R$=18.20 min.

Example 49

Preparation of Cyclosporin yne-ene

To a solution of cyclosporin alkyne from Example 48 (43 mg, 0.04 mmol) in triethylamine (1.5 mL) was added copper(I) iodide (4 mg, 0.02 mmol), followed by dichlorobis (triphenylphosphine)palladium(II) (14 mg, 0.02 mmol) and then vinyl iodide (123 mg, 0.8 mmol). The resulting mixture was stirred at room temperature for 2 h. The solution was filtered through a micro filter and concentrated under reduced pressure. The crude material was purified by semi-preparative HPLC to yield cyclosporin yne-ene (106 mg, 16%) as a white solid: $^1$H NMR (300 MHz, CDCl$_3$) δ 8.20 (d, J=10.3 Hz, 1H), 7.75 (d, J=7.0 Hz, 1H), 7.48 (d, J=8.2 Hz, 1H), 7.26 (overlapped with CHCl$_3$, 1H), 5.81-5.66 (m, 2H), 5.59-5.50 (m, 1H), 5.46-5.33 (m, 2H), 5.26 (dd, J=11.6, 3.7 Hz, 1H), 5.20-5.01 (m, 5H), 4.95 (t, J=6.9 Hz, 1H), 4.84 (t, J=7.6 Hz, 1H), 4.69 (t, J=9.2 Hz, 1H), 4.52 (t, J=7.5 Hz, 1H), 4.03 (d, J=6.5 Hz, 2H), 3.84 (t, J=6.4 Hz, 1H), 3.50 (s, 3H), 3.31 (s, 3H), 3.29 (s, 3H), 3.14 (s, 3H), 2.70 (s, 3H), 2.69 (s, 3H), 2.61-2.50 (m, 1H), 2.22-1.54 (m, 16H), 1.53-0.70 (m, 54H); ESI MS m/z 1243 $[C_{64}H_{111}N_{11}O_{13}+H]^+$; HPLC 96.3% (AUC), $t_R$=21.22 min.

Example 50

Concanavalin A-Stimulated Splenocyte Assay

Male BALB/c mice, at 5 to 7 weeks of age, were sacrificed by CO$_2$ inhalation. Spleens were removed and dissociated by pushing through a nylon cell strainer. The splenocytes were washed in RPMI 1640/5% fetal calf serum (FCS) and pelleted at 400×g. Red blood cells were then lysed by resuspending the cell pellet in ACK lysis buffer (150 mM NH$_4$Cl, 1 mM KHCO$_3$, 0.1 mM EDTA, 3 mL per spleen) for 10 min at room temperature. After pelleting at 400×g, the cells were washed by resuspending in RPMI 1640/5% FCS and repelleting. The cell pellet was resuspended in RPMI 1640/5% FCS and again passed through a cell strainer to remove cell aggregates. The cells were then counted and adjusted to 2×10$^6$ cells/ml in RPMI 1640/10% FCS/50 µM 2-mercaptoethanol. Cell viability was assessed by Trypan blue staining. Cyclosporin A or the test compound and two micrograms of concanavalin A were added to the wells of a 96 well plate, prior to the addition of 2×10$^5$ splenocytes. The cells were cultured in a 37° C. CO$_2$ incubator for 2 days and then pulsed with 1 µCi of [$^3$H] thymidine for 6 hours. Cells were harvested onto filtermats with a TomTec 96 well plate harvester and lysed with H$_2$O. The filtermat and scintillation fluid were sealed in a plastic sleeve. [$^3$H]thymidine incorporation was measured with a Wallac Trilux plate counter. Initial screens were done at a fixed value of 100 ng/ml test compound. $IC_{50}$s were calculated from 7 point concentration-response curves using graphPad software.

Example 51

Murine Ex Vivo Pharmacodynamic Assay

In vivo immunosuppressive activity can be determined for cyclosporin A and the disclosed cyclosporin analog compounds, as described below. The concanavalin A-stimulated splenocyte activity can be assessed in vivo using a method previously described by Peterson et al. (Peterson et al., "A Tacrolimus-Related Immunosuppressant with Biochemical Properties Distinct from Those of Tacrolimus," *Transplantation*, 65:10-18 (1998), which is hereby incorporated by reference in its entirety) or a slightly modified version thereof.

Optimal doses of cyclosporin A or an immunosuppressive compound of the present invention (four different doses of test drug plus a control set of animals with no drug) were administered orally or intravenously to male BALB/c or female C57BL mice. Three mice were tested at each dose. Concanavalin A was injected into the tail vein of the mouse at 4 hours after the administration of cyclosporin A or the immunosuppressive compound. One hour after the concanavalin A injection, the mice were euthanized, the spleens were removed under sterile conditions, and the extent of splenocyte proliferation was measured in a similar manner, as described in Example 50. The percent inhibition relative to control was plotted graphically versus the dose of the immunosuppressive compound and an $ED_{50}$ value was determined. Each dose-response assay for the compound of the present invention was accompanied by a cyclosporin control at a single dose equal to the $ED_{50}$.

Although the invention has been described in detail for the purpose of illustration, it is understood that such detail is solely for that purpose, and variations can be made therein by those skilled in the art without departing from the spirit and scope of the invention which is defined by the following claims.

What is claimed is:
1. A compound of Formula I:

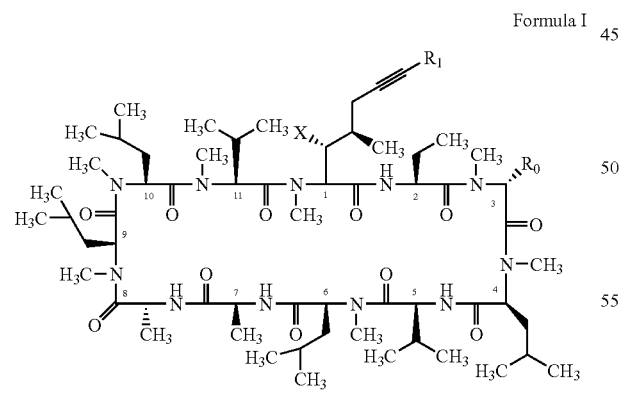

Formula I wherein:
X is OH or OAc;
$R_0$ is H, $CH_2OH$, or $CH_2OR_2$;
$R_1$ is selected from the group consisting of:
 hydrogen;
 halogen;
 $C_2$-$C_6$ saturated or unsaturated, straight or branched carbon chain;
 $C_2$-$C_6$ saturated or unsaturated, straight or branched carbon chain containing substitution or substitutions selected from the group consisting of deuterium, halogen, nitrogen, sulfur, and silicon atom or atoms;
 $C_2$-$C_6$ saturated or unsaturated, straight or branched carbon chain containing a function group or function groups selected from the group consisting of alcohol, ether, aldehyde, ketone, carboxylic ester, and amide;
 $C_2$-$C_4$ saturated or unsaturated, straight or branched carbon chain containing an aryl or a heteroaryl;
 $C_3$-$C_6$-substituted and unsubstituted cycloalkyl;
 substituted and unsubstituted aryl;
 substituted and unsubstituted heteroaryl;
 —$CH_2OH$;
 —CHO;
 —CH=N—$OR_3$; and
 —CH=N—$NR_3R_4$;
$R_2$ is selected from the group consisting of:
 alkanoyl;
 alkenoyl;
 alkynoyl;
 aryloyl;
 arylalkanoyl;
 alkylaminocarbonyl;
 arylaminocarbonyl;
 arylalkylaminocarbonyl;
 alkyloxycarbonyl;
 aryloxycarbonyl; and
 arylalkyloxycarbonyl;
$R_3$ or $R_4$ are the same or different and independently selected from the group consisting of:
 hydrogen;
 $C_1$-$C_6$ saturated straight or branched carbon chain;
 $C_3$-$C_6$ unsaturated straight or branched carbon chain;
 $C_3$-$C_6$-substituted and unsubstituted cycloalkyl;
 $C_1$-$C_4$ carbon chain containing an aryl or heteroaryl;
 substituted and unsubstituted aryl;
 substituted and unsubstituted heteroaryl;
 alkanoyl;
 alkenoyl;
 alkynoyl;
 aryloyl;
 arylalkanoyl;
 alkylaminocarbonyl;
 arylaminocarbonyl;
 arylalkylaminocarbonyl;
 alkyloxycarbonyl;
 aryloxycarbonyl; and
 arylalkyloxycarbonyl; and
$R_3$ together with $R_4$ results in the formation of a cyclic moiety of $C_2$-$C_6$ optionally containing heteroatom or heteroatoms,
or a pharmaceutically acceptable salt thereof.

2. The compound according to claim 1, wherein X is OH or OAc, and $R_0$ is H, $CH_2OH$, or $CH_2OAc$.

3. The compound according to claim 2, wherein $R_1$ is H.

4. The compound according to claim 2, wherein $R_1$ is selected from the group consisting of F, Cl, Br, and I.

5. The compound according to claim 2, wherein $R_1$ is selected from the group consisting of $CH=CH_2$, $CH=CHCH_3$, $CH=CHCH_2CH_3$, $C(CH_3)=CH_2$, $CH=CD_2$, $CH=CHCD_3$, and $CH=CDCD_3$, and wherein the carbon-carbon double bond is a cis or a trans geometric isomer.

6. The compound according to claim 2, wherein $R_1$ is selected from the group consisting of CH=CHF, CH=CHCl, CH=CHBr, CH=CHI, CH=$CF_2$, and $CH=CCl_2$, and wherein the carbon-carbon double bond is a cis or a trans geometric isomer.

7. The compound according to claim 2, wherein $R_1$ is selected from the group consisting of $C\equiv CH$, $C\equiv CCH_3$, $C\equiv CCD_3$, $C\equiv CCH_2CH_3$, $C\equiv CCH_2CH_2CH_3$, and $C\equiv C$-cyclopropyl.

8. The compound according to claim 2, wherein $R_1$ is selected from the group consisting of $CH_2C\equiv CH$, $CH_2C\equiv CCH_3$, $CH_2C\equiv CCH_2CH_3$, $CH_2CH=CH_2$, $CH_2CH=CHCH_3$, and $CH_2CH=CHCH_2CH_3$, and wherein the carbon-carbon double bond is a cis or a trans geometric isomer.

9. The compound according to claim 2, wherein $R_1$ is selected from the group consisting of $C\equiv C-C\equiv CH$, $C\equiv C-C\equiv CCH_3$, $C\equiv CCH=CH_2$, $C\equiv CCH=CHCH_3$, $CH=CHC\equiv CH$, $CH=CHC\equiv CCH_3$, $CH=CHCH=CH_2$, and $CH=CHCH=CHCH_3$, and wherein the carbon-carbon double bond is a cis or a trans geometric isomer.

10. The compound according to claim 2, wherein $R_1$ is cyclopropyl.

11. The compound according to claim 2, wherein $R_1$ is selected from the group consisting of $CH_2OH$, $-CHO$, $CH(OH)CH_3$, $C(=O)CH_3$, $CH=N-OCH_3$, $CH=N-OCH_2CH_3$, $CH=N-NHCH_3$, and $CH=N-N(CH_3)_2$.

12. A pharmaceutical composition comprising a pharmaceutically acceptable carrier and a therapeutically effective amount of the compound of claim 1.

* * * * *